US007490048B2

(12) United States Patent
Joao

(10) Patent No.: US 7,490,048 B2
(45) Date of Patent: Feb. 10, 2009

(54) APPARATUS AND METHOD FOR PROCESSING AND/OR FOR PROVIDING HEALTHCARE INFORMATION AND/OR HEALTHCARE-RELATED INFORMATION

(76) Inventor: Raymond Anthony Joao, 122 Bellevue Pl., Yonkers, NY (US) 10703

( * ) Notice: Subject to any disclaimer, the term of this patent is extended or adjusted under 35 U.S.C. 154(b) by 1204 days.

(21) Appl. No.: 09/987,226

(22) Filed: Nov. 14, 2001

(65) Prior Publication Data

US 2002/0032583 A1 Mar. 14, 2002

Related U.S. Application Data

(60) Provisional application No. 60/286,422, filed on Apr. 25, 2001.

(51) Int. Cl.
*G06F 19/00* (2006.01)
(52) U.S. Cl. .................. 705/3; 705/2; 715/530
(58) Field of Classification Search .......... 705/2, 705/3; 715/530
See application file for complete search history.

(56) References Cited

U.S. PATENT DOCUMENTS

| 3,978,850 A | 9/1976 | Moore et al. |
|---|---|---|
| 4,110,723 A | 8/1978 | Hetz et al. |
| 4,170,987 A | 10/1979 | Anselmo et al. |
| 4,209,022 A | 6/1980 | Dory |
| 4,235,454 A | 11/1980 | Gray et al. |
| 4,242,911 A | 1/1981 | Martin |
| 4,251,850 A | 2/1981 | Kalbitz et al. |
| 4,290,114 A | 9/1981 | Sinay |
| 4,491,725 A | 1/1985 | Pritchard |
| 4,641,659 A | 2/1987 | Sepponen |
| 4,674,108 A | 6/1987 | Asahina et al. |
| 4,674,512 A | 6/1987 | Rolf |
| 4,731,725 A | 3/1988 | Suto et al. |
| 4,733,354 A | 3/1988 | Potter et al. |
| 4,803,625 A | 2/1989 | Fu et al. |
| 4,803,652 A | 2/1989 | Maeser et al. |
| 4,835,372 A | 5/1989 | Gombrich et al. |
| 4,895,518 A | 1/1990 | Arnold et al. |

(Continued)

OTHER PUBLICATIONS

L. McCullough et al., "The Development of a Microcomputer-Based Mental Health Information System, A Potential Tool for Bridging the Scientist-Practitioner Gap", American Psychologist, Feb. 1986, pp. 207-213.

(Continued)

*Primary Examiner*—C Luke Gilligan
*Assistant Examiner*—Lena Najarian
(74) *Attorney, Agent, or Firm*—Raymond A. Joao, Esq.

(57) ABSTRACT

A computer-implemented method, including processing, with a processor, a request by a person or entity to access, obtain, change, alter, or modify, an individual's or patient's healthcare record or file which contains healthcare information or healthcare-related information personal to the individual or patient, generating a message containing information regarding the person or entity and/or identification information regarding the person or entity, and containing an actual change, alteration, or modification, sought to be made or made to the individual's or patient's healthcare record or file, and transmitting the message to a communication device of the individual or patient during, concurrently with, at a same time as, or prior to a completion of, an accessing, obtaining, changing, altering, or modifying, of the individual's or patient's healthcare record or file or a processing of the request.

40 Claims, 28 Drawing Sheets

U.S. PATENT DOCUMENTS

| | | |
|---|---|---|
| 5,036,852 A | 8/1991 | Leishman |
| 5,070,452 A | 12/1991 | Doyle, Jr. et al. |
| 5,090,417 A | 2/1992 | Mollan et al. |
| 5,185,857 A | 2/1993 | Rozmanith et al. |
| 5,217,379 A | 6/1993 | Kirschenbaum et al. |
| 5,219,322 A | 6/1993 | Weathers |
| 5,235,510 A | 8/1993 | Yamada et al. |
| 5,255,187 A | 10/1993 | Sorensen |
| 5,262,943 A | 11/1993 | Thibado et al. |
| 5,265,010 A | 11/1993 | Evans-Paganelli et al. |
| 5,279,294 A | 1/1994 | Anderson et al. |
| 5,305,748 A | 4/1994 | Wilk |
| 5,324,077 A | 6/1994 | Kessler et al. |
| 5,331,550 A | 7/1994 | Stafford et al. |
| 5,344,324 A | 9/1994 | O'Donnell et al. |
| 5,360,005 A | 11/1994 | Wilk |
| 5,404,292 A | 4/1995 | Hendrickson |
| 5,415,167 A | 5/1995 | Wilk |
| 5,424,945 A | 6/1995 | Bell |
| 5,435,324 A | 7/1995 | Brill |
| 5,437,278 A | 8/1995 | Wilk |
| 5,465,082 A | 11/1995 | Chaco |
| 5,530,438 A | 6/1996 | Bickham et al. |
| 5,544,649 A | 8/1996 | David et al. |
| 5,544,651 A | 8/1996 | Wilk |
| 5,551,436 A | 9/1996 | Yago |
| 5,583,758 A | 12/1996 | McIlroy et al. |
| 5,594,638 A | 1/1997 | Iliff |
| 5,615,110 A | 3/1997 | Wong |
| 5,660,176 A | 8/1997 | Iliff |
| 5,666,953 A | 9/1997 | Wilk |
| 5,696,981 A | 12/1997 | Shovers |
| 5,708,422 A | 1/1998 | Blonder et al. |
| 5,724,968 A | 3/1998 | Iliff |
| 5,761,334 A | 6/1998 | Nakajima et al. |
| 5,776,057 A | 7/1998 | Swenson et al. |
| 5,779,634 A | 7/1998 | Ema et al. |
| 5,797,901 A | 8/1998 | Cosmescu |
| 5,801,755 A | 9/1998 | Echerer |
| 5,807,246 A | 9/1998 | Sakaguchi et al. |
| 5,807,256 A | 9/1998 | Taguchi et al. |
| 5,839,438 A | 11/1998 | Graettinger et al. |
| 5,845,255 A * | 12/1998 | Mayaud ................ 705/3 |
| 5,862,803 A | 1/1999 | Besson et al. |
| 5,867,821 A * | 2/1999 | Ballantyne et al. .......... 705/2 |
| 5,868,669 A | 2/1999 | Iliff |
| 5,876,351 A | 3/1999 | Rohde |
| 5,878,337 A | 3/1999 | Joao et al. |
| 5,878,746 A | 3/1999 | Lemelson et al. |
| 5,895,354 A | 4/1999 | Simmons |
| 5,899,857 A | 5/1999 | Wilk |
| 5,903,830 A | 5/1999 | Joao et al. |
| 5,910,107 A | 6/1999 | Iliff |
| 5,915,241 A | 6/1999 | Giannini |
| 5,930,759 A | 7/1999 | Moore et al. |
| 5,935,060 A | 8/1999 | Iliff |
| 5,954,641 A | 9/1999 | Kehr et al. |
| 5,957,854 A | 9/1999 | Besson et al. |
| 5,961,332 A | 10/1999 | Joao |
| 5,961,448 A | 10/1999 | Swenson et al. |
| 5,974,124 A | 10/1999 | Schlueter, Jr. et al. |
| 5,974,389 A * | 10/1999 | Clark et al. .................... 705/3 |
| 5,988,851 A | 11/1999 | Gent |
| 5,992,742 A | 11/1999 | Sullivan et al. |
| 6,014,629 A | 1/2000 | DeBruin-Ashton |
| 6,021,202 A * | 2/2000 | Anderson et al. ............. 705/54 |
| 6,047,270 A | 4/2000 | Joao et al. |
| 6,073,106 A * | 6/2000 | Rozen et al. .................... 705/3 |
| 6,076,066 A | 6/2000 | DiRienzo et al. |
| 6,090,044 A | 7/2000 | Bishop et al. |
| 6,208,973 B1 | 3/2001 | Boyer et al. |
| 6,216,104 B1 * | 4/2001 | Moshfeghi et al. .......... 704/260 |
| 6,273,856 B1 | 8/2001 | Sun et al. |
| 6,283,761 B1 | 9/2001 | Joao |
| 6,302,844 B1 * | 10/2001 | Walker et al. ................ 600/300 |
| 6,341,265 B1 | 1/2002 | Provost et al. |
| 6,345,260 B1 | 2/2002 | Cummings et al. |
| 6,523,009 B1 * | 2/2003 | Wilkins ............................ 705/3 |
| 6,529,725 B1 | 3/2003 | Joao et al. |
| 6,662,194 B1 | 12/2003 | Joao |
| 6,776,341 B1 | 8/2004 | Sullivan et al. |
| 6,799,725 B1 | 10/2004 | Hess et al. |
| 6,804,656 B1 | 10/2004 | Rosenfeld et al. |
| 6,988,075 B1 | 1/2006 | Hacker |
| 7,059,526 B1 | 6/2006 | Sullivan et al. |
| 7,096,003 B2 | 8/2006 | Joao et al. |
| 7,370,797 B1 | 5/2008 | Sullivan et al. |
| 2001/0032099 A1 | 10/2001 | Joao |
| 2001/0041991 A1 * | 11/2001 | Segal et al. ..................... 705/3 |
| 2001/0049610 A1 * | 12/2001 | Hazumi .......................... 705/3 |
| 2001/0051920 A1 | 12/2001 | Joao et al. |
| 2002/0004727 A1 * | 1/2002 | Knaus et al. ..................... 705/3 |
| 2002/0025797 A1 | 2/2002 | Joao et al. |
| 2002/0026332 A1 * | 2/2002 | Snowden et al. ................ 705/3 |
| 2002/0038424 A1 | 3/2002 | Joao et al. |
| 2003/0028399 A1 * | 2/2003 | Davis et al. ..................... 705/2 |
| 2003/0074248 A1 * | 4/2003 | Braud et al. .................... 705/9 |
| 2003/0158754 A1 * | 8/2003 | Elkind ............................ 705/3 |
| 2004/0107192 A1 | 6/2004 | Joao |
| 2004/0185830 A1 | 9/2004 | Joao et al. |
| 2004/0199765 A1 * | 10/2004 | Kohane et al. ............... 713/165 |
| 2005/0170814 A1 | 8/2005 | Joao et al. |
| 2008/0120190 A1 | 5/2008 | Joao et al. |

OTHER PUBLICATIONS

U.S. Appl. No. 60/169,065, filed Dec. 6, 1999, Snowden et al.
U.S. Appl. No. 60/235,977, filed Sep. 28, 2000, Davis et al.
Watson, The doctor is in!, Jun. 1995, Accounting Technology, vol. 11, Iss. 5, pp. 24-30.
EDIComm Unveils All-Payer Solution for Healthcare EDI Transactions, Feb. 1999, Business Wire.
U.S. Appl. No. 09/489,657, Joao et al.
U.S. Appl. no. 60/172,555, Joao.

* cited by examiner

APPARATUS AND METHOD FOR PROCESSING AND/OR FOR PROVIDING HEALTHCARE INFORMATION AND/OR HEALTHCARE-RELATED INFORMATION

RELATED APPLICATIONS

This application claims the benefit of priority of U.S. Provisional Patent Application Ser. No. 60/286,422, filed Apr. 25, 2001 and entitled "APPARATUS AND METHOD FOR PROCESSING AND/OR FOR PROVIDING HEALTHCARE INFORMATION AND/OR HEALTHCARE-RELATED INFORMATION", the subject matter and teachings of which are hereby incorporated by reference herein.

FIELD OF THE INVENTION

The present invention pertains to an apparatus and a method for processing and/or for providing healthcare information and/or healthcare-related information and, in particular, to an apparatus and a method for processing and/or for providing healthcare information and/or healthcare-related information for a variety of healthcare and healthcare related applications.

BACKGROUND OF THE INVENTION

Each year, tens of millions of individuals seek or need the assistance of healthcare professionals. In order to perform proper diagnoses and to prescribe appropriate treatments, healthcare professionals or providers typically rely on information which is obtained from patients, relatives of patients, previous providers, and/or healthcare facility and/or hospital staff members. The need to have accurate and/or up-to-date data and/or information, in providing healthcare services and/or healthcare-related services, cannot be emphasized enough.

Stories constantly emerge about patients receiving the wrong treatments, having the wrong surgical procedures performed on themselves, receiving a drug or drugs which fatally and/or otherwise adversely interact with another drug or drugs, etc., with stories going on and on. Recently, it has been estimated that between 44,000 and 98,000 individuals die, in the United States alone, as the result of errors or mistakes made by doctors, healthcare providers, and/or healthcare facility workers. There is no doubt that many of these deaths result from inaccurate and/or erroneous information and/or the lack of the availability of correct and/or up-to-date information.

Another problem lies with the fact that the main source of patient information, medical histories, family histories, etc., upon which doctors or providers may base their diagnoses and/or treatments, are patients who usually supply this information on questionnaires or forms just prior to seeing the healthcare provider and/or during a preliminary interview with the provider. In this regard, information obtained from these questionnaires or forms, as well as from these preliminary interviews with the providers, may not necessarily result in sufficient, comprehensive, and/or accurate, information being obtained regarding the patient. Further, there is no guarantee that the same information will be provided, in a uniform manner, to a next or different provider. As a result, patient information may not be uniformly distributed and/or be available to providers at the point of treatment and/or otherwise.

Another problem which exists in the current healthcare system is that doctors or other providers do not always have the latest information and/or research material available to them prior to, and/or during, the diagnosis and/or treatment process.

It is also no secret that healthcare costs are rising at ever-increasing rates and that insurance companies and other healthcare payers expend great resources in processing and reconciling treatment claims and/or claims for healthcare services and/or benefits. Typically, these insurance and/or benefits claims take place in a paper-based environment and, as a result are slow and inefficient. Fraudulent claims and/or claims which cannot be verified pose another major problem for healthcare payers and insurance companies. These problems only serve to add to the growing costs of healthcare, delayed treatments, and a general dissatisfaction with the current healthcare system.

Another problem lies in making up-to-date training materials conveniently available to providers in order to allow providers to remain current with state-of-the-art information and training techniques.

Other problems lie in maintaining patient healthcare records or files private, in safeguarding patient healthcare records or files, in providing notification to patients and other individuals when others have accessed, obtained, and/or made changes to their respective healthcare records or files, and in enabling patients and individuals to restrict and/or limit access to their healthcare records or files.

The list of problems with the current healthcare system goes on and on. In view of the above, there is a great need for an apparatus and a method for providing healthcare information and/or healthcare-related information to the various providers, payers, patients, third party individuals, and/or insurance brokers, agents and/or other intermediaries, which overcomes the shortcomings of the prior art.

SUMMARY OF THE INVENTION

The present invention provides an apparatus and methods for providing healthcare information and/or healthcare-related information which overcomes the shortcomings of the prior art.

The present invention is directed to an apparatus and a method for processing and/or for providing healthcare information and/or healthcare-related information and, in particular, to an apparatus and a method for processing and/or for providing healthcare information and/or healthcare-related information for a variety of healthcare and healthcare related applications.

The apparatus and method of the present invention facilitates the creation and management of a comprehensive healthcare processing system which can manage patient and client records, doctor and other provider records, healthcare insurance and/or payer records, and thereby provide an apparatus, system and methods for providing a variety and a multitude of healthcare information processing applications, processes and services.

The present invention facilitates improved healthcare quality, efficient information collection, processing and dissemination, efficient diagnosis and treatment, cost efficiency, cost containment, as well as many other benefits and advantages as will be described herein. The apparatus and method of the present invention also facilitates the distribution and management of healthcare insurance, life insurance, disability insurance, as well as claims processing related thereto.

The present invention also provides an apparatus and a method for providing a comprehensive processing system which incorporates data and/or information from any combination and/or all of the participants in the healthcare field, including patients, providers, payers or insurance companies, and/or brokers, agents and/or other intermediaries who act on behalf of any of the above-identified persons or entities.

The apparatus of the present invention includes a central processing computer or central processing computer system which can be a network or server computer. The apparatus also includes a healthcare provider communication device or computer which is associated with a healthcare provider such as a healthcare professional, a hospital, a clinic, and/or any other provider of services described herein. The healthcare provider computer(s) can communicate with, and operate in conjunction with, the central processing computer and/or any of the other computers and/or computer systems or communication devices described herein.

The apparatus can also include a healthcare payer communication device or computer which is associated with a healthcare payer such as a healthcare insurer, insurance company, health maintenance organization, a clinic, and/or any other payer of healthcare services and products described herein. The healthcare payer computer(s) can communicate with, and operate in conjunction with, the central processing computer and/or any of the other computers and/or computer systems or communication devices described herein.

The apparatus can also include a patient or individual user communication device or computer which is associated with a healthcare patient such as a patient, user, or client who seeks or who is provided with healthcare and/or related services, products and/or related information. The patient computer(s) can communicate with, and operate in conjunction with, the central processing computer and/or any of the other computers and/or computer systems described herein.

The apparatus can also include an intermediary communication device or computer which is associated with an intermediary, a broker, an agent, and/or any other individual and/or entity, that can utilize the present invention in order to act for and/or on behalf of any other individual, party, or entity, described herein. The intermediary computer(s) can communicate with, and operate in conjunction with, the central processing computer and any of the other computers and/or computer systems described herein.

Each of the central processing computer(s), the provider computer(s), the payer computer(s), the patient computer(s), and/or the intermediary computer(s), can transmit information to, as well as receive information from, any of the computers described herein. In this regard, each of the computers can communicate with, process information from, and/or share data and/or information with, each other and/or any other computer or computers described herein and/or utilized in conjunction with the present invention. In this manner, data and/or information transfer between any of the computers can take place in a bi-directional manner.

The central processing computer(s), the provider computer(s), the payer computers(s), the patient computer(s), and the intermediary computer(s), can communicate with one another, and/or be linked to one another, over a communication network, a telecommunication network, a telephone network, a line-connected network, and/or a wireless communication network.

The present invention can be utilized on, or over, the Internet and/or the World Wide Web and/or on, or over, any other communication network or system, including, but not limited to, a communication network or system, a telecommunication network or system, a telephone communication network or system, a cellular communication network or system, a wireless communication network or system, a wireless Internet network or system, a wireless World Wide Web network or system, a line or wired communication network or system, a digital communication network or system, a personal communication network or system, a personal communication services (PCS) network or system, a satellite communication network or system, a broad band communication network or system, a low earth orbiting (LEO) satellite network or system, a public switched telephone network or system, a telephone communication network or system, a radio communication network or system, and/or any other communication network or system, and/or any combination of the above communication networks or systems.

The apparatus and method of the present invention can utilize electronic commerce technologies and security methods, techniques and technologies, in any and/or all of the instances of data and/or information processing, and/or data and/or information transmission described herein.

Each of the central processing computer(s), as well as each of the computers or communication devices associated with each of the herein-described users, patients, providers, payers, and/or intermediaries, can include a central processing unit or CPU, a random access memory device(s) (RAM), a read only memory device(s), and a user input device. Each of the central processing computer(s), as well as each of the computers or communication devices associated with each of the herein-described users, patients, providers, payers, and/or intermediaries, can also include a display device, a transmitter(s), a receiver, a database(s), and an output device. The database(s) can contain any and/or all of the data and or information which is needed to perform the various processing methods, services, functions and/or operations, described herein.

The apparatus and method of the present invention can be utilized in numerous preferred embodiments in order to provide a vast array of healthcare and healthcare-related services for any one or more of the various parties described herein. Any patient, user, provider, payer, and/or intermediary, may utilize the present invention in the same, similar and/or analogous manner.

The present invention can be utilized for a number of applications, including, but not limited to, determining and/or ascertaining a medical or healthcare diagnosis, verifying and/or checking a diagnosis or treatment, or performing a self-diagnosis. The present invention can be utilized by any of the parties described herein.

The present invention can perform a diagnosis from data and/or information which can be entered by a user or provider, from data and/or information which can be obtained from medical or healthcare devices, machines, and/or equipment, and/or from data and/or information which can be entered by a user or provider in conjunction with, or along with, data and/or information which can be obtained from medical or healthcare devices, machines, and/or equipment.

The present invention can be utilized to create and maintain comprehensive patient databases which can be accessed via a network environment and/or otherwise, to perform healthcare and/or healthcare-related diagnoses, to provide healthcare and/or healthcare-related expected prognoses, to provide healthcare and/or healthcare-related treatment plans or programs, and/or to provide healthcare and/or healthcare-related treatment progress reports and/or evaluations.

The present invention can also be utilized in order to provide training and continuing education services for healthcare and/or healthcare-related professionals, to provide healthcare, healthcare-related, and/or wellness information, to provide information about healthcare and/or healthcare-related patient, providers, payers, and/or intermediaries, to provide scheduling management services for providers, to provide notification services for patients, providers, payers and/or intermediaries, and/or any other parties described herein, and/or to locate providers, payers and/or intermediaries.

The present invention can also be utilized in order to provide healthcare and/or healthcare-related claim processing services, claims submissions, claim processing, claim status checking, and claim reconciliation, claim fraud prevention, treatment evaluation, healthcare and/or healthcare insurance policy generation, management and administration, provider, payer and/or intermediary evaluation, drug and/or treatment interactivity, treatment, medication and/or organ availability and/or notification services, patient, provider, payer, intermediary and/or third party, notification services. The present invention can also be utilized as a clearinghouse for facilitating the offering, selling, buying, trading, and/or other commerce and/or transactions, involving healthcare and/or healthcare-related services, products and/or goods.

The various computers and/or communication devices can be utilized to transmit and/or to receive transmissions, information, messages, and/or notification messages and/or signals, to and/or between, the respective parties associated with the respective computers and/or communication devices. The transmission of information, messages, and/or notification messages and/or signals can be effected via any one or more of e-mail messages, telephone messages, beeper or pager messages, physical mail delivery, electronic data transmission, and/or can be made via any other suitable and/or appropriate communication method and/or technique.

The present invention can be utilized in order to perform a diagnosis of a sickness, illness and/or other condition. The present invention can also be utilized to ensure that a proper treatment and/or procedure is performed on the patient, and/or to ensure that a subsequent treatment and/or treatments are performed as prescribed. The present invention can also be utilized in order to prevent medical and/or surgical mistakes, mishaps and/or other instances when improper treatment could occur.

The present invention can also be utilized to allow a subsequent care provider to re-evaluate a patient's condition and/or records and to seek additional assistance for the patient, and/or to perform a separate and independent assessment and/or diagnosis of the patient.

The present invention can also be utilized in order to access a patient's or a client's record(s) and input information concerning the treatment and/or procedure to be performed. Thereafter, the present invention can provide notification to a healthcare professional that the treatment and/or procedure may be a prescribed treatment or procedure or a non-prescribed treatment and/or procedure.

Any and/or all processing described herein can be performed in conjunction with a patient's medical history, family history, allergic conditions information, and/or with any other information deemed important and/or essential in an individual's healthcare diagnoses and/or treatments.

The present invention can also be utilized to perform treatment evaluations and/or treatment monitoring so as to allow for an evaluation and/or a monitoring of treatment and/or for providing training for healthcare providers and/or professionals. The present invention can also be utilized in order to allow payer and/or insurance companies to evaluate treatments, treatment plans, treatment progress, and/or any other evaluations and/or verifications for healthcare claims processing.

The present invention can provide treatment evaluation and/or monitoring for healthcare payers which can be utilized for performing claims processing, provider evaluations, patient evaluations, and/or any other useful and/or desired purpose.

The present invention can also be utilized to create and maintain a comprehensive patient healthcare database which can be accessed by any provider, payer, intermediary, and/or other party or user, in order to access the patient's healthcare files and/or records. The comprehensive database can provide a data and/or information source which can be accessed by any provider, from anywhere in the world, and at any time, in order to obtain information about a patient in his, her, or its care. Payers can also utilize the comprehensive database in order to ascertain payment eligibility, the existence of pre-existing conditions and/or to obtain any other useful information.

The present invention can also be utilized in order to find and/or to locate providers and/or payers of, and for, respectively, various healthcare treatments, healthcare services and/or healthcare goods or products and/or healthcare-related goods or products. The present invention can also be utilized to find a payer or insurance company for providing desired coverage and/or for paying for certain treatments and/or procedures.

The present invention can also be utilized to find and/or locate supplies, body organs, blood, medications, and/or any other goods, products, and/or supplies, etc. The present invention can also be utilized by intermediaries, such as insurance brokers, who need to find certain insurance companies and/or payers who meet the needs of certain patients and/or clients, and/or other individuals and/or third parties.

The present invention can also be programmed to provide notification of the availability of a provider, the emergence of a patient in need of a certain care, the availability of a payer or an insurance company to offer a policy or a certain policy, the availability of a healthcare facility to provide certain care, the availability of certain supplies, a body organ, a blood type, an expiration of an insurance policy (i.e. healthcare insurance, life insurance, disability insurance, etc.,) and/or the occurrence of any event which may be of interest to any of the patients, users, providers, payers, and/or intermediaries, described herein.

The present invention can also be utilized to schedule appointments with any of the patients, providers, payers, and/or intermediaries, described herein.

The present invention can be utilized by intermediaries, such as, but not limited to brokers, insurance brokers, agents, and others, in order to service their respective clients. The present invention can be utilized to prepare policy quotes, to compare available policies, to generate and/or underwrite policies, and to service policy claims. In this, manner, the present invention can provide a platform for allowing a broker to provide improved services to his or her clients while also providing for a more paperless working relationship.

The present invention can also be utilized to process healthcare claims. The present invention can allow any of the patients, providers, payers, users, and/or intermediaries, to file claims with the respective party electronically and/or otherwise. The present invention can provide for the processing, tracking and reconciliation, of any and/or all healthcare claims and/or healthcare-related claims.

The present invention can also be utilized to notify any party described herein, as well as any third parties, regarding any event, happening, occurrence, and/or any aspect of any claim submission and/or processing activities.

The present invention can also provide for automatic claim submission via the central processing computer once a final diagnosis and treatment has been prescribed by a provider and/or upon the occurrence of an examination and/or the administration of a treatment.

The present invention can also be utilized, in the manner described above in connection with claiming healthcare insurance benefits, disability insurance benefits, and/or life insurance benefits.

The present invention can also be utilized to administer and/or maintain financial accounts for, and/or on behalf of, any of the patients, users, providers, payers, and/or intermediaries, described herein. The present invention can maintain detailed records of any and/or all of such transfers and/or transactions and provide periodic account statements to the respective parties maintaining accounts with the present invention.

The apparatus and method of the present invention can also utilize electronic signatures and/or process electronic signatures and/or electronic signature information which can correspond to any of the herein-described parties in performing any of the herein-described processing routines and/or functions.

The apparatus and method of the present can also be utilized as a healthcare training simulator for any of the providers, healthcare providers, healthcare professionals, and/or other providers described herein. The present invention can also be utilized by any user and/or individual wishing to learn about a certain healthcare field or topic. Data and/or information collected and/or stored by the apparatus, which relates to symptoms and/or conditions, as well as responses to treatments, can be utilized in order to present realistic and confidential training scenarios.

The apparatus and method of the present invention can also be utilized in order to maintain patient healthcare records or files private, to safeguard patient healthcare records or files, to provide notification to patients and other individuals when others have accessed, obtained, and/or made changes to their respective healthcare records or files, and/or to enable patients and individuals to restrict and/or limit access to their healthcare records or files.

The present invention can also provide for the security and/or the confidentiality of any and/or all of the data and/or information stored by, and/or processed by, same. Identification cards can also be utilized so as to store pertinent information for any of the respective parties so as to provide the respective party with access to various data and/or information and/or any processing functionality which can be provided by the present invention.

The present invention can also utilize intelligent agents, software agents, and/or mobile agents, which agents can be programmed to act for, and/or on behalf of, any of the parties described herein. The intelligent agent(s) can act on behalf of the respective party in various related interactions and/or other activities which are described as being performed herein and/or which may be incidental and/or related thereto. Therefore, the present invention also provides an agent-based apparatus and method for providing healthcare information and/or healthcare-related information.

The apparatus of the present invention can also be programmed to be self-activating and/or activated automatically. The apparatus of the present invention can also be programmed in order to automatically generate and/or transmit any of the e-mails, electronic message transmissions, electronic notification transmissions, and/or any of the communications, described herein, between any of the parties which utilize the present invention.

The data and/or information, described as being stored in the various databases utilized by the respective computers and/or communication devices can be continuously updated so as to store the latest values for the data and/or information and can be stored and be made available for future processing routines.

Any and/or all of the data and/or information described herein as being stored in any of the various databases, can be linked via relational database techniques and/or via any appropriate database management techniques. The data and/or information can be updated via inputs from any of the computers and/or communication devices described herein, and/or external computers or communication devices, in real-time, and/or via dynamically linked database management techniques. The data and/or information which is stored in the various databases can be linked via any suitable data linking techniques such as, for example, dynamically linked lists (DLLs), linked lists, and object links embedded (OLE's).

Accordingly, it is an object of the present invention to provide an apparatus and a method for processing and/or for providing healthcare information and/or healthcare-related information.

It is another object of the present invention to provide an apparatus and a method for processing and/or for providing healthcare information and/or healthcare-related information, in a network environment.

It is still another object of the present invention to provide an apparatus and a method for processing and/or for providing healthcare information and/or healthcare-related information, which can be utilized in a number of healthcare and/or healthcare-related applications.

It is yet another object of the present invention to provide an apparatus and a method for processing and/or for providing healthcare information and/or healthcare-related information, which provides and/or facilitates the creation and management of a comprehensive healthcare processing system.

It is another object of the present invention to provide an apparatus and a method for performing healthcare diagnoses.

It is still another object of the present invention to provide an apparatus and method for performing a healthcare diagnosis from data and/or information which can be entered by a user or provider.

It is yet another object of the present invention to provide an apparatus and method for performing a healthcare diagnosis from data and/or information which can be obtained from medical or healthcare devices, machines, and/or equipment.

It is another object of the present invention to provide an apparatus and method for performing a healthcare diagnosis from data and/or information which can be entered by a user or provider in conjunction with, or along with, data and/or information which can be obtained from medical or healthcare devices, machines, and/or equipment.

It is still another object of the present invention to provide an apparatus and a method for performing healthcare diagnoses, in a network environment.

It is yet another object of the present invention to provide an apparatus and a method for prescribing healthcare treatments.

It is another object of the present invention to provide an apparatus and a method for prescribing healthcare treatments, in a network environment.

It is still another object of the present invention to provide an apparatus and a method for providing healthcare information which can incorporate data and/or information from any combination and/or all of the participants in the healthcare field, including patients, users, providers, payers or insurance companies, and/or brokers, agents and/or other intermediaries who act on behalf of any of the above-identified persons or entities.

It is another object of the present invention to provide an apparatus and a method for providing healthcare information which can be utilized by a healthcare professional to verify and/or to check a diagnosis.

It is another object of the present invention to provide an apparatus and a method for providing healthcare information which can be utilized by an individual to perform a self-diagnosis.

It is still another object of the present invention to provide an apparatus and a method for providing healthcare information which can be utilized to create and/or to maintain a comprehensive patient database which can be accessed to perform any one or more of healthcare and/or healthcare-related diagnoses, to provide healthcare and/or healthcare-related expected prognoses, to provide healthcare and/or healthcare-related treatment plans or programs, and/or to provide healthcare and/or healthcare-related treatment progress reports and/or evaluations.

It is another object of the present invention to provide an apparatus and a method for providing healthcare information which can be utilized as a healthcare training simulator.

It is another object of the present invention to provide an apparatus and a method for providing healthcare training.

It is another object of the present invention to provide an apparatus and a method for providing healthcare information which can be utilized to provide scheduling management services for providers, payers, providers, users, and/or intermediaries.

It is another object of the present invention to provide an apparatus and a method for providing healthcare information which can be utilized to provide notification services for patients, providers, payers, users, and/or intermediaries.

It is another object of the present invention to provide an apparatus and a method for providing healthcare information which can be utilized to locate providers, payers, patients, users, and/or intermediaries.

It is still another object of the present invention to provide an apparatus and a method for providing healthcare information which can be utilized to provide healthcare claim processing services.

It is yet another object of the present invention to provide an apparatus and a method for providing healthcare information which can be utilized to provide healthcare claim processing services, including any one or more of claims submissions, claim processing, claim status checking, claim reconciliation, and/or claim fraud prevention.

It is another object of the present invention to provide an apparatus and a method for providing healthcare information which can be utilized to provide healthcare treatment evaluation.

It is still another object of the present invention to provide an apparatus and a method for providing healthcare information which can be utilized to provide healthcare insurance policy generation, policy management, and/or policy administration.

It is yet another object of the present invention to provide an apparatus and a method for providing healthcare information which can be utilized to provide provider, payer, and/or intermediary evaluation.

It is another object of the present invention to provide an apparatus and a method for providing healthcare information which can be utilized to provide information regarding drug and/or treatment interactivity, and/or treatment, medication, and/or organ availability.

It is another object of the present invention to provide an apparatus which can be utilized as a clearinghouse for facilitating the offering, selling, buying, trading, and/or other commerce and/or transactions, involving healthcare and/or healthcare-related services, products and/or goods.

It is still another object of the present invention to provide an apparatus and a method for providing healthcare information which can be utilized to ensure that a proper treatment(s) or procedure(s) is prescribed for a patient and/or that a proper treatment and/or procedure is administered to, or performed on, a patient.

It is another object of the present invention to provide an apparatus and a method for providing healthcare information which can be utilized to access a patient's or a client's record(s) and/or to obtain information concerning a treatment and/or a procedure to be performed.

It is still another object of the present invention to provide an apparatus and a method for providing healthcare information which can be utilized to provide healthcare diagnoses in conjunction with a patient's medical history, family history, allergic conditions information, and/or with any other information deemed important and/or essential in the an individual's healthcare diagnosis and/or treatment.

It is still another object of the present invention to provide an apparatus and a method for providing healthcare information which can be utilized to allow payers and/or insurance companies to evaluate treatments, treatment plans, treatment progress, and/or any other evaluations and/or verifications, for healthcare claims processing.

It is yet another object of the present invention to provide an apparatus and a method for providing healthcare information which can be utilized to allow providers or payers to evaluate treatments, treatment plans, treatment progress, and/or any other evaluations and/or verifications, claims processing for providing healthcare and/or related services.

It is still another object of the present invention to provide an apparatus and a method for providing healthcare information which can be utilized to find and/or locate supplies, body organs, blood, medications, and/or any other goods, products, and/or supplies, etc.

It is another object of the present invention to provide an apparatus and a method for providing healthcare information which can be utilized to find and/or locate a payer or insurance company for providing desired coverage and/or for paying for certain treatments and/or procedures.

It is still another object of the present invention to provide an apparatus and a method for providing healthcare information which can be utilized by intermediaries, such as insurance brokers, to find and/or locate insurance companies and/or payers who meet the needs of certain parties.

It is still another object of the present invention to provide an apparatus and a method for providing healthcare information which can be programmed to provide notification of the availability of a provider, the emergence of a patient in need of a certain care, the availability of a payer or an insurance company to offer a policy or a certain policy, the availability of a healthcare facility to provide certain care, the availability of certain supplies, a body organ, a blood type, an expiration of an insurance policy, and/or the occurrence of any event which may be of interest to patients, users, providers, payers, and/or intermediaries.

It is still another object of the present invention to provide an apparatus and a method for providing healthcare information which can be utilized to prepare insurance policy quotes, compare available policies, generate policies, and service policy claims.

It is another object of the present invention to provide an apparatus and a method for providing healthcare information which can be utilized to provide for automatic healthcare claim submission.

It is another object of the present invention to provide an apparatus and a method for providing healthcare information which can be utilized to provide for automatic healthcare claim submission once a final diagnosis has been determined and/or a treatment has been prescribed.

It is still another object of the present invention to provide an apparatus and a method for providing healthcare information which can be utilized to claim healthcare insurance benefits, disability insurance benefits, and/or life insurance benefits.

It is yet another object of the present invention to provide an apparatus and a method for providing healthcare information which can be utilized to administer and/or maintain financial accounts for, and/or on behalf of, any of the patients, users, providers, payers, and/or intermediaries, described herein.

It is another object of the present invention to provide an apparatus and a method for providing healthcare information which can provide for the security and/or the confidentiality of any data and/or information concerning patients, users, providers, payers, and/or intermediaries.

It is still another object of the present invention to provide an apparatus and a method for providing healthcare information which can be utilized in conjunction with identification cards which are utilized to store information regarding patients, providers, payers, users, and/or intermediaries.

It is yet another object of the present invention to provide an apparatus and a method for providing healthcare information which can be utilized in order to maintain patient healthcare records or files private and/or to safeguard patient healthcare records or files.

It is another object of the present invention to provide an apparatus and method for providing healthcare information which can provide notification to patients and individuals when others have accessed, obtained, and/or made changes to their respective healthcare records or files.

It is still another object of the present invention to provide an apparatus and method for providing healthcare information which can enable patients and individuals to restrict and/or limit access to their healthcare records or files.

It is yet another object of the present invention to provide an apparatus and a method for providing healthcare information which can be utilized in conjunction with intelligent agents, software agents, and/or mobile agents.

It is another object of the present invention to provide an apparatus and a method for providing healthcare information which can be programmed to be self-activating and/or activated automatically.

It is still another object of the present invention to provide an apparatus and a method for providing healthcare information which can be utilized to automatically generate and/or transmit any of the e-mails, electronic message transmissions, electronic notification transmissions, and/or any of the communications, described herein, between any of the parties which utilize the present invention.

It is yet another object of the present invention to provide an apparatus and a method for providing healthcare information which can be utilized in conjunction with various electronic commerce technologies and/or security methods, techniques and technologies.

It is another object of the present invention to provide an apparatus and method for providing healthcare information which can utilize electronic signatures and/or process electronic signatures and/or electronic signature information in performing any of the herein-described processing routines and/or functions.

Other objects and advantages of the present invention will be apparent to those skilled in the art upon a review of the Description of the Preferred Embodiment, taken in conjunction with the Drawings which follow.

DESCRIPTION OF THE PREFERRED EMBODIMENT

Figure 1:
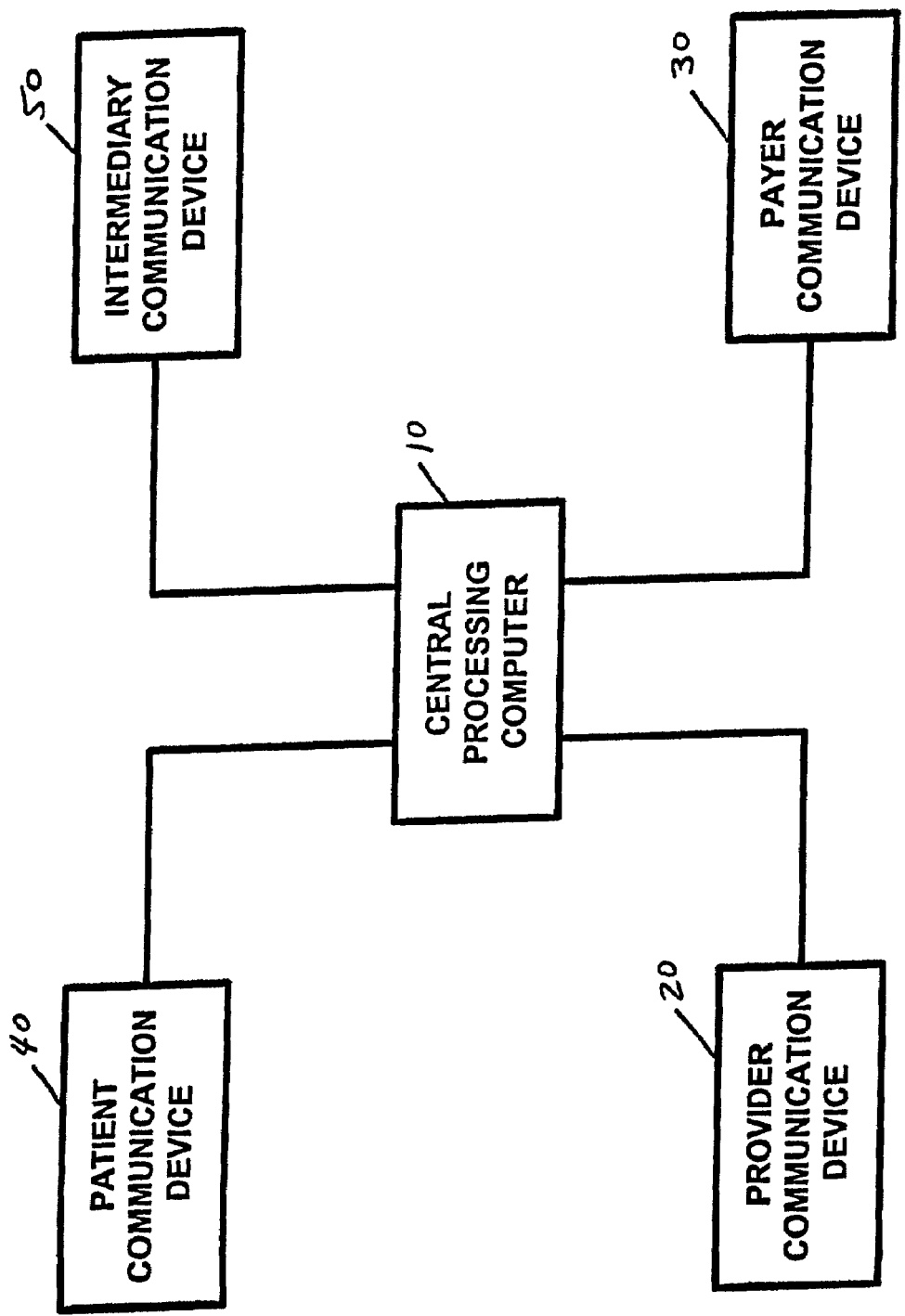
FIG. 1 illustrates a preferred embodiment of the present invention, in block diagram form.

The present invention is directed to an apparatus and a method for processing and/or for providing healthcare information and/or healthcare-related information and, in particular, to an apparatus and a method for processing and/or for providing healthcare information and/or healthcare-related information for a variety of healthcare and healthcare related applications.

The apparatus and method of the present invention facilitates the creation and management of a comprehensive healthcare processing system which can manage patient and client records, doctor and other provider records, healthcare insurance and/or payer records, and thereby provide an apparatus, system and methods for providing a variety and a multitude of healthcare information processing applications, processes and services.

The present invention facilitates improved healthcare quality, efficient information collection, processing and dissemination, efficient diagnosis and treatment, cost efficiency, cost containment, as well as many other benefits and advantages as will be described herein.

The apparatus and method of the present invention also facilitates the distribution and management of healthcare insurance, life insurance, disability insurance, as well as claims processing related thereto.

The present invention also provides an apparatus and a method for providing a comprehensive processing system which incorporates data and/or information from any combination and/or all of the participants in the healthcare field including, but not limited to, patients and those seeking healthcare, healthcare providers, doctors, including medical doctors, surgeons, physicians, dentists, psychologists, optometrists, podiatrists, osteopaths, chiropractors, pharmacists, therapists, physical therapists, respiratory therapists, nurses, healthcare aids, nutritionists, and/or any other person, individual and/or professional who can provide healthcare, healthcare-relate, wellness and/or wellness-related services and/or products, insurance companies, healthcare insurance companies, disability insurance companies, casualty insurance companies, health maintenance organizations, healthcare providers, and any other payer and/or provider of healthcare services and/or products, healthcare claims processing centers, healthcare insurance brokers and/or agents, and/or any other third party and/or intermediary who or which acts on behalf of another and/or assists in to providing of healthcare and/or related services.

The apparatus and method of the present invention can also be utilized in order to maintain patient healthcare records or files private, to safeguard patient healthcare records or files, to provide notification to patients and other individuals when others have accessed, obtained, and/or made changes to their respective healthcare records or files, and/or to enable patients and individuals to restrict and/or limit access to their healthcare records or files.

Applicant hereby incorporates by reference herein the subject matter and teachings of U.S. patent application Ser. No. 09/737,348 which teaches and discloses an apparatus and method for processing and/or for providing healthcare information and/or healthcare-related information. Applicant also hereby incorporates by reference herein the subject matter and teachings of U.S. Provisional Patent Application Ser. No. 60/286,422 which teaches and discloses an apparatus and method for processing and/or for providing healthcare information and/or healthcare-related information. Applicant also hereby incorporates by reference herein the subject matter and teachings of U.S. Provisional Patent Application Ser. No. 60/172,555 which teaches and discloses an apparatus and method for processing and/or for providing healthcare information and/or healthcare-related information.

Applicant also hereby incorporates by reference herein the subject matter of U.S. patent application Ser. No. 09/162,889 which teaches an apparatus and method for processing healthcare data. Applicant also hereby incorporates by reference herein the subject matter of U.S. Pat. No. 5,961,332 which teaches an apparatus for processing psychological data and method of use thereof.

As used herein, the terms "individual", "patient", "client", "user" or the like, or their plural forms, refers to any person, individual, patient, and/or client who uses the present invention, and/or who seeks and/or who receives healthcare services, healthcare-related services, healthcare-related information, and/or any of the other services and/or products provided by the present invention.

As used herein, the terms "doctor", "healthcare provider", "provider", "therapist", "healthcare information specialist", etc., or their plural forms, refers to any medical doctor, including any and all of the various medical specialists and/or specialties, including, but not limited to internists, orthopedists, opthamalogists, cardiologists, hematologists, endocrinologists, oncologists, ears, nose and throat specialists, neurologists, urologists, gastrointerologists, dermatologists, pediatricians, medical specialist, surgeon, surgical specialists, including any and/or forms and/or types of surgeons, physician, dentist, psychiatrist, psychologist, optometrist, podiatrist, osteopath, chiropractor, pharmacist, therapist, physical therapist, respiratory therapist, nurse, healthcare aid, nutritionist, and/or any other person, individual and/or professional who can provide healthcare, healthcare-relate, wellness and/or wellness-related services and/or products.

As used herein, the terms "insurer", "payer", "insurance provider", "heath insurance provider", "life insurance provider", "disability insurance provider", etc., or their plural forms, refers to any insurance companies, healthcare insurance companies, disability insurance companies, casualty insurance companies, health maintenance organizations, healthcare providers, and any other payer and/or provider of healthcare services and/or products, who which provide and/or pay for healthcare and/or healthcare-related benefits, services, and/or products, and/or who or which provide respective health insurance, life insurance and/or disability insurance benefits, services and/or products.

As used herein, the terms "broker", "agent", "billing service", "collection agent", "manager", intermediary", "assistant", etc., or their plural forms, refer to any broker, insurance broker, agent, insurance agent, intermediary, third party, billing service provider, collection agent, claim processing agent, and/or any other person, individual, and/or entity, which acts on behalf of, or for, any of the individuals, patients, doctors, healthcare providers, insurers, payers, etc., described herein.

FIG. 1 illustrates the apparatus of the present invention, in block diagram form. The apparatus of the present invention is denoted generally by the reference numeral 100. In the preferred embodiment, the apparatus 100 of the present invention includes a central processing computer or central processing computer system 10 (hereinafter referred to as the "central processing computer 10"). In the preferred embodiment the central processing computer 10 can be a network or server computer.

In the preferred embodiment, the central processing computer 10 can provide control over the apparatus 100 and can perform any of the various processing services and/or functions described herein. The central processing computer 10 may be a single computer or system of computers and/or may be include a plurality of computers or computer systems which are utilized in conjunction with one another. The central processing computer 10, in the preferred embodiment can provide services for any of the other computers and/or computer systems described herein as being associated with any of the individuals, patients, healthcare providers, insurers, payers, brokers, agents, and/or intermediaries, described herein.

The apparatus 100 also includes a healthcare provider communication device or computer 20 (hereinafter referred to as "provider communication device 20" or "provider computer 20") which is associated with a healthcare provider such as a healthcare professional, a hospital, a clinic, and/or any other provider of services described herein. Any number or amount of healthcare provider computers 20 can be utilized in conjunction with a healthcare provider and/or group of providers. The healthcare provider computer(s) 20 can communicate with, and operate in conjunction with, the central processing computer 10 and/or any of the other computers and/or computer systems associated with any of the other individuals and/or entities which utilize and/or operate in conjunction with the present invention.

The apparatus 100 can also include a healthcare payer communication device or computer 30 (hereinafter referred to as "payer communication device 30" or "payer computer 30") which is associated with a healthcare payer such as a healthcare insurer, insurance company, health maintenance organization, a clinic, and/or any other payer of healthcare services and products described herein. Any number or amount of healthcare payer computers 30 can be utilized in conjunction with a healthcare payer and/or group of payers. The healthcare payer computer(s) 30 can communicate with, and operate in conjunction with, the central processing computer 10 and/or any of the other computers and/or computer systems associated with any of the other individuals and/or entities which utilize and/or operate in conjunction with the present invention.

The apparatus 100 can also include a patient or individual user communication device or computer 40 (hereinafter "patient communication device 40" or "patient computer 40") which is associated with a healthcare patient such as a patient, user, or client who seeks or who is provided with healthcare and/or related services, products and/or related information. The patient communication device 40 can also be utilized by any individual, party, or entity, who or which may merely utilize the present invention in order to obtain information of interest.

A patient communication device 40 may also be located at public places or locations, such as at kiosks or other publicly available computer or communication devices. Any number or amount of patient computers 40 can be utilized in conjunction with a patient and/or group of patients. The patient computer(s) 40 can communicate with, and operate in conjunction with, the central processing computer 10 and/or any of the other computers and/or computer systems associated with any of the other individuals and/or entities which utilize and/ or operate in conjunction with the present invention. The patient computer(s) 40 can also be utilized by any other individual or entity desiring to utilize and/or to obtain information from the apparatus 100 and/or from any other the The apparatus 100 can also include an intermediary communication device or computer 50 (hereinafter referred to as "intermediary communication device 50" or "intermediary computer 50") which is associated with an intermediary, a broker, an agent, and/or any other individual and/or entity, that can utilize the present invention in order to act for and/or on behalf of any other individual, party, or entity, described herein. Any number or amount of intermediary computers 50 can be utilized in conjunction with an intermediary and/or group of intermediaries. The intermediary computer(s) 50 can communicate with, and operate in conjunction with, the central processing computer 10 and any of the other computers and/or computer systems associated with any of the other individuals and/or entities which utilize and/or operate in conjunction with the present invention.

In the preferred embodiment, any of the provider computer(s) 20, the payer computer(s) 30, the patient computer(s) 40, and/or the intermediary computer(s) 50, can be any computer or communication device, including, but not limited to, a personal computer, a home computer, a server computer, a network computer, a hand-held computer, a palmtop computer, a laptop computer, a personal communication device, a personal digital assistant, a telephone, a digital telephone, a television, an interactive television, a beeper, a pager, and/or a watch.

Each of the central processing computer(s) 10, the provider computer(s) 20, the payer computer(s) 30, the patient computer(s) 40, and/or the intermediary computer(s) 50, can transmit information to, as well as receive information from, any of the computers 10, 20, 30, 40, and 50, described herein. In this regard, each of the computers 10, 20, 30, 40, and 50, can communicate with, process information from, and/or share data and/or information with, each other and/or any other computer or computers 10, 20, 30, 40, and 50, described herein and/or utilized in conjunction with the present invention. In this manner, data and/or information transfer between any of the computers 10, 20, 30, 40, and 50, can communicate with any other computer or computers 10, 20, 30, 40, and 50, in a bi-directional manner.

The central processing computer(s) 10, the provider computer(s) 20, the payer computers(s) 30, the patient computer(s) 40, and the intermediary computer(s) 50, can communicate with one another, and/or be linked to one another, over a communication network, a telecommunication network, a telephone network, a line-connected network, and/or a wireless communication network. Each of the computers 10, 20, 30, 40, and 50, can be linked with any other computer or computers directly or indirectly directly or indirectly with one another so as to facilitate a direct or indirect bi-directional communication said respective computers.

In the preferred embodiment, the present invention is utilized on, and/or over, the Internet and/or the World Wide Web. The present invention, in the preferred embodiment, can also utilize wireless Internet and/or World Wide Web services, equipment and/or devices. The central processing computer(s) 10, in the preferred embodiment, has a web site or web sites associated therewith.

Although the Internet and/or the World Wide Web is a preferred communication system and/or medium utilized, the present invention, in all of the embodiments described herein, can also be utilized with any appropriate communication network or system including, but not limited to, a communication network or system, a telecommunication network or system, a telephone communication network or system, a cellular communication network or system, a wireless communication network or system, a line or wired communication network or system, a wireless Internet network or system, a wireless World Wide Web network or system, a digital communication network or system, a personal communication network or system, a personal communication services (PCS) network or system, a satellite communication network or system, a broad band communication network or system, a low earth orbiting (LEO) satellite network or system, a public switched telephone network or system, a telephone communication network or system, a radio communication network or system, and/or any other communication network or system, and/or any combination of the above communication networks or systems.

In the preferred embodiment, each of the central processing computer(s) 10, the provider computer(s) 20, the payer computer(s) 30, the patient computer(s) 40, and intermediary computer(s), can transmit data and/or information using TCP/IP, as well as any other Internet and/or World Wide Web, and/or communication, protocols.

The apparatus 100 of the present invention can utilize electronic commerce technologies and security methods, techniques and technologies, in any and/or all of the instances of data and/or information processing, and/or data and/or information transmission described herein.

Figure 2:
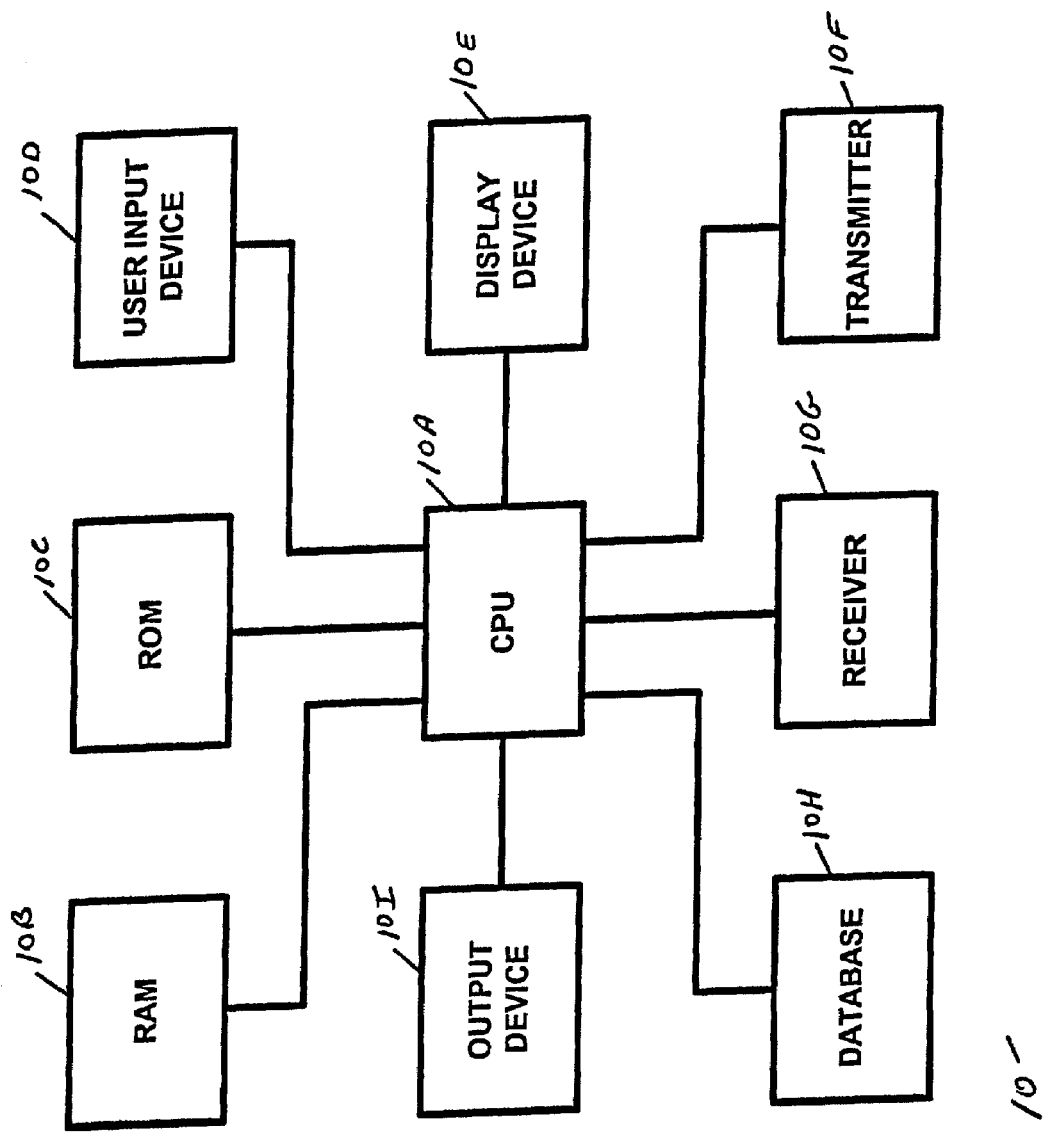
FIG. 2 illustrates the central processing computer of FIG. 1, in block diagram form.

FIG. 2 illustrates the central processing computer 10, in block diagram form. The central processing computer 10, in the preferred embodiment, is a network computer or computer system, or any other communication device which can provide the functionality of, and which can be utilized as a central processing computer such as an Internet server computer and/or a web site server computer. In the preferred embodiment, the central processing computer 10 includes a central processing unit or CPU 10A, which in the preferred embodiment, is a microprocessor. The CPU 10A may also be a microcomputer, a minicomputer, a macro-computer, and/or a mainframe computer, depending upon the application.

The central processing computer 10 also includes a random access memory device(s) 10B (RAM) and a read only memory device(s) 10C (ROM), each of which is connected to the CPU 10A, a user input device 10D, for entering data and/or commands into the central processing computer 10, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information, for example pulse rate monitors, blood pressure monitors, electrocardiograms, blood-sugars monitors, etc., if desired, which input device(s) are also connected to the CPU 10A. The central processing computer 10 also includes a display device 10E for displaying data and/or information to a user or operator.

The central processing computer 10 also includes a transmitter(s) 10F, for transmitting signals and/or data and/or information to any one or more of the central processing computer(s) 10, the provider computer(s) 20, the payer computers(s) 30, the patient computer(s) 40, and the intermediary computer(s) 50 individual computer(s), which may be utilized in conjunction with the present invention. The central processing computer 10 also includes a receiver 10G, for receiving signals and/or data and/or information from any one or more of the central processing computer(s) 10, the provider computer(s) 20, the payer computers(s) 30, the patient computer(s) 40, and the intermediary computer(s) 50, which may be utilized in conjunction with the present invention.

The central processing computer 10 also includes a database(s) 10H which contains data and/or information pertaining to the patients, providers, payers, and intermediaries who or which are serviced by the present invention and/or who or which utilize the present invention.

The database 10H can contain any and/or all of the information needed and/or required in order to perform any and/or all of the functions, services and/or operations described herein as being performed by the central processing computer 10 or the apparatus 100 of the present invention. In this regard the database 10H can contain data and/or information regarding patient name, patient identification information, patient social security number or other identification information, date of birth, doctors or providers, therapists, nutritionists, insurance or payer information, group insurance information, group health insurance information, life insurance information, disability insurance information, patient address, phone number, e-mail and/or other contact information, medical history, psychological history, dental history, family history, family medical, psychological, and/or dental history, insurance coverage, insurance co-payment and/or deductible information, insurance information, insurance claim procedures, insurance claim forms, doctor or provider appointment schedules, past treatments, past diagnosis, symptoms, insurance claim forms, employer information, lifestyle information, treatment plans, treatment progress, broker/agent/intermediary information, education information, age, sex, marital status, employee benefits information, types or services and/or treatments needed, and any other data and/or information regarding the patient which would be needed and/or desired in order to perform any and/or all of the functions, services and/or operations described herein.

The database(s) 10H can also contain healthcare and/or medical video, image, and/or audio, data and/or information, such as, for example, x-rays, Magnetic Resonant Images (MRI), CAT scans, digital x-ray files, digital Magnetic Resonant Imaging (MRI) files, digital CAT scan files, and/or any other video, imaging, and/or audio, healthcare data and/or information which can be utilized by healthcare providers, payers, intermediaries, patients, and/or other users of the present invention. In this manner, the present invention can facilitate the availability of any of the above-described video, image, and/or audio, data and/or information in a network environment. For example, a medical specialist can have access to, and/or review, an MRI or a CAT scan for a patient, from any location and at any time.

The database 10H can also contain data and/or information regarding providers including provider name, provider social security number or identification number, type of professional or service provider, address, phone number, fax number, e-mail and/or other contact information, experience, specialties, insurances accepted, schedule of charges, financial account identification information, resume information, education, work experience, claim forms, appointment schedules, procedures performed, and/or any other data and/or information concerning the providers for providing any and/or all of the functions, services, and/or operations described herein as being performed by the present invention.

The database 10H can also contain data and/or information regarding all possible fields of medicine, surgery, psychiatry, psychology, dentistry, oral surgery, optometry, podiatry, physical therapy, respiratory therapy, hypnosis, osteopathy, nutrition, wellness, and/or any other possible healthcare fields and/or subject matter which can possibly by utilized in the processing and/or operation of the present invention.

The database 10H can also contain information on illnesses, symptoms, diseases and/or sicknesses, theories, scientific theories, research data and/or information, diagnosis information, treatment information, treatment plans, treatment processes, treatment progresses, treatment interactions, side effects, expected treatment results, treatment providers, treatment durations, treatment costs, pre-treatment information, post-treatment information, treatment monitoring information, statistical information regarding diagnoses, treatments, treatment success rates, treatment failure rates, treatment centers, therapy plans, therapy success rates, therapy failure rates, treatment procedures, medications treatments, non-medication treatments, healthcare institutions, treatment evaluating criteria, treatment mistakes and/or mishaps, indicators of mistakes and/or mishaps, corrective actions, links to providers, links to treatment centers or institutions, reimbursement rates, nutrition information, diet information, exercise information, exercise routines, treatment options, healthcare advise, wellness advice, preventive care, preventive procedure, health maintenance, drug and medication information, drug interaction information, video information, including video files or clips and other information, regarding illnesses, diseases, treatments and follow-up care, audio information, including audio files or clips and other information, regarding illnesses, diseases, treatments and follow-up care, treatment and/or procedure information and/or narratives, treatment analysis, diagnosis analysis, diagnosis monitoring, diagnosis confirmation and/or checking, and/or other information for providing the herein-described functions, services, and/or operations.

The database 10H can also contain information regarding the insurance companies and payers described herein, including, but not limited to, payer name, address, phone number, fax number, e-mail address, identification number(s), coverage types, policies and/or coverages provided, reimbursement rates, patients and/or providers serviced and/or covered by the payer, policy information, claim forms, claim procedures, claim status, claim processing information, claim submission procedures and policies, reasonable and customary charges, co-payment information, pre-approval information and/or procedures, claim form information, electronic form claim forms, insurance and/or coverage requirements, guidelines, and/or triggering events, covered procedures and/or treatments, uncovered procedures and/or treatments, claim approval information, claim approval history, claim approval statistics, claim rejection or denial information, claim rejection or denial history, claim rejection or denial statistics, financial account information, network provider information, network patient information, claim statistics, preventative care and/or benefits information, benefits information, benefits request information and/or claim forms, claim submission information, claim processing information, claim status information, payment information and statistics, and/or any other data and/or information regarding and/or related to payers which are needed and/or desired for providing any and/or all of the functions, services, and/or operations described herein.

The database 10H can also contain data and/or information regarding the brokers, agents and/or intermediaries described herein, including, but not limited to, intermediary name, address, phone number, fax number, e-mail address, clients, patients services, insurance policies, policy information, policy quote information, policy proposal information, any and/or all of the above information described herein regarding patients, providers, payers, etc. which may be of interest to the intermediaries described herein which may be useful and/or beneficial to the intermediaries in providing any of the functions, services, and/or operation described herein.

The database 10H can also contain contact information such as phone numbers, fax numbers, pager numbers, beeper numbers, e-mail addresses, hyperlinks to, and/or any other information which can facilitate contact between any of the parties described herein. The database 10H also includes electronic signature data and/or information for any of the parties, patients, providers, payers, and/or intermediaries, described herein for facilitating transactions, claim submissions, financial transactions, etc., by and/or between any of the above patients, providers, payers, and/or intermediaries.

The data and/or information in the database 10H can also include links to any other information, information sources, news sources, and/or other information and/or data which can or may be utilized by the present invention and/or by any of the patients, providers, payers, intermediaries and/or any other users of the present invention.

The database 10H can also contain data and/or information regarding healthcare news, healthcare developments, healthcare discoveries, etc., for and including the medical field, surgical field, psychological field, dental field, nutrition field, fitness field, etc., and/or any other healthcare field or fields.

The database 10H, in the preferred embodiment, can also contain video and/or audio files which can be utilized for training of healthcare professionals as well as for providing general information to any user of the present invention. In this manner, and as will be described hereinbelow, the apparatus 100 can be utilized as a simulator for providing training in medical diagnosing, medical training, surgical training, psychiatric training, psychological training, dental training, oral surgery training, therapist training, and/or for training any of the healthcare providers described herein and/or envisioned.

For example, the present invention can be utilized to provide a medical doctor with a set of symptoms, evaluate the diagnosis and treatment prescribed and provide follow-up patient conditions which may or may not call for the medical doctor to re-evaluate his or her diagnosis and/or treatment. In a similar fashion, the present invention can be used for training and continuing education and training for any of the healthcare providers described herein and/or otherwise envisioned utilizing the present invention.

The database 10H can also contain data and/or information restricting access by any of the providers, payers, patients, intermediaries, and/or other users, to any of the data and/or information stored in the database 10H.

The database 10H can also contain information correlating symptoms and/or conditions with diagnoses, prognoses, and/or treatments, treatment methods, procedures, etc. The database 10H also contains any and/or all information needed and/or desired for facilitating the processing of symptoms, conditions, medical histories, family histories, and other information, in order to arrive at diagnoses and/or prognoses, treatments, prescriptions, procedures and/or any other healthcare and/or healthcare-related information.

The database 10H can also contain statistical and/or other probabilistic and/or mathematical information for assigning and/or correlating certain levels and/or estimates for any and/or all of the information, diagnoses, prognoses, treatments, procedures, and/or any other information processed and/or generated by the central processing computer 10 and/or the apparatus 100. Applicant hereby incorporates by reference herein the teachings of *Basic Business Statistics Concepts and Applications*, Mark L. Berenson and David M. Levine, $6^{th}$ Edition, Prentice Hall 1996.

The database 10H, in the preferred embodiment, can be a database which may include individual databases or collections of databases, with each database being designated to store any and all of the data and/or information described herein. The database 10H, or collection of databases, may be updated by each of the respective patients, providers, payers, users, and/or intermediaries, and/or by any other third party, in real-time, and/or via dynamically linked database management techniques.

The data and/or information stored in the database 10H can also be updated by and/or dynamically linked to, various external sources, including but not limited to news services, research publications, research facilities, healthcare laboratories, providers of healthcare goods and/or services, pharmaceutical companies, research institutions, schools. The database 10H will contain any and all information deemed necessary and/or desirable for providing all of the processing and/or services and/or functions described herein. Applicant hereby incorporates by reference herein the subject matter of *Fundamentals of Database Systems*, by Ramez Elmasri and Shamkant B. Navathe, $2^{nd}$ Ed., Addison-Wesley Publishing Company, 1994.

The data and/or information which is contained and/or stored in the database 10, as well as any of the other databases 20H, 30H, 40, and 50H, described herein can be obtained from the various patients, individuals, providers, payers, and/or intermediaries, who or which utilize and/or who or which are serviced by the present invention. For example, the respective patients, providers, payers, intermediaries, and/or other users, could fill out questionnaires, forms, narratives, claim forms, and/or any other information medium, in written form, electronically, and/or otherwise.

Data and/or information stored in the database 10H as well as any of the other databases described herein can be updated by multiple parties. For example, a patient may provide medical history for his or her individual file, his or her medical doctor can update the medical history information for the patient upon examining and/or treating him or her. The payer may also update the file with any associated payment or payment-related information. Should the patient go to another doctor or different type of doctor, all previous information would be available for, and can be updateable by, the next doctor.

The database 10H can also contain information regarding alternate medicine techniques, herbal techniques, meditation techniques, exercise techniques, self healing, faith healing, and/or other non-medicine treatments and/or techniques.

The database 10H can also include statistical data and/or information regarding diagnoses, and/or alternate diagnoses, treatment success, treatment failure, as well as statistical data and/or information regarding misdiagnoses. The database 10H also contains data and/or information regarding experimental treatments as well as statistical information regarding same, successes of same and failures of same.

In any and/or all of the embodiments described herein, any of the data and/or information which is or which may be stored in the database 10H, and/or any of the other databases described herein, can be utilized and/or can appear in any of the reports, diagnostic reports, treatment reports, evaluation reports, provider reports, payer reports, patient reports, training reports, and/or any other reports, described herein.

The central processing computer 10 also includes an output device 10I for output any data, information, report, etc., described herein. In the preferred embodiment, the output device 10I can be a printer, a display, a transmitter, a modem, and/or any other device which can be used to output data.

Any of the data and/or information for any of the patients, individuals, providers, payers, and/or intermediaries, can be updated by different parities and which such updated data and/or information being made available to other respective parties so as to provide and ensure comprehensive and up-to-date healthcare and healthcare-related information.

Figure 3:
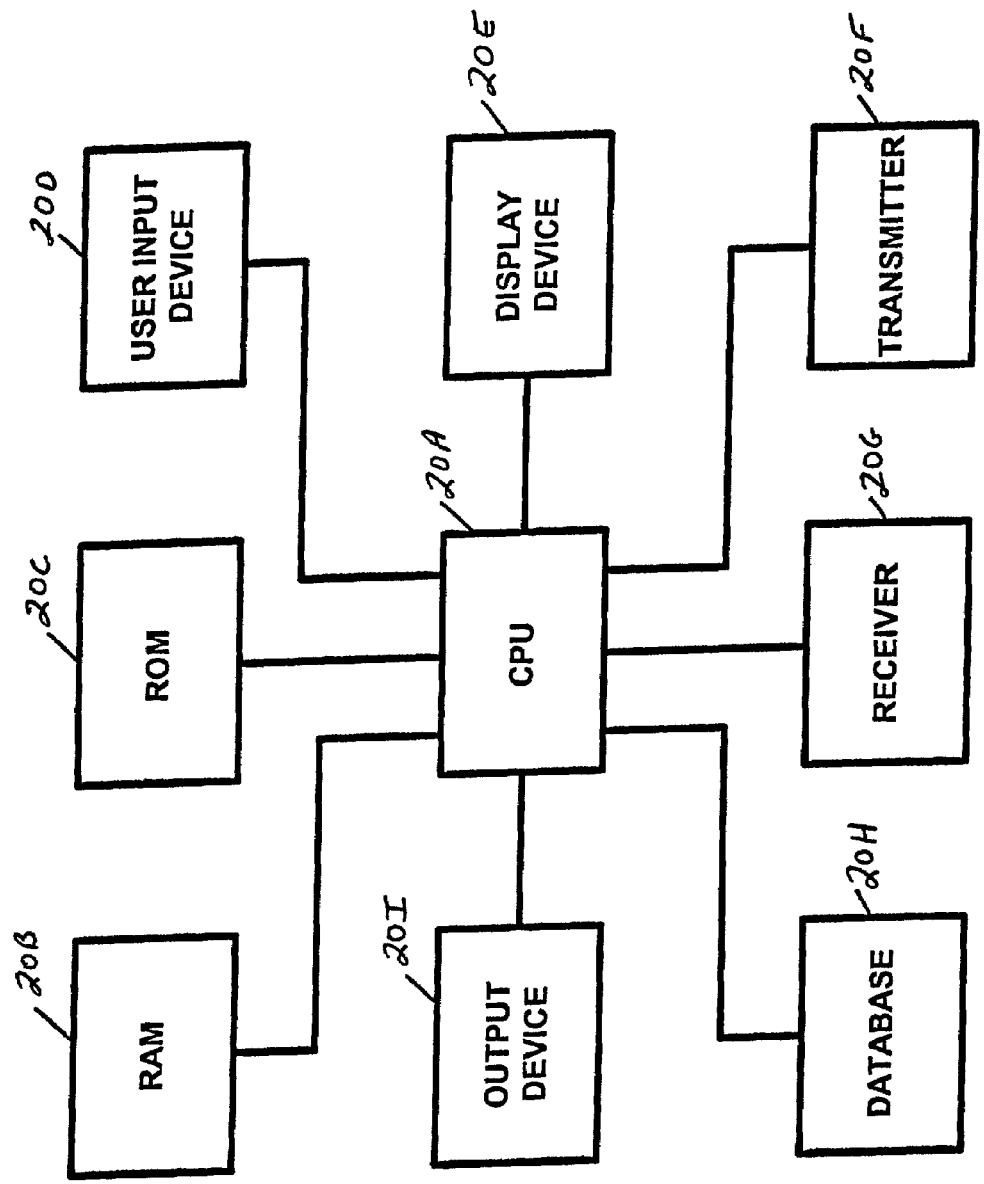
FIG. 3 illustrates the provider communication device of FIG. 1, in block diagram form.

FIG. 3 illustrates the provider communication device 20, in block diagram form. The provider communication device 20, in the preferred embodiment, can be personal computer, a network computer or computer system, or any other computer or communication device, which is utilized as a provider computer 20. In the preferred embodiment, the provider communication device 20 includes a central processing unit or CPU 20A, which in the preferred embodiment, is a microprocessor. The CPU 20A may also be a microcomputer, a mini-computer, a macro-computer, and/or a mainframe computer, depending upon the application.

The provider communication device 20 also includes a random access memory device(s) 20B (RAM) and a read only memory device(s) 20C (ROM), each of which is connected to the CPU 20A, a user input device 20D, for entering data and/or commands into the provider communication device 20, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information, for example pulse rate monitors, blood pressure monitors, electrocardiograms, blood-sugars monitors, etc., if desired, which input device(s) are also connected to the CPU 20A.

The user input device 20D can also acquire, receive, generate and/or provide, data which can be entered by a user or individual and/or can be a device which can acquire, receive, generate and/or provide, digital data such as medical, healthcare, bio-metric, physiological, and/or any other kind of healthcare data and/or healthcare-related data. For example, a user input device 20D can be a keyboard for allowing a user to input information into the provider communication device and/or a user input device can, for example, by a heart rate monitor or EKG machine which can receive information from a patient or individual and generate a digital signal, digital data, analog data, and/or any other signal, data, and/or information, which is representative of the patient's or individual's heart rate, pulse rate, and/or cardiac activity.

The user input device 20D can also be, or can include, any one or more of, and/or any combination of, a thermometer, a digital thermometer, a stethoscope, a heart rate monitor or measurement device, a pulse rate monitor or measurement device, a blood pressure monitor or measurement device, a blood pressure measurement device, blood analysis device or machine, a respirator, a respiration monitoring or measurement device, a dialysis machine, a dialysis device, electrocardiograph (EKG) machine or device, electrocephalograph (EEG) machine or device, electromyograph (EMG) machine or device, a magnetic resonance imaging (MRI) machine or device, X-ray machine or device, medical imaging machine or device, thermal imaging machine or device, a heart sound monitor or measurement device, a lung sound monitoring or measurement device, respiration rate monitoring or measurement device, a laprascopic device, an arthroscopic device, a vascular testing device, a catheter device, a cardiac performance testing, monitoring, or measurement device, a pulmonary performance testing, monitoring, or measurement device, a vascular system performance monitoring or measurement device, a vascular system testing, monitoring, or measurement device, a metabolism monitoring or measurement device, a sonogram imaging device, a sonogram measurement device, a sonograph device, an optical response device, an optical response measurement device, an intravenous device, an arterial blood pressure measurement or monitoring device, a respiration rate measurement or monitoring device, an ultrasound imaging device, an ultrasound measurement device, a CAT SCAN device, an optical metabolism measurement or monitoring device, a radiotelemetric device, a doppler medical device, a mammogram device, a carbon dioxide detection or measurement device, a carbon monoxide detection or measurement device, a transvascular impedance measurement or monitoring device, an ultrasonic imaging device, a bone conduction device, a brain function scan analyzer device, external pulse cardiac monitoring or measurement device, a fetal heart rate measurement, monitoring, or probing, device, an endotrachial cardiac monitoring device, a finger tip blood pressure monitoring device, a psychological monitoring device, a surgical instrument, a vital signs measurement device, ear pressure regulating device, phonocardiograph device, acoustic aneurysm detector device, blood oxygen detection device, esophageal probing device, ultrasonic probing device, ausculoscope, vital signs monitoring system, heart activity monitoring device, pulmonary activity monitoring device, sphygmomanometer, esophageal stethoscope, venous pressure measuring device, differential doppler device, physiological data measuring device, body tissue movement device, breathalyzer device, camera probing device, microscopic camera probing device, and/or any other bio-metric or physiological data measuring device(s) and/or data acquisition device (hereinafter referred to generally or collectively as "healthcare equipment input device", "healthcare measurement input device", or "healthcare monitoring input device").

The provider communication device 20 also includes a display device 20E for displaying data and/or information to a user or operator.

The provider communication device 20 also includes a transmitter(s) 20F, for transmitting signals and/or data and/or information to any one or more of the central processing computer(s) 10, the provider computer(s) 20, the payer computers(s) 30, the patient computer(s) 40, and the intermediary computer(s) 50 individual computer(s), which may be utilized in conjunction with the present invention. The provider communication device 20 also includes a receiver 20G, for receiving signals and/or data and/or information from any one or more of the central processing computer(s) 10, the provider computer(s) 20, the payer computers(s) 30, the patient computer(s) 40, and the intermediary computer(s) 50, which may be utilized in conjunction with the present invention.

The provider communication device 20 also includes a database(s) 20H. The database 20H can contain and/or be linked to any of the data and/or information described herein as being stored in the database 10H.

The provider communication device 20 also includes an output device 20I for output any data, information, report, etc., described herein. In the preferred embodiment, the output device 20I can be a printer, a display, a transmitter, a modem, and/or any other device which can be used to output data.

Figure 4:
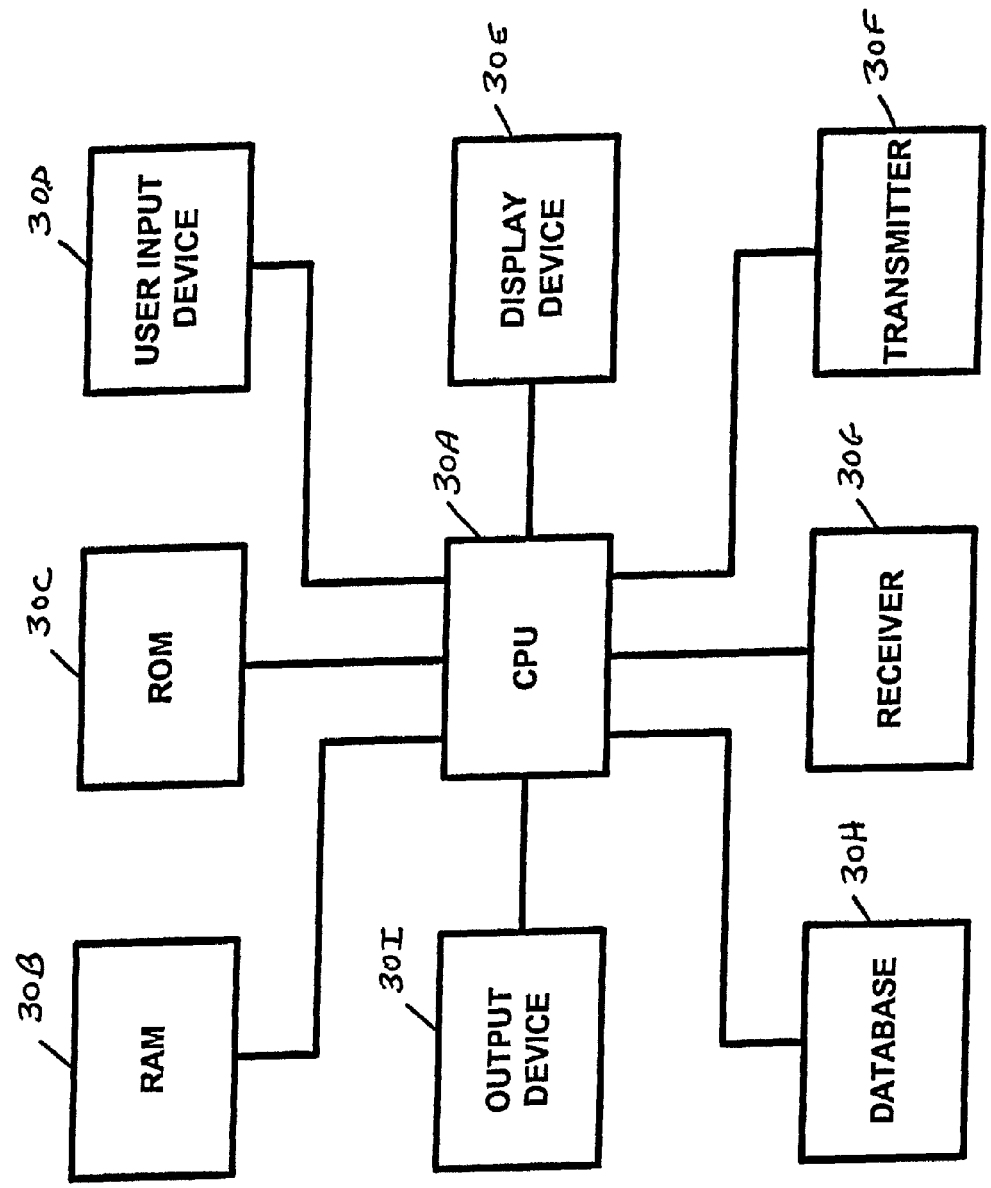
FIG. 4 illustrates the payer communication of FIG. 1, in block diagram form.

FIG. 4 illustrates the payer communication device 30, in block diagram form. The payer communication device 30, in the preferred embodiment, can be personal computer, a network computer or computer system, or any other computer or communication device, which is utilized as a payer computer 30. In the preferred embodiment, the payer communication device 30 includes a central processing unit or CPU 30A, which in the preferred embodiment, is a microprocessor. The CPU 30A may also be a microcomputer, a minicomputer, a macro-computer, and/or a mainframe computer, depending upon the application.

The payer communication device 30 also includes a random access memory device(s) 30B (RAM) and a read only memory device(s) 30C (ROM), each of which is connected to the CPU 30A, a user input device 30D, for entering data and/or commands into the payer communication device 30, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information, for example pulse rate monitors, blood pressure monitors, electrocardiograms, blood-sugars monitors, etc., if desired, which input device(s) are also connected to the CPU 30A. The payer communication device 30 also includes a display device 30E for displaying data and/or information to a user or operator.

The payer communication device 30 also includes a transmitter(s) 30F, for transmitting signals and/or data and/or information to any one or more of the central processing computer(s) 10, the provider computer(s) 20, the payer computers(s) 30, the patient computer(s) 40, and the intermediary computer(s) 50 individual computer(s), which may be utilized in conjunction with the present invention. The payer communication device 30 also includes a receiver 30G, for receiving signals and/or data and/or information from any one or more of the central processing computer(s) 10, the provider computer(s) 20, the payer computers(s) 30, the patient computer(s) 40, and the intermediary computer(s) 50, which may be utilized in conjunction with the present invention.

The payer communication device 30 also includes a database(s) 30H. The database 30H can contain and/or be linked to any of the data and/or information described herein as being stored in the database 10H.

The payer communication device 30 also includes an output device 30I for output any data, information, report, etc., described herein. In the preferred embodiment, the output device 30I can be a printer, a display, a transmitter, a modem, and/or any other device which can be used to output data.

Figure 5:
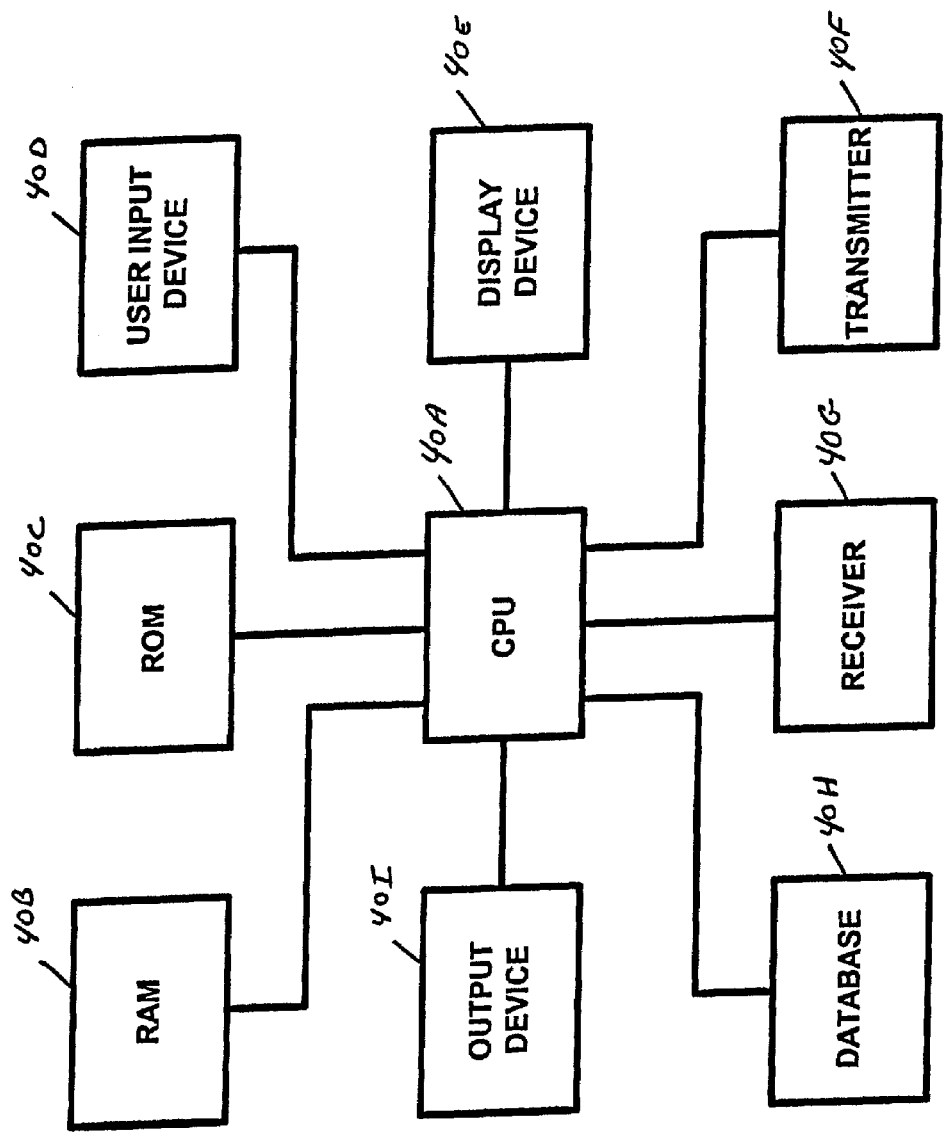
FIG. 5 illustrates the patient communication device of FIG. 1, in block diagram form.

FIG. 5 illustrates the patient communication device 40, in block diagram form. The patient communication device 40, in the preferred embodiment, can be personal computer, a network computer or computer system, or any other computer or communication device, which is utilized as a patient computer. In the preferred embodiment, the patient communication device 40 includes a central processing unit or CPU 40A, which in the preferred embodiment, is a microprocessor. The CPU 40A may also be a microcomputer, a minicomputer, a macro-computer, and/or a mainframe computer, depending upon the application.

The patient communication device 40 also includes a random access memory device(s) 40B (RAM) and a read only memory device(s) 40C (ROM), each of which is connected to the CPU 40A, a user input device 40D, for entering data and/or commands into the patient communication device 40, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information, for example pulse rate monitors, blood pressure monitors, electrocardiograms, blood-sugars monitors, etc., if desired, which input device(s) are also connected to the CPU 40A.

The user input device 40D can also acquire, receive, generate and/or provide, data which can be entered by a user or individual and/or can be a device which can acquire, receive, generate and/or provide, digital data such as medical, healthcare, bio-metric, physiological, and/or any other kind of healthcare data and/or healthcare-related data. For example, a user input device 20D can be a keyboard for allowing a user to input information into the patient communication device and/ or a user input device can, for example, by a heart rate monitor or EKG machine which can receive information from a patient or individual and generate a digital signal, digital data, analog data, and/or any other signal, data, and/or information, which is representative of the patient's or individual's heart rate, pulse rate, and/or cardiac activity.

The user input device 40D can also be, or can include, any one or more of, and/or any combination of, a thermometer, a digital thermometer, a stethoscope, a heart rate monitor or measurement device, a pulse rate monitor or measurement device, a blood pressure monitor or measurement device, a blood pressure measurement device, a blood analysis device or machine, a respirator, a respiration monitoring or measurement device, a dialysis machine, a dialysis device, electrocardiograph (EKG) machine or device, electrocephalograph (EEG) machine or device, electromyograph (EMG) machine or device, a magnetic resonance imaging (MRI) machine or device, X-ray machine or device, medical imaging machine or device, thermal imaging machine or device, a heart sound monitor or measurement device, a lung sound monitoring or measurement device, respiration rate monitoring or measurement device, a laprascopic device, an arthroscopic device, a vascular testing device, a catheter device, a cardiac performance testing, monitoring, or measurement device, a pulmonary performance testing, monitoring, or measurement device, a vascular system performance monitoring or measurement device, a vascular system testing, monitoring, or measurement device, a metabolism monitoring or measurement device, a sonogram imaging device, a sonogram measurement device, a sonograph device, an optical response device, an optical response measurement device, an intravenous device, an arterial blood pressure measurement or monitoring device, a respiration rate measurement or monitoring device, an ultrasound imaging device, an ultrasound measurement device, a CAT SCAN device, an optical metabolism measurement or monitoring device, a radiotelemetric device, a doppler medical device, a mammogram device, a carbon dioxide detection or measurement device, a carbon monoxide detection or measurement device, a transvascular impedance measurement or monitoring device, an ultrasonic imaging device, a bone conduction device, a brain function scan analyzer device, external pulse cardiac monitoring or measurement device, a fetal heart rate measurement, monitoring, or probing, device, an endotrachial cardiac monitoring device, a finger tip blood pressure monitoring device, a psychological monitoring device, a surgical instrument, a vital signs measurement device, ear pressure regulating device, phonocardiograph device, acoustic aneurysm detector device, blood oxygen detection device, esophageal probing device, ultrasonic probing device, ausculoscope, vital signs monitoring system, heart activity monitoring device, pulmonary activity monitoring device, sphygmomanometer, esophageal stethoscope, venous pressure measuring device, differential doppler device, physiological data measuring device, body tissue movement device, breathalyzer device, camera probing device, microscopic camera probing device, and/or any other bio-metric or physiological data measuring device(s) and/or data acquisition device data acquisition device (hereinafter referred to generally or collectively as "healthcare equipment input device", "healthcare measurement input device", or "healthcare monitoring input device").

The patient communication device 20 also includes a display device 40E for displaying data and/or information to a user or operator.

The patient communication device 40 also includes a transmitter(s) 40F, for transmitting signals and/or data and/or information to any one or more of the central processing computer(s) 10, the provider computer(s) 20, the payer computers(s) 30, the patient computer(s) 40, and the intermediary computer(s) 50 individual computer(s), which may be utilized in conjunction with the present invention. The patient communication device 40 also includes a receiver 40G, for receiving signals and/or data and/or information from any one or more of the central processing computer(s) 10, the provider computer(s) 20, the payer computers(s) 30, the patient computer(s) 40, and the intermediary computer(s) 50, which may be utilized in conjunction with the present invention.

The patient communication device 40 also includes a database(s) 40H. The database 40H can contain and/or be linked to any of the data and/or information described herein as being stored in the database 10H.

The patient communication device 40 also includes an output device 40I for output any data, information, report, etc., described herein. In the preferred embodiment, the output device 40I can be a printer, a display, a transmitter, a modem, and/or any other device which can be used to output data.

Figure 6:
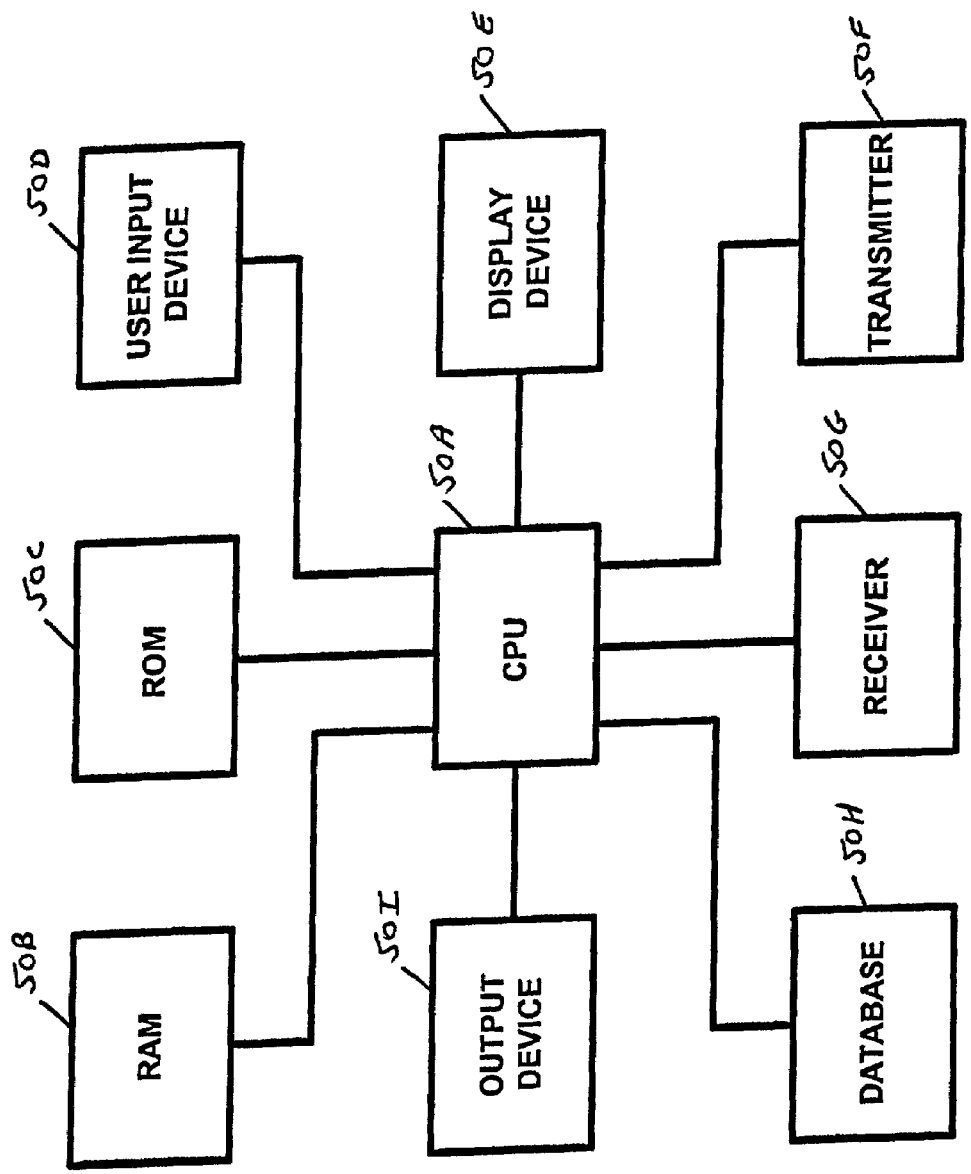
FIG. 6 illustrates the intermediary communication device of FIG. 1, in block diagram form.

FIG. 6 illustrates the intermediary computer 50, in block diagram form. The intermediary computer 50, in the preferred embodiment, can be personal computer, a network computer or computer system, or any other computer or communication device, which is utilized as an intermediary computer 50. In the preferred embodiment, the intermediary computer 50 includes a central processing unit or CPU 50A, which in the preferred embodiment, is a microprocessor. The CPU 50A may also be a microcomputer, a minicomputer, a macrocomputer, and/or a mainframe computer, depending upon the application.

The intermediary computer 50 also includes a random access memory device(s) 50B (RAM) and a read only memory device(s) 50C (ROM), each of which is connected to the CPU 50A, a user input device 50D, for entering data and/or commands into the intermediary computer 50, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information, for example pulse rate monitors, blood pressure monitors, electrocardiograms, blood-sugars monitors, etc., if desired, which input device(s) are also connected to the CPU 50A. The intermediary computer 50 also includes a display device 50E for displaying data and/or information to a user or operator.

The intermediary computer 50 also includes a transmitter(s) 50F, for transmitting signals and/or data and/or information to any one or more of the central processing computer(s) 10, the provider computer(s) 20, the payer computers(s) 30, the patient computer(s) 40, and the intermediary computer(s) 50 individual computer(s), which may be utilized in conjunction with the present invention. The intermediary computer 50 also includes a receiver 50G, for receiving signals and/or data and/or information from any one or more of the central processing computer(s) 10, the provider computer(s) 20, the payer computers(s) 30, the patient computer(s) 40, and the intermediary computer(s) 50, which may be utilized in conjunction with the present invention.

The provider communication device 50 also includes a database(s) 50H. The database 50H can contain and/or be linked to any of the data and/or information described herein as being stored in the database 10H.

The intermediary communication device 50 also includes an output device 50I for output any data, information, report, etc., described herein. In the preferred embodiment, the output device 50I can be a printer, a display, a transmitter, a modem, and/or any other device which can be used to output data.

In any and/or all of the embodiments described herein, any one of the central processing computers 10, the provider communication devices 20, the payer communication devices 30, the patient communication devices 40, and/or the intermediary communication devices 50, can include input devices (not shown) for facilitating the data entry of a patients vital signs and or other medical data such as, but not limited to, pulse rate, blood pressure, blood-sugar level, etc., and any other data and or information which can be input into the respective computer and/or communication device and be transmitted to the central processing computer consistent with the utilization of the present invention as described herein.

The apparatus and method of the present invention can be utilized in numerous preferred embodiments in order to provide a vast array of healthcare and healthcare-related services for any one or more of the various parties described herein. While certain of the preferred embodiments may be described with regards to utilization by a particular party, it is important to note that any patient, user, provider, payer, and/or intermediary may utilize the present invention in the same, similar and/or analogous manner. For example, a preferred embodiment for determining and/or ascertaining a medical diagnosis can be described as being utilized by a treating physician as well as be utilized by a provider to verify and/or check a diagnosis as well as by a patient or other user or individual in order to perform a self-diagnosis or double check a doctors diagnosis. In the same manner, any other preferred embodiment and/or other uses of the present invention can be utilized by any of the parties described herein.

The present invention, in its various preferred embodiments can be utilized to create and maintain comprehensive patient databases which can be accessed via a network environment and/or otherwise, to perform healthcare and/or healthcare-related diagnoses, to provide healthcare and/or healthcare-related expected prognoses, to provide healthcare and/or healthcare-related treatment plans or programs, and/or to provide healthcare and/or healthcare-related treatment progress reports and/or evaluations.

The present invention can also be utilized in order to provide training and continuing education services for healthcare and/or healthcare-related professionals, to provide healthcare, healthcare-related, and/or wellness information, to provide information about healthcare and/or healthcare-related patient, providers, payers, and/or intermediaries, to provide scheduling management services for providers, to provide notification services for patients, providers, payers and/or intermediaries and/or any other parties described herein, and/or to locate providers, payers and/or intermediaries.

The present invention can also be utilized, in preferred embodiments, in order to healthcare and/or healthcare-related claim processing services, claims submissions, claim processing, claim status checking, and claim reconciliation, claim fraud prevention, treatment evaluation, healthcare and/or healthcare insurance policy generation, management and administration, provider, payer and/or intermediary evaluation, drug and/or treatment interactivity, treatment, medication and/or organ availability and/or notification services, patient, provider, payer, intermediary, and/or third party, notification services.

The present invention can also be utilized as a clearinghouse for facilitating the offering, selling, buying, trading, and/or other commerce and/or transactions, involving healthcare and/or healthcare-related services, products and/or goods.

In any and/or all of the embodiments described herein, the various computers and/or communication devices 10, 20, 30, 40 and/or 50, can be utilized to transmit and/or to receive transmissions, information, messages, and/or notification messages and/or signals to, and/or between, the respective parties associated with the respective computers and/or communication devices. The transmission of information, messages, and/or notification messages and/or signals, in any and/or all of the embodiments described herein can be effected via any one or more of e-mail messages, telephone messages, beeper or pager messages, physical mail delivery, electronic data transmission, and/or can be made via any other suitable and/or appropriate communication method and/or technique.

Figure 7A:
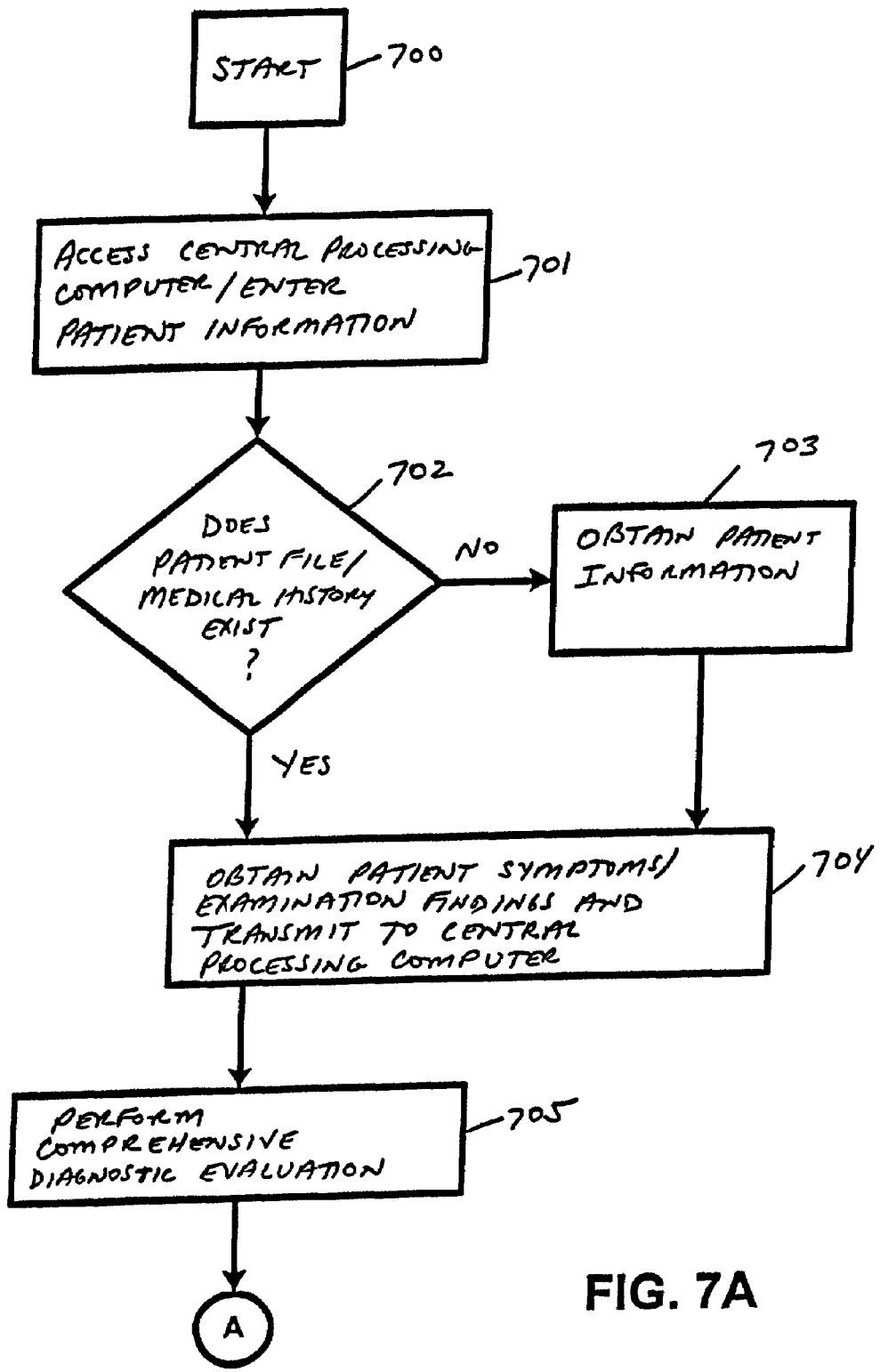
FIGS. 7A and 7B illustrate a preferred embodiment method of using the present invention, in flow diagram form.
Figure 7B:
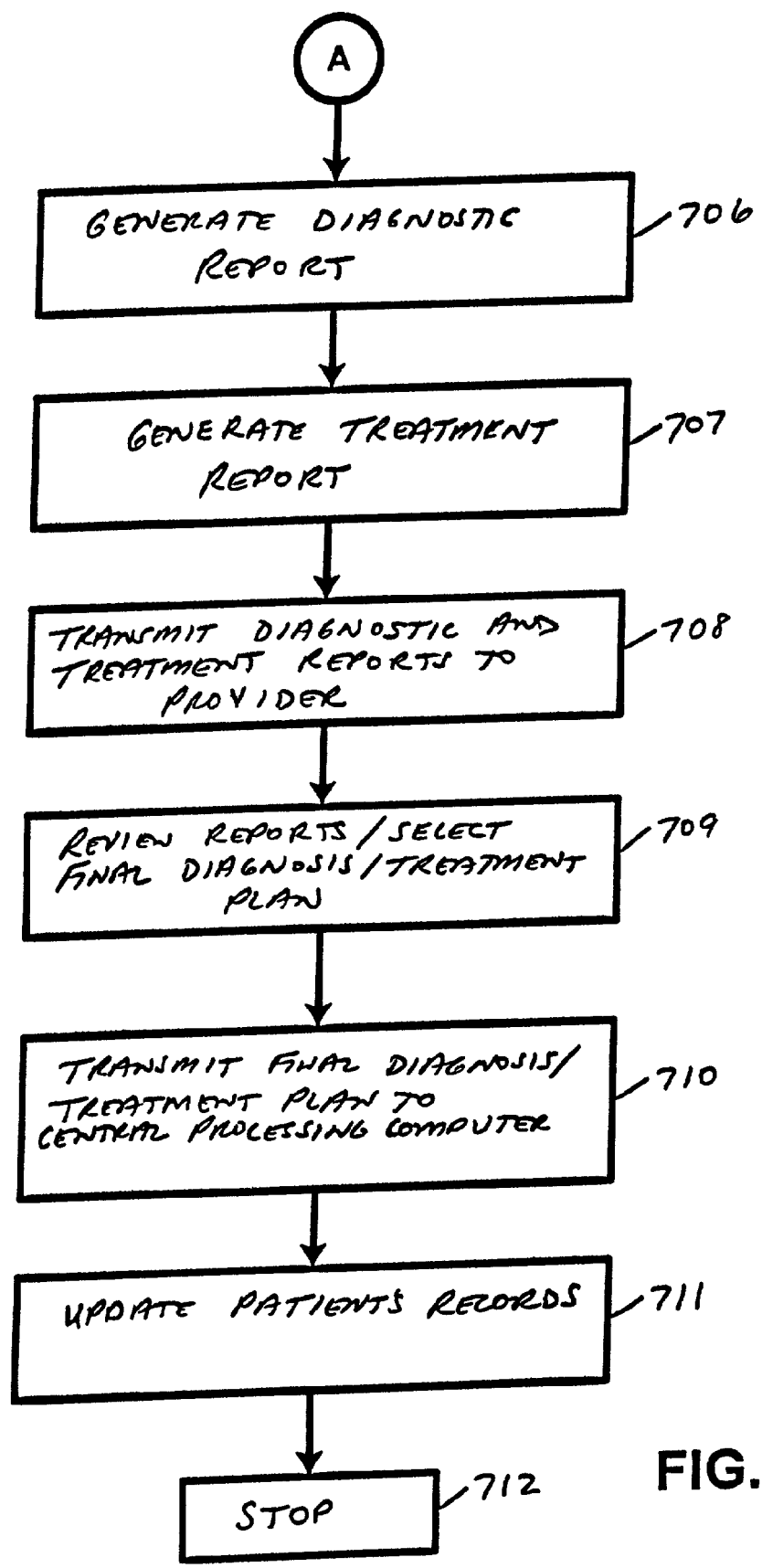

In a preferred embodiment, the present invention can be utilized in order to perform a diagnosis of a sickness, illness and/or other condition. FIGS. 7A and 7B illustrate a preferred embodiment method of using the present invention, in block diagram form. While the method of FIGS. 7A and 7B is described in the context of a medical doctor performing a diagnosis of a medical condition, the method of FIGS. 7A and 7B can be similarly utilized by surgeons, psychologists, psychiatrists, dentists, and/or any other healthcare provider or healthcare professional described herein. The method of FIGS. 7A and 7B may also be utilized by any user, patient, provider, payer, and/or intermediary in order to ascertain a diagnosis and/or in order to check on, verify, and/or ascertain the correctness of a diagnosis of another.

The operation of the apparatus 100 commences at step 700. At step 701, the provider can access the central processing computer 10 and enter data and/or information regarding the patient. At step 702, the central processing computer 10 will determine if a file and/or medical history exists for the patient. If, at step 702, it is determined that a medical history does not exist, the central processing computer 10 will, at step 703, request that a medical history, family history and/or other information related thereto be provided by the patient or accompanying individual. At step 703, the information provided by the patient or accompanying individual will then be entered via the provider communication device 20 and transmitted to, and be stored at, the central processing computer 10. Thereafter, processing will proceed to step 704.

If, at step 702, it is determined that a patient's medical history does in fact exist, the processing will proceed to step 704. At step 704, the patient's symptoms, if any, and/or examination findings, are obtained from the patient and are transmitted from the provider communication device 20 to the central processing computer 10.

At step 704, data and/or information which can be obtained via any of the herein-described healthcare equipment input devices 20D, healthcare measurement input devices 20D, or healthcare monitoring input devices 20D, can also be transmitted to the central processing computer 10. The data and/or information obtained via any of the described healthcare equipment input devices 20D, healthcare measurement input devices 20D, or healthcare monitoring input devices 20D, can be transmitted from the provider communication device 20 to the central processing computer 10.

In this manner, the data and/or information which is transmitted to the central processing computer 10, at step 704, can include provider or user entered data and/or information, which can be entered via the user input device 20D such as a keyboard, a mouse, a cardreader, or other input device which can be utilized in conjunction with a computer or a communication device, and/or can include data and/or information which can be obtained and/or acquired by any of the herein-described healthcare equipment input devices 20D, healthcare measurement input devices 20D, or healthcare monitoring input devices 20D.

In a preferred embodiment, both provider or user entered data and/or information obtained and/or acquired by any of the herein-described healthcare equipment input devices 20D, healthcare measurement input devices 20D, or healthcare monitoring input devices 20D, can be utilized in performing a patient diagnosis. In another preferred embodiment, only data and/or information obtained and/or acquired by any of the herein-described healthcare equipment input devices 20D, healthcare measurement input devices 20D, or healthcare monitoring input devices 20D, can be utilized in performing a patient diagnosis. In another preferred embodiment, only provider or user entered data and/or information can be utilized in performing a patient diagnosis.

The central processing computer 10 will, at step 705 receive and process the patient symptoms, if any, examination findings, and/or any other data and/or information, in conjunction with the patient's medical history and/or other information, medical theories, principles, criteria and/or other medical information needed to make a diagnosis. At step 705, the central processing computer 10 will perform a comprehensive diagnostic evaluation of the patient's symptoms, if any, and/or the examination findings.

As described above, the diagnostic evaluation or diagnosis can be based upon both provider or user entered data and/or information and data and/or information obtained or acquired by any of the herein-described healthcare equipment input devices 20D, healthcare measurement input devices 20D, or healthcare monitoring input devices 20D, can be based upon only data and/or information obtained and/or acquired by any of the herein-described healthcare equipment input devices 20D, healthcare measurement input devices 20D, or healthcare monitoring input devices 20D, or can be based upon only provider or user entered data and/or information.

For example, a provider can enter patient symptom information along with patient data obtained from any of the herein-described healthcare equipment input devices 20D, healthcare measurement input devices 20D, or healthcare monitoring input devices 20D. A diagnosis can, thereafter, be processed utilizing data obtained from both the provider and any of the herein-described healthcare equipment input devices 20D, healthcare measurement input devices 20D, or healthcare monitoring input devices 20D.

Patient data can also be obtained solely from any of the herein-described healthcare equipment input devices 20D, healthcare measurement input devices 20D, or healthcare monitoring input devices 20D, with such patient data being utilized in order to arrive at a diagnosis. Patient data, in another preferred embodiment, can also be obtained solely from a provider or the patient himself or herself. A patient can also utilized the apparatus in conjunction with home healthcare equipment input devices, healthcare measurement input devices, or healthcare monitoring input devices.

At step 706, the central processing computer 10 will generate a diagnostic report which can include a diagnosis of the patient's condition, if needed. The diagnostic report which is generated at step 706 can, if needed, include a single diagnosis and/or a list of possible diagnoses, along with their respective probabilities of occurrence and/or statistical information corresponding thereto, which may pertain to the patient's condition. At step 707, the central processing computer 10 will then generate a treatment report which will outline and/or prescribe treatment for the single diagnosis and/or for the list of possible diagnoses, if any. The central processing computer 10, when generating the treatment report, can process same in conjunction with, and consider, possible drug interactions and/or treatment interactions.

At step 708, the central processing computer 10 will transmit the diagnostic report and/or treatment report to the provider's communication device 20 at which point the medical doctor can obtain the diagnosis or possible diagnoses, if any, and corresponding treatment plans. The medical doctor can then, at step 709, review the diagnostic report and/or treatment report and choose a final diagnosis and/or treatment plan, if needed, to administer to the patient.

At step 710, the medical doctor will transmit the final diagnosis and treatment plan, including the prescribed treatment and/or treatment plan, if any, to the central processing computer 10. At step 711, the central processing computer 10 will then update the patient's records in the database 10H so as to include all of the data and information described as being processed and/or generated by the central processing computer 10, including, but not limited to the patient's symptoms, if any, the examination findings, the information contained in the diagnostic report and the treatment report, the final diagnosis and the prescribed treatment.

Thereafter, operation of the apparatus 100 will cease at step 712. The patient's records will then be updated and be available for the patient's next treatment and/or diagnosis.

In another preferred embodiment, the diagnostic report and/or treatment reports can be accompanied by medical information, textbook materials, laboratory materials, reference materials, video clips of any pertinent information, audio clips of any pertinent information, hyperlinks to informational sources, information regarding providers and/or facilities for obtaining treatment and/or therapy, provider and/or facility contact information, and/or any other pertinent and/or relevant information.

In another preferred embodiment, the diagnostic report and/or treatment reports can be accompanied by health and/or wellness information which can include suggestions for health and/or wellness foods, goods, products, and/or services. The diagnostic report and/or treatment reports can also be accompanied by health and/or fitness information, diets, nutritional information, and/or any other information which may be of assistance to the patient and/or provider. The diagnostic and/or treatment reports can also contain warnings regarding misdiagnoses, warnings about treatments, information about experimental treatments, etc. The diagnostic and/or treatment reports can also contain information, statistical and/or otherwise, regarding diagnoses, misdiagnoses, treatment successes, and/or treatment failures. The diagnostic and/or treatment reports can also contain information regarding alternate medicine such as treatments regarding herbal remedies and/or treatments, meditation, self-healing, faith healing, yoga, tai chi, exercise therapy, and/or other therapies and/or therapy types.

As noted above, the method of utilizing the present invention, as described in FIGS. 7A and 7B, is equally applicable to, and can be utilized in the same manner, by any and/or all of the respective healthcare providers, professionals, and/or related providers. The apparatus of FIGS. 7A and 7B can also be utilized in a same or similar manner by any of the herein-described users, patients, healthcare providers, or healthcare payers.

The apparatus of FIGS. 7A and 7B can also utilize electronic signatures and/or process electronic signatures and/or electronic signature information which can correspond to any of the herein-described parties in performing any of the herein-described processing routines and/or functions.

In another preferred embodiment, the apparatus and method of the present invention can be utilized to ensure that a proper treatment and/or procedure is performed on the patient. Referring once again to FIGS. 7A and 7B and the above description of same, the present invention can be utilized to ensure that a subsequent treatment and/or treatments are performed as prescribed. As noted above with reference to FIG. 6 and, in particular, a final diagnosis and prescribed treatment is stored in the patient's file or records in the database 10H of the central processing computer.

When the patient seeks treatment from a subsequent medical doctor, surgeon, or other healthcare professional, the medical doctor, surgeon, or other healthcare professional, can access the central processing computer 10 at the time of treatment, access the patient's medical history and prescribed treatment plan and assess same in order to make sure that the treatment to be provided is called for in the prescribed treatment. In this manner, the present invention can be utilized in order to prevent medical and/or surgical mistakes, mishaps and/or other instances when improper treatment could occur.

It is also envisioned that the subsequent care medical doctor, surgeon, or other healthcare professional, could also re-evaluate the patient's condition and/or records and seek additional assistance and/or perform a separate and independent assessment and/or diagnosis of the patient. In any event, the present invention can provide the subsequent care medical doctor, surgeon, or other healthcare professional, with the patient's complete medical history, information, past diagnoses and/or past treatments and/or prescriptions. In this manner, a subsequent care provider can be provided with as complete and as up to date information as possible in order to administer treatment.

For example, the present invention can be utilized in the following manner. A patient scheduled for surgery on a certain body part (i.e. left ankle) may enter the hospital. Due to a hospital clerical error, the right ankle is noted to be operated on.

Prior to the surgery, the surgeon may access the central processing computer 10, via a provider communication device 20 located in the operating room, and/or another location in the hospital, in order to verify the procedure to be performed. In response thereto, the central processing computer 10 will transmit a message that it is the left ankle which is to be operated on. Thereafter, the surgeon can investigate the situation and ensure that the correct and prescribed surgery and/or procedure is performed. Once the surgery is completed, the patient's record will be updated accordingly. While a surgical procedure is described, it is important to note that any treatment, procedure, etc., which can be performed by any healthcare professional described herein, and/or in any healthcare field described herein, can be verified in the above-described manner. In this manner, the present invention can be utilized to pre-screen subsequent and/or follow-up treatments and/or procedures so as to prevent healthcare mistakes and/or mishaps.

The embodiment of FIGS. 7A and 7B can perform diagnoses by utilizing entered data and/or information and/or data and/or information which can be obtained by, acquired by, and/or measured by, any of the herein-described user input devices 20D.

In another preferred embodiment, the healthcare professional can access the central processing computer 10 via the provider communication device 20, access the patient's or client's record and input information concerning the treatment and/or procedure to be performed. Thereafter, the central processing computer 10 can process the information and transmit a message to the healthcare professional notifying the healthcare professional that the treatment and/or procedure is either the prescribed treatment or procedure or that it is not the prescribed treatment and/or procedure. The message provided by the central processing computer, to the treating healthcare professional, can also include information regarding the treatment and/or the procedure, such as instructions, steps, and/or any other accompanying information.

In any and/or all of the embodiments described herein, the central processing computer 10, in performing any processing of patient information, diagnosis information, and/or treatment information, described herein, can perform such processing in conjunction with drug and/or other treatment interaction information so as to provide an added safeguard in the diagnosis and treatment planning processes. Any and/or all processing described herein is also performed in conjunction with each patient's medical history, family history, allergic conditions information, and/or with any other information deemed important and/or essential in the individual's healthcare diagnoses and/or treatments.

In another preferred embodiment, the present invention can be utilized to perform treatment evaluations and/or treatment monitoring. In this manner, the present invention can be utilized by any of the providers, payers, patients, users, and/or intermediaries, described herein to evaluate and/or monitor treatments, provide training and/or oversight for healthcare providers and/or professionals, and/or allow payer and/or insurance companies to evaluate treatments, treatment plans, treatment progress, and/or any other evaluations and/or verifications for healthcare claims processing. In this embodiment, the present invention can be utilized so as to safeguard against the use of incorrect and/or unconventional and/or fraudulent treatment and/or care.

Figure 8A:
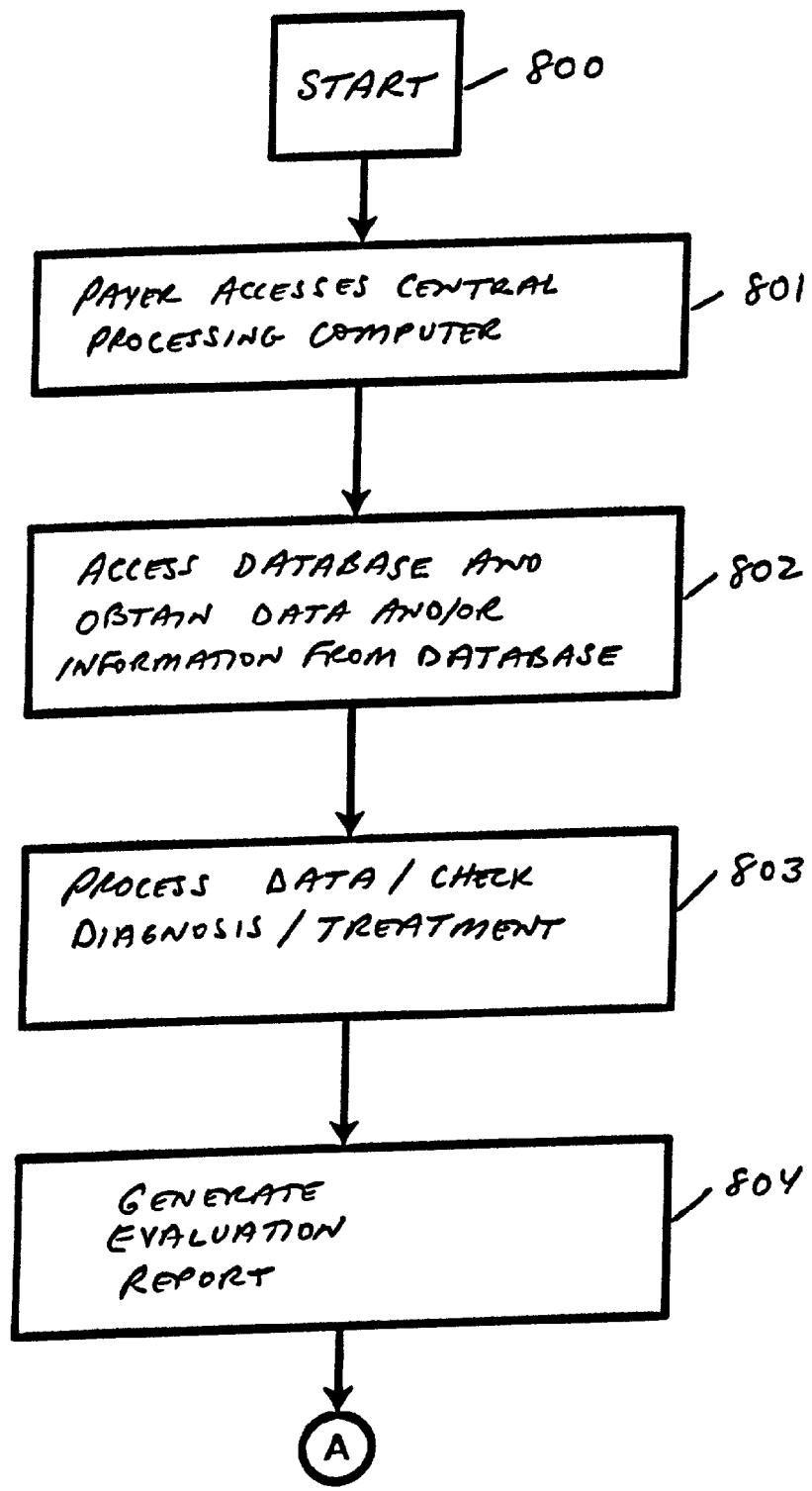
FIGS. 8A and 8B illustrate another preferred embodiment method of using the present invention, in flow diagram form.
Figure 8B:
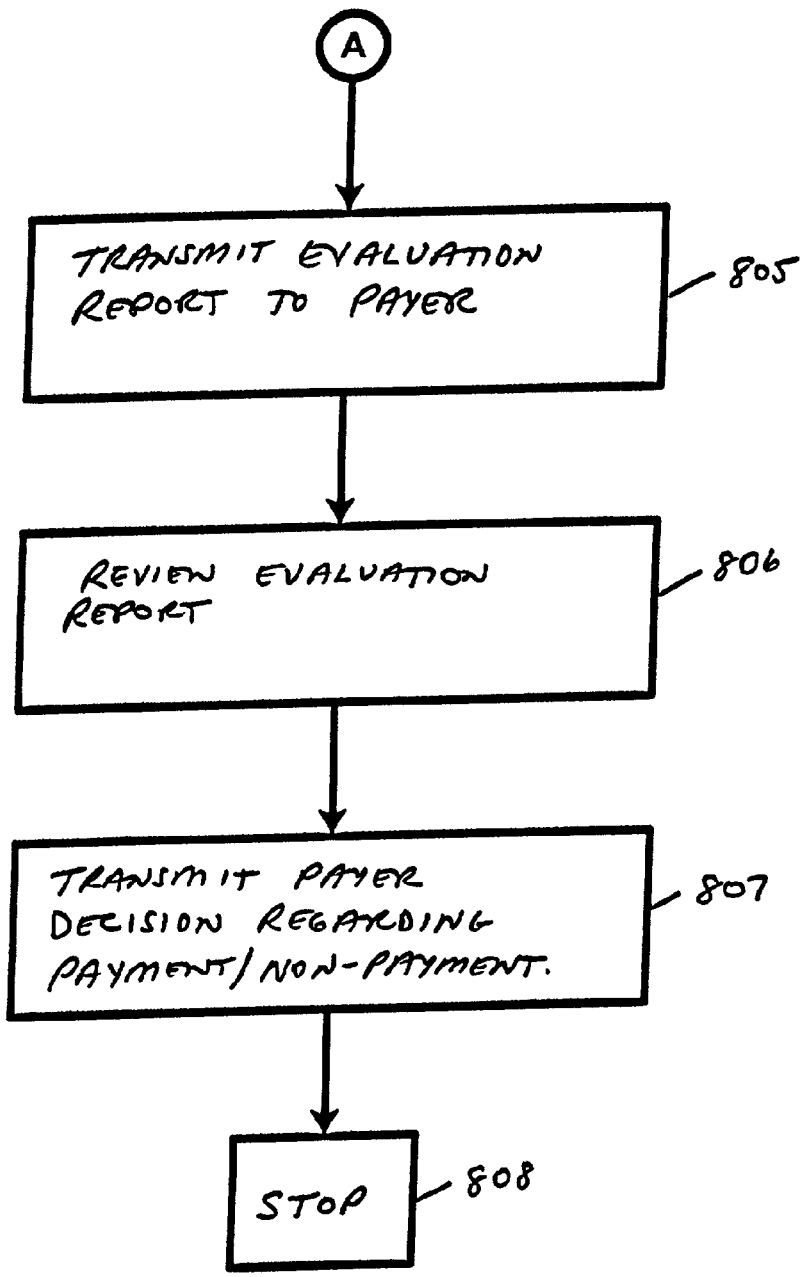

FIGS. 8A and 8B illustrate another preferred embodiment of a method of use of the present invention, in flow diagram form. FIGS. 8A and 8B illustrate a preferred embodiment method of use of the present invention in order to evaluate and/or monitor treatments, treatment plans and/or the administration of healthcare. While described as being utilized by payers and/or an insurance company in evaluating and/or monitoring treatment, it is important to note that the embodiment of FIGS. 8A and 8B can be utilized by any provider, patient, user, including healthcare students and/or healthcare professionals-in-training, or other providers, and/or intermediary, for obtaining the information provided by the embodiment of FIGS. 8A and 8B and utilizing it any manner they see fit.

With reference to FIGS. 8A and 8B, the operation of the apparatus 100 commences at step 800. At step 801, the payer or payer's employee or agent (hereinafter, for simplicity, referred to at payer's employee) can access the central processing computer 10. At step the payer's employee can enter information concerning the patient, the treatment, and/or care, which is desired to be evaluated and/or monitored.

At step 802, the central processing computer 10 will access the database 10H and obtain patient information, patient medical history, family history, if pertinent, symptom information, provider information, diagnostic report information, treatment report information, final diagnoses information, prescribed treatment information, and/or any other information which can be relevant and/or pertinent. Any and/or all of the information described above can be stored in the database 10H from prior processing and/or use of the present invention. Other data and/or information can also be obtained from the payer's employee and/or from other third party and/or outside sources.

At step 803, the central processing computer 10 will perform a processing routine in conjunction with the above-described information in order to determine if the diagnoses and associated and/or related treatment or treatments are appropriate and/or in-line with current standards for the given healthcare field. The central processing computer 10 can also calculate and/or provide statistical information regarding any of diagnoses and/or treatments under study. At step 804, the central processing computer 10 will generate an evaluation report which will provide data and information regarding the information obtained from step 803.

The central processing computer 10 can then, at step 805, transmit the evaluation report and/or any other appropriate information, to the payer communication device 30. The central processing computer, in another preferred embodiment, can, at step 803 and/or at step 804, determine and/or provide, as part of the evaluation report, information concerning whether the diagnoses and/or treatments are considered appropriate and/or valid, and/or in-line with standards, as well as recommend that claims for the treatment(s) are valid and should be paid by the payer, and/or that the claims for the treatment(s) are invalid and should be denied.

Thereafter, at step 806, the payer or the payer's employee can review the evaluation report and take any action deemed appropriate. At step 807, the payer or payer's employee can transmit data and/or information regarding the payer's or payer employee's action and/or decision. Step 807 is an optional step and can be dispensed with if the payer or payer's employee chooses not to respond to and/or to transmit information to, the central processing computer 10. Thereafter, the operation of the apparatus will cease at step 808.

The apparatus of FIGS. 8A and 8B can also utilize electronic signatures and/or process electronic signatures and/or electronic signature information which can correspond to any of the herein-described parties in performing any of the herein-described processing routines and/or functions.

The present invention when utilized as described in FIGS. 8A and 8B, can provide treatment evaluation and/or monitoring for healthcare payers which can be utilized for performing claims processing, provider evaluations, patient evaluations, and/or any other useful and/or desired purpose. The present invention, when utilized as described in FIGS. 8A and 8B, can also be utilized by any provider, patient, payer, user, and/or intermediary, to evaluate and/or monitor treatments, evaluate providers, evaluate patients, evaluate payers, ascertain payers claims paying and/or processing traits, and/or for educational purposes and/or for any other useful and/or desired purpose.

Figure 9A:
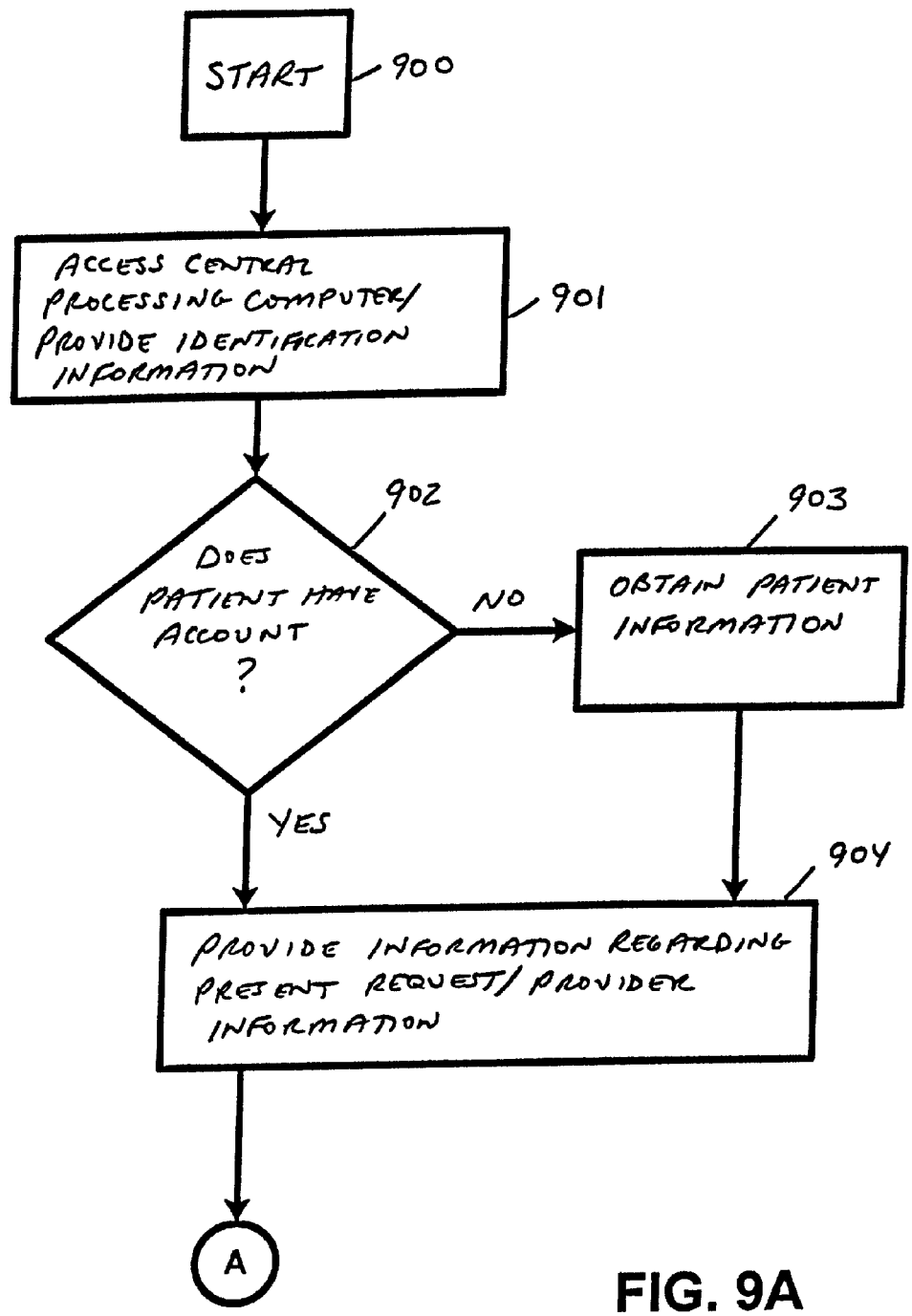
FIGS. 9A and 9B illustrate still another preferred embodiment method of using the present invention, in flow diagram form.
Figure 9B:
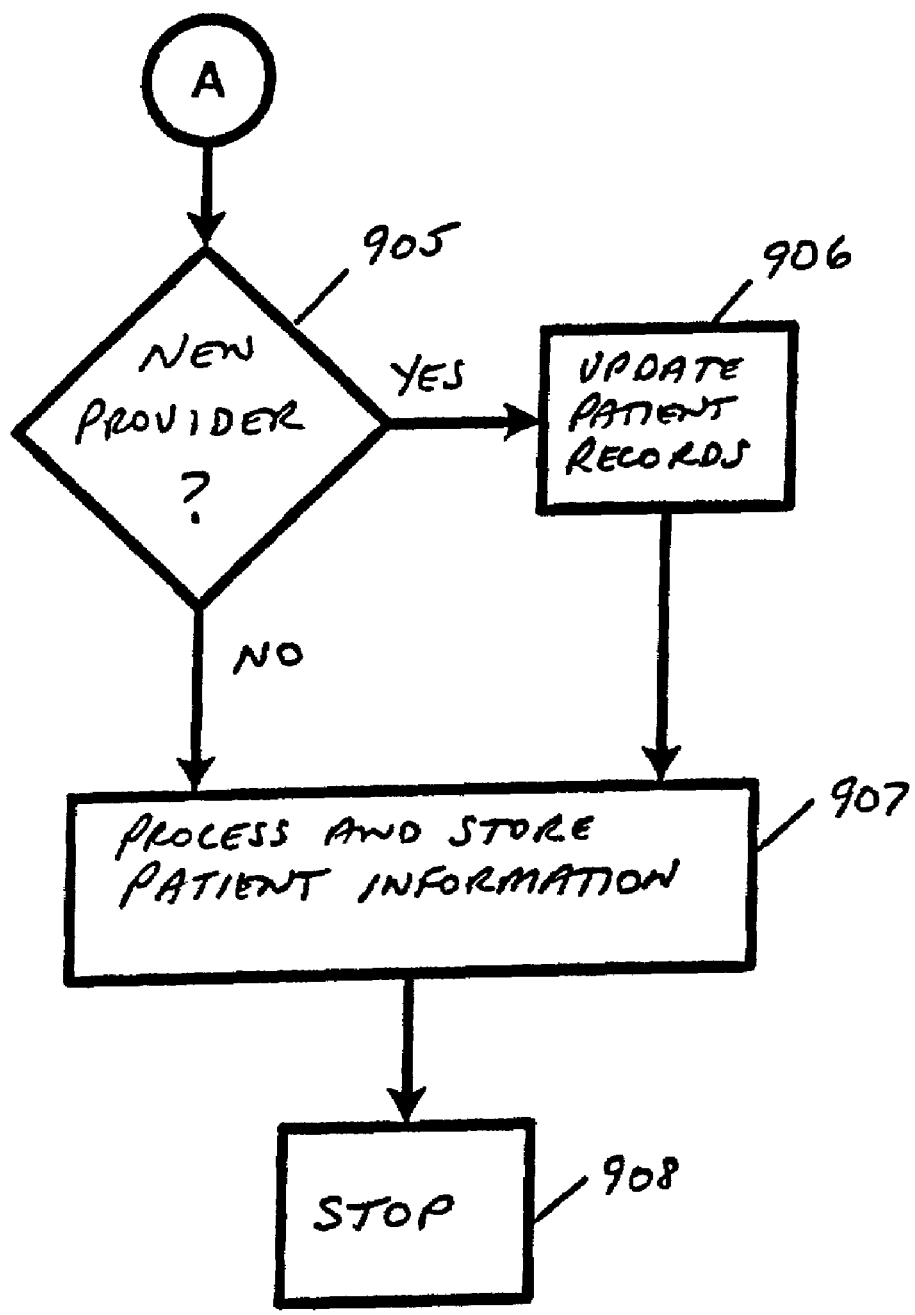

In another preferred embodiment of the present invention, the apparatus and method of the present invention can be utilized to create and maintain a comprehensive patient healthcare database. FIGS. 9A and 9B illustrate another preferred embodiment use of the present invention, in flow diagram form. With reference to FIGS. 9A and 9B, the operation of the apparatus 100 commences at step 900.

At step 901, the patient will access the central processing computer 10 and provide identification information. At step 902, the central processing computer 10 will determine whether the patient has an account and/or a file with the central processing computer and/or the service utilizing same. If, at step 902, it is determined that the patient does not have an account with the central processing computer 10, the processing will proceed to step 903 and patient will be prompted and/or asked to fill out any necessary forms and/or answer questions so as to provide a comprehensive medical history and family history, if possible.

All provided data and/or information will be stored in the database 10H and a patient account, file and/or record will be created at step 903. Thereafter, processing will proceed to step 904. If, at step 902, the patient is determined to have an account with the central processing computer, processing will proceed directly to step 904.

At step 904, the patient will provide information concerning the present healthcare request and present provider information. At step 905, the central processing computer 10, will then determine if the present provider is a new provider. If, at step 905, it is determined that the present provider is a new provider, the central processing computer 10 will proceed to step 906 and update the patient's files or records so as to include the present provider as a new provider for the patient. Thereafter, the central processing computer 10 will proceed to step 907 and will process and store, in the database 10H and/or in the patient's files or records, any pertinent patient information, symptoms, diagnoses and/or treatments, final diagnosis and/or prescribed treatment, for the provider visit or for the event or occurrence.

If, however, at step 905, it is determined that the present provider is an existing provider for the patient, the central processing computer 10 will proceed directly to step 907 and process and store, in the database 10H and/or in the patient's files or records, any pertinent patient information, symptoms, diagnoses and/or treatments, final diagnosis and/or prescribed treatment, for the provider visit or for the event or occurrence. Thereafter, operation of the present invention will cease at step 908.

The apparatus of FIGS. 9A and 9B can also utilize electronic signatures and/or process electronic signatures and/or electronic signature information which can correspond to any of the herein-described parties in performing any of the herein-described processing routines and/or functions.

In this manner, the present invention can be utilized so as to create and maintain a comprehensive healthcare patient database which can be accessed by any provider, payer, intermediary, and/or other party or user, in order to access the patient's healthcare files and/or records. The comprehensive database, which in the preferred embodiment of the present invention, is stored and/or maintained in the database 10H of the central processing computer 10, can contain and/or store any of the data and/or information obtained from, and/or provided by, any and/or all of the herein-described embodiments of the present invention.

The comprehensive database provides a data and/or information source which can be accessed by any provider, from anywhere in the world, and at any time, in order to obtain information about a patient in his, her, or its care. For example, a patient traveling far from home and out of reach by his or her current healthcare provider can be treated by another provider who can access the central processing computer 10, from any location, and at any time, and obtain up-to-date and/or comprehensive patient healthcare and/or medical and family history information, current healthcare and/or medical condition, current treatment and/or care and/or any other information which can facilitate optimal healthcare and/or medical treatment.

In the same manner, new providers can obtain existing information concerning healthcare and/or medical history, family history, current healthcare conditions and/or treatments as well as any other information from the central processing computer 10 thereby allowing the new provider to obtain accurate information and dispensing with the need to obtain same form the patient. The information provided from the present invention can also assist the provider in diagnosing the patient. Providers can also utilize the comprehensive database in order to ascertain past and/or current providers who may be contacted for assistance and/or for insight in the treatment process.

In a similar manner, payers can utilize the comprehensive database in order to ascertain payer eligibility, the existence of pre-existing conditions and/or to obtain any other useful information.

In another preferred embodiment, the present invention can be utilized in order to find and/or to locate providers and/or payers of, and for, respectively, various healthcare treatments, healthcare services and/or healthcare goods or products and/or healthcare-related goods or products. Information regarding the various providers and/or payers, along with information regarding the services and/or goods or products they provide and/or pay for, respectively, is stored in the database 10H.

Figure 10:
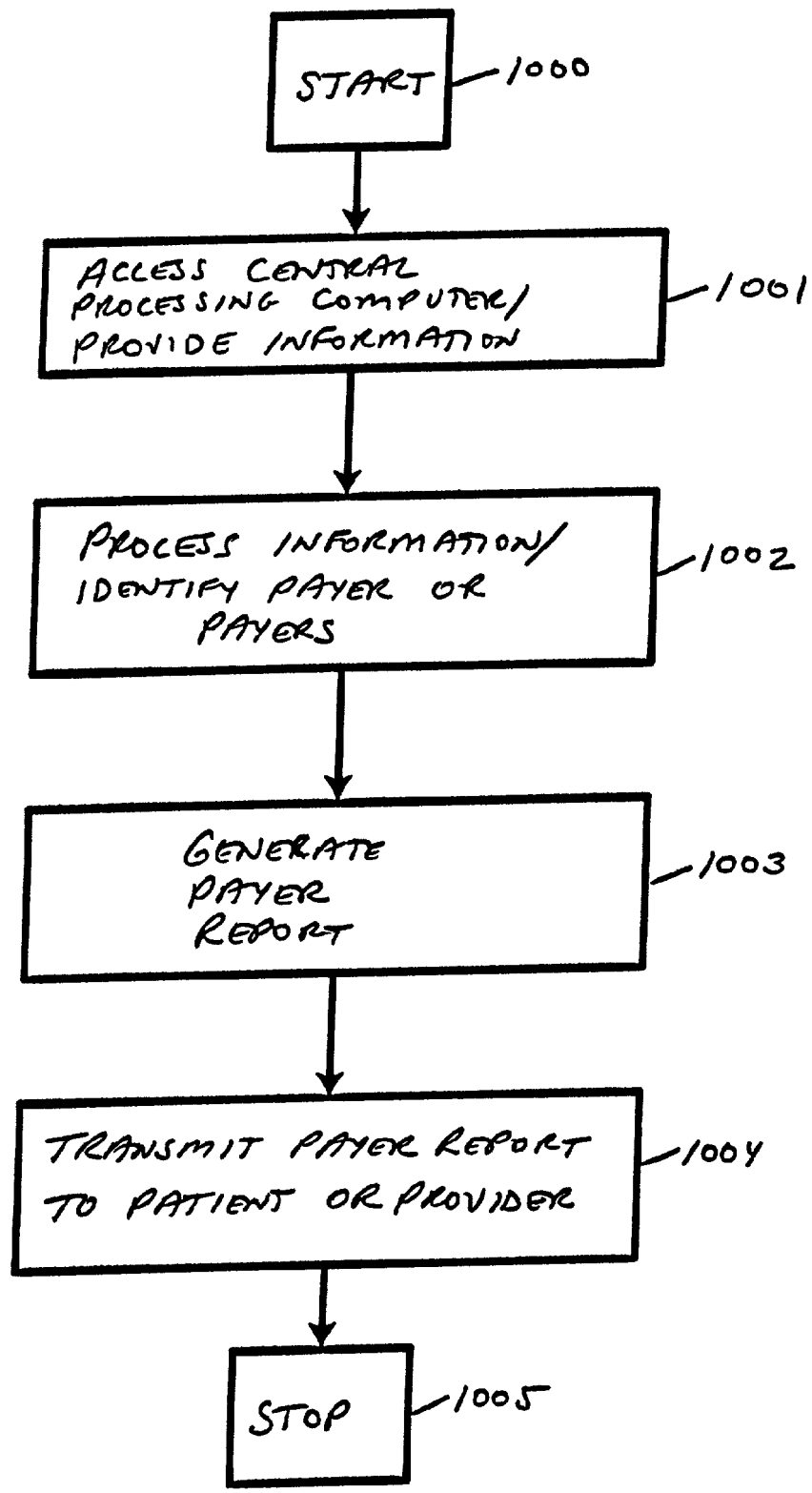
FIG. 10 illustrates yet another preferred embodiment method of using the present invention, in flow diagram form.

FIG. 10 illustrates another preferred embodiment method of utilizing the present invention. In the embodiment of FIG. 10, the present invention can be utilized by any patient, user, provider, payer, and/or intermediary, in order to locate a provider and/or a payer of healthcare and/or healthcare-related services, goods, or products. For example, assume that a patient has been recently diagnosed as needing an operation to repair his vision. The patient or his provider would need to find a doctor who specializes in performing the needed surgical procedure. The present invention can thereafter be utilized to locate a specialist for performing that function.

With reference to FIG. 10, operation of the apparatus 100 commences at step 1000. At step 1001, the patient or provider accesses that central processing computer 10 and provides information regarding the service needed. At step 1002, the central processing computer 10 will process the request and identify one or more specialists along with their backgrounds, insurance coverage accepted, fees, and/or any educational, professional experience and/or any other information about the provider. At step 1003, the central processing computer 10 can generate a provider report and transmit same to the patient or provider at step 1004. Thereafter, operation of the apparatus ceases at step 1005.

In a similar manner, the embodiment of FIG. 10 can be utilized to find a facility for receiving a certain and/or desired form of care and/or for obtaining a certain procedure. In this embodiment, the facility is defined to be the provider and the present invention can be utilized as described above.

In another similar manner, the embodiment of FIG. 10 can be utilized to find a payer or insurance company for providing desired coverage and/or for paying for certain treatments and/or procedures. In the case of locating payers, the method of FIG. 10 can be repeated for locating payers for certain healthcare services, goods or products.

At step 1001, the patient or provider accesses that central processing computer 10 and provides information regarding the coverage needed. At step 1002, the central processing computer 10 will process the request and identify one or more payers along with information about the payer or payers. At step 1003, the central processing computer 10 can generate a payer report and transmit same to the patient or provider at step 1004. Thereafter, operation of the apparatus ceases at step 1005.

In another similar manner, the embodiment of FIG. 10 can be utilized to find and/or locate supplies, body organs, blood, medications, and/or any other goods, products, and/or supplies, etc. In this embodiment, the identification, location, cost, etc., of any of the above goods, products, supplies, organs etc., can be stored in the database 10H.

With reference to FIG. 10, operation of the apparatus 100 commences at step 1000. At step 1001, the patient or provider accesses that central processing computer 10 and provides information regarding the supply, body organ, blood, medication, and/or any other good, product, or supply or supplies needed.

At step 1002, the central processing computer 10 will process the request and identify the existence and/or location of the respective supply, body organ, blood, medication, and/or any other good, product, or supply or supplies, along with its location, cost and any other pertinent information. At step 1003, the central processing computer 10 can generate a report and transmit same to the patient or provider at step 1004. Thereafter, operation of the apparatus ceases at step 1005.

In another similar manner, the embodiment of FIG. 10 can be utilized to find a payer or insurance company for providing desired coverage and/or for paying for certain treatments and/or procedures. In the case of locating payers, the method of FIG. 10 can be repeated for locating payers for certain healthcare services, goods or products. At step 1001, the patient or provider accesses that central processing computer 10 and provides information regarding the coverage needed. At step 1002, the central processing computer 10 will process the request and identify one or more payers along with information about the payer or payers. At step 1003, the central processing computer 10 can generate a payer report and transmit same to the patient or provider at step 1004. Thereafter, operation of the apparatus ceases at step 1005.

The embodiment of FIG. 10 can also be utilized by intermediaries, such as insurance brokers who need to find certain insurance companies and/or payers who meet the needs of certain patients and/or clients, and/or other individuals and/or third parties.

In another preferred embodiment of FIG. 10, any patient, user, provider, payer, and/or intermediary can request to be notified of the availability of a provider, the emergence of a patient in need of a certain care, the availability of a payer or an insurance company to offer a policy or a certain policy, the availability of a healthcare facility to provide certain care, the availability of certain supplies, a body organ, a blood type, an expiration of an insurance policy (i.e. healthcare insurance, life insurance, disability insurance, etc.,) and/or the occurrence of any event which may be of interest to any of the patients, users, providers, payers, and/or intermediaries, described herein.

In this embodiment, the party requesting to be notified of the event or occurrence, whichever it may be, (hereinafter the "requesting party"), can access the central processing computer 10 via their respective communication device. Thereafter, the requesting party can enter his request, provide any conditions attached to the request, and provide contact information. The central processing computer 10 can process the information received from the requesting party and store all pertinent information in the database 10H.

Thereafter, another party (hereinafter the "supplying party") contacts the central processing computer 10, either to enter information about the occurrence of an event and/or the availability of a service, a good or products, and/or any other herein-described and/or envisioned occurrence and/or good, product and/or service availability, or to review requests which have been previously submitted, which the supplying party may be interested in responding to.

If the entry of the supplying party can satisfy a request of a requesting party, and/or if the supplying party desires to satisfy a request of a requesting party, the central processing computer 10 will generate and/or transmit an e-mail message, a beeper or pager message, and/or a telephone call, and/or other communication to the communication device of the requesting party.

The communication or message can include information for bring the requesting party and the supplying party together to act towards effecting and/or consummating the transaction. Thereafter, upon notification to the central processing computer 10 by either the requesting party and/or the supplying party, or both, the central processing computer 10 can remove the request from the database 10H. In this manner, the central processing computer 10 and/or the apparatus 100 can be utilized as a clearinghouse for effecting transactions for any of the services, goods, products, and/or any other entities described herein.

In another preferred embodiment, the present invention can be utilized to schedule appointments with any of the patients, providers, payers, and/or intermediaries, described herein. In this manner, for example, can make an appointment with the provider over the communication network which services the present invention.

Figure 11A:
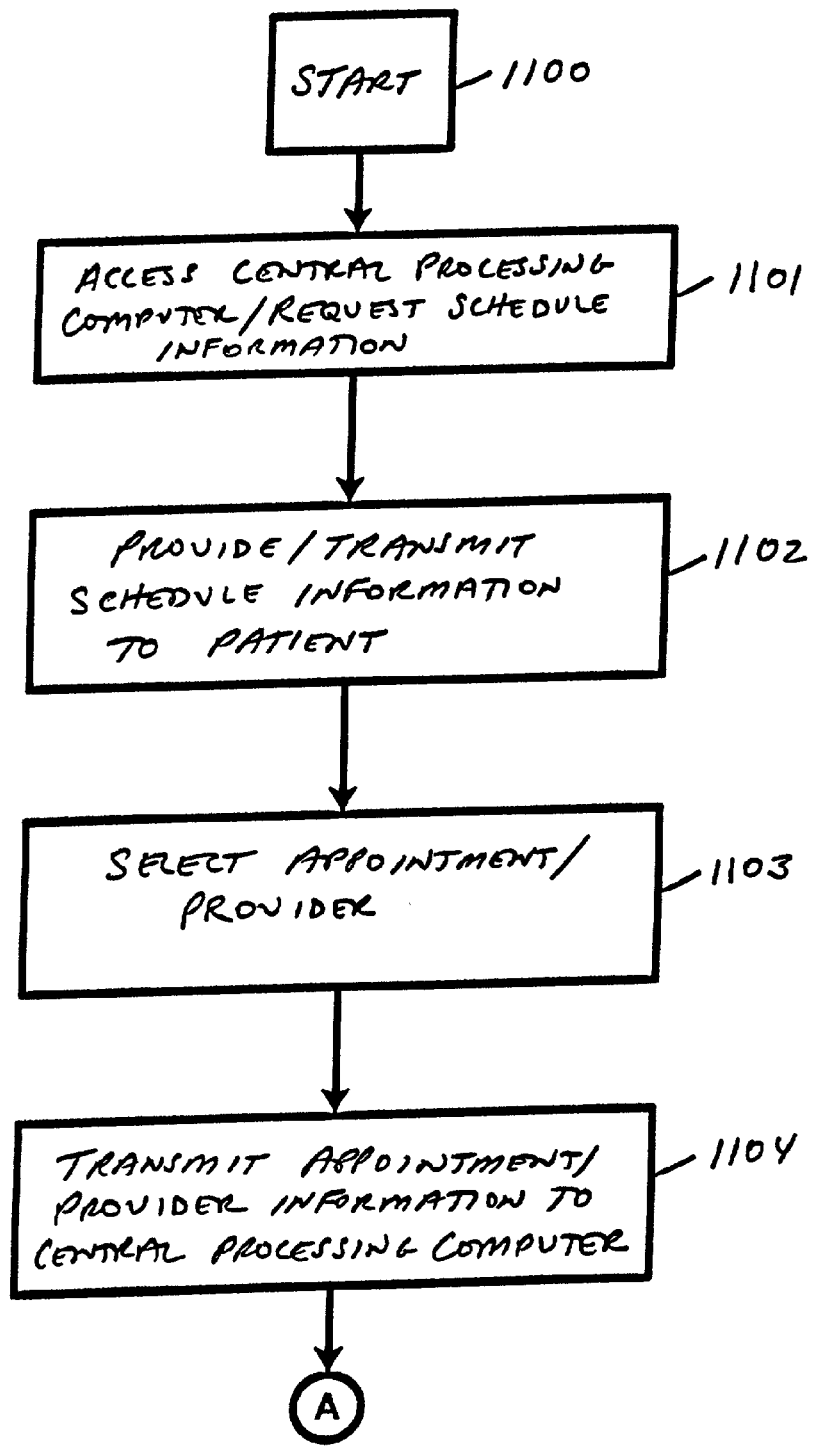
FIGS. 11A and 11B illustrate another preferred embodiment method of using the present invention, in flow diagram form.
Figure 11B:
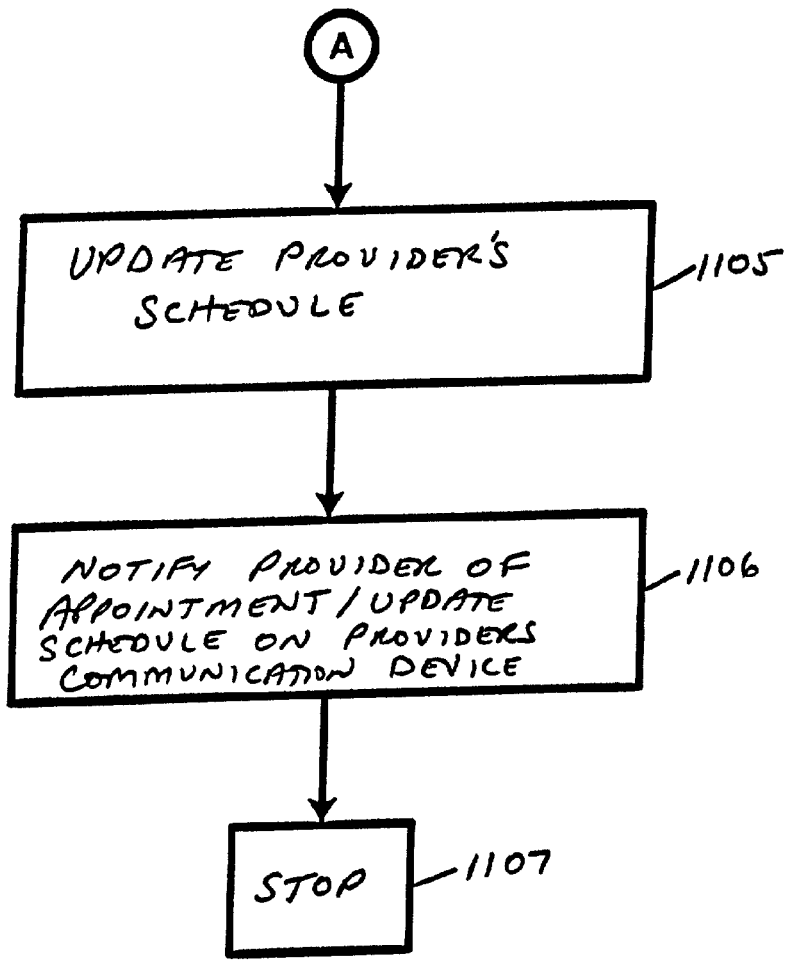

FIGS. 11A and 11B illustrate another preferred embodiment method of using the present invention, in flow diagram form. In the embodiment of FIGS. 11A and 11B, provider scheduling information can be stored in the database 10H. Operation of the apparatus 100 commences at step 1100. At step 1101, the patient accesses the central processing computer 10 and requests the schedule or schedules of a provider or a number of providers. At step 1102, the central processing computer 10 provides the schedule information to the patient. At step 1103, the patient can select the appointment he or she wishes to make.

At step 1104, the appointment information is transmitted to and received at the central processing computer 10. At step 1105, the central processing computer 10 will update the provider's schedule to reflect the new appointment. At step 1106, the central processing computer 10 will transmit a signal, such as an e-mail and/or other transmission and/or communication to provider communication device 20 to notify the provider and to update the providers schedule on the provider computer 20. In the preferred embodiment, the scheduling files stored on the database 10H of the central processing computer 10 and the database 20H on the provider communication device 20, and/or any portions and/or fields, or records, of same, can be dynamically linked to one another so that changes made to the schedule or schedules by either the central processing computer and/or on the provider communication device will be reflected in real-time so as to ensure that the most up-to-date schedules are available at all times.

Operation of the apparatus 100 will thereafter cease at step 1107. In another preferred embodiment, the central processing computer and/or the provider communication device can generate and/or transmit an e-mail to the patient communication device 40 in order to confirm the appointment and/or to serve as a reminder to the patient.

In the same manner, any patient, user, provider, payer, and/or intermediary can utilize the preferred embodiment of FIGS. 11A and 11B in order to schedule an appointment with any other patient, user, provider, payer, and/or intermediary, described herein.

In another preferred embodiment, the present invention can be utilized by intermediaries, such as, but not limited to brokers, insurance brokers, agents, and others, in order to service their respective clients. For example, the database 10H can contain insurance policy information, conditions, premiums, insurers providing same, as well as any other useful information in servicing insured's needs. The database 10H can also contain client information, policy requirements for any of the health insurance, life insurance, and/or disability insurance, policies in force for the insured along with premiums paid and/or expiration dates.

In another preferred embodiment, a broker, for example can prepare policy quotes, compare available policies, generate policies, and service policy claims via the information provided by the central processing computer 10 and/or the apparatus 100 of the present invention. The broker may also request to be notified, electronically and/or otherwise via a message generated and/or transmitted via the central processing computer 10, of times and/or instances when an insured's policy is up for renewal.

The broker may then utilize any of the information provided by, and/or contained in, the database 10H of the present invention in order to respond to an insured client's needs and/or requests, such as, but not limited to preparing policy quotes for comparison, finding a policy and/or policies for addressing the insured's particular needs, assisting in resolving claims issues and/or claims processing issues, and/or assisting and/or providing any other information which could allow the broker or other intermediary to provide assistance to, and/or to provide added value to its client or clients.

In this, manner, the present invention can provide a platform for allowing a broker to provide improved services to his or her insured while also providing for a more paperless working relationship.

In another preferred embodiment of the present invention, the present invention can be utilized in order to provide notification to any of the patients, providers, payers, users, and/or intermediaries. For example, a medical specialist can be electronically and/or otherwise notified if a patient is diagnosed with an illness and/or a condition which he or she specializes in treating.

As another example, a payer can be electronically and/or otherwise notified when a patient may be admitted to a hospital and/or other facility for care. The present invention can also be utilized to electronically and/or otherwise notify a provider when his or her patient has been diagnosed with an illness even when the patient may not be under the provider's care, and/or to notify a patient if a provider has become available to perform a treatment and/or a procedure on, and/or for, the patient.

The present invention can also be utilized in order to provide notification, electronically and/or otherwise, to any respective party, regarding any event, happening, and/or occurrence, which is described herein and/or which may be reasonably foreseen from the comprehensive nature of the present invention in providing comprehensive healthcare processing.

Figure 12A:
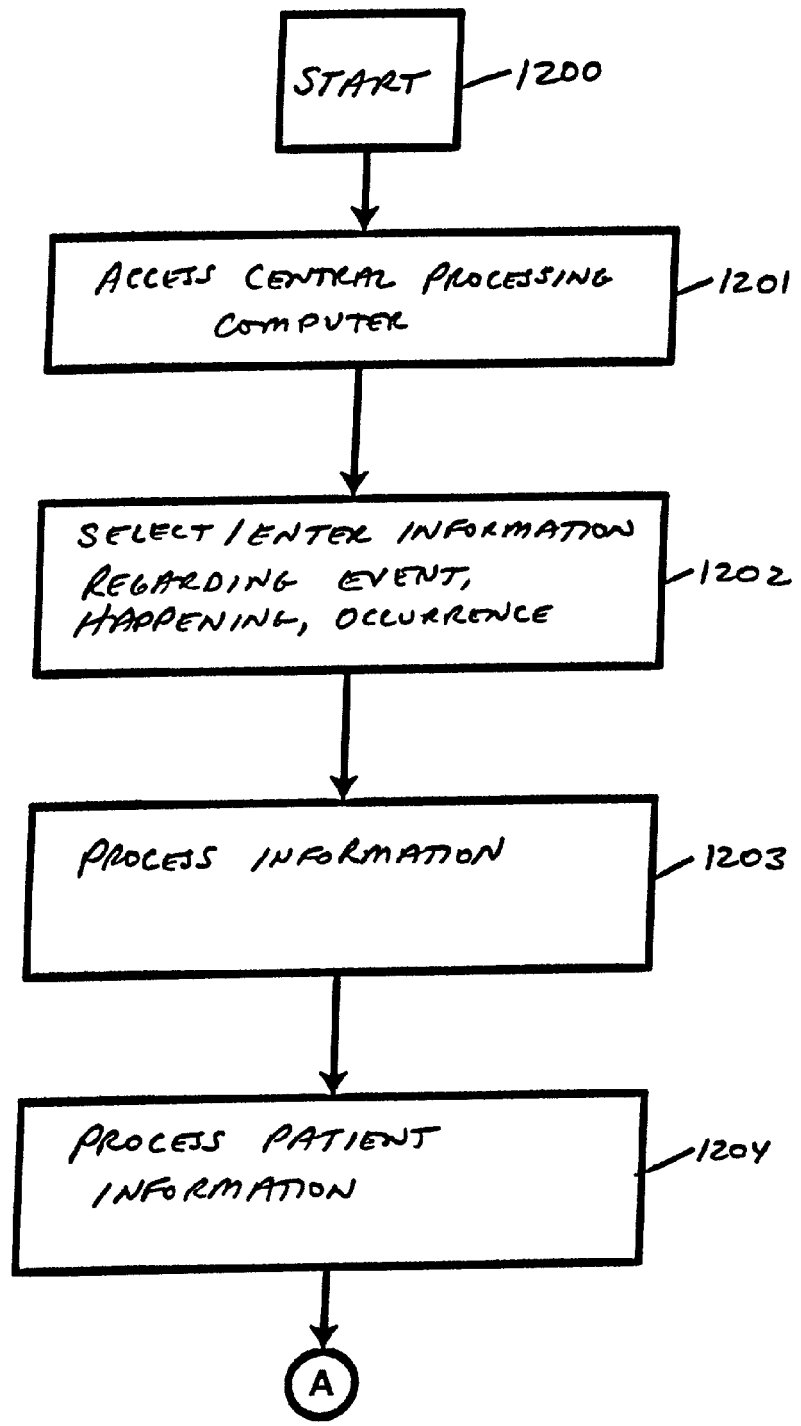
FIGS. 12A and 12B illustrate still another preferred embodiment method of using the present invention, in flow diagram form.
Figure 12B:
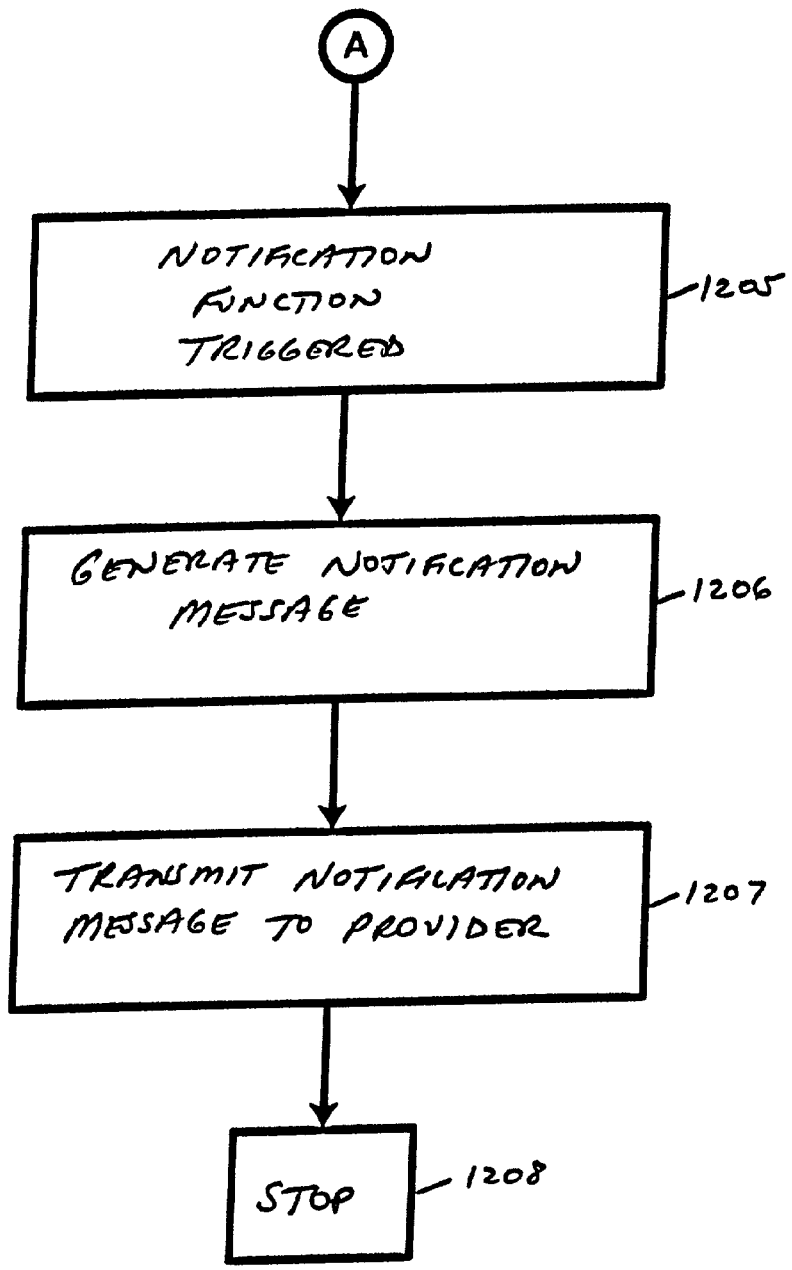

FIGS. 12A and 12B illustrate another preferred embodiment method of utilizing the present invention, in flow diagram form. In the preferred embodiment of FIGS. 12A and 12B, the present invention can provide notification to any respective party, electronically and/or otherwise, in response to the occurrence of an event, happening, and/or occurrence.

While the description of the embodiment of FIGS. 12A and 12B will be directed to notifying a doctor or other healthcare provider when a patient requires the provider's treatment and/or care, it is important to note that the embodiment of the FIGS. 12A and 12B can be utilized so as to provide notification services and/or functionality for any defined event, happening, and/or occurrence, and to any of the respective patients, users, providers, payers, and/or intermediaries, described herein.

The operation of the apparatus 100 commences at step 1200. At step 1201, the provider can access the central processing computer 10. At step 1202, the provider can select and/or enter the information concerning the notifying event, happening, and/or occurrence, and/or the conditions for notifying the provider. For example, an obstetrician can request to be notified when a pregnant patient enters a hospital in labor. At step 1203, the central processing computer 10 processes the above information. At step 1204, the central processing computer 10, upon receiving information concerning the pregnant patient's admission to the hospital, will process the pregnant patient's information.

At step 1205, the central processing computer 10 will identify and/or ascertain that the provider's condition for notification has been met or has been triggered. Thereafter, at step 1206, the central processing computer will generate an appropriate message to notify the provider. At step 1207, the central processing computer 10 can transmit the notification message to the provider's communication device as any one or more of an e-mail, a beeper or pager message, a telephone call, and/or in any other manner. The central processing computer 10 can also transmit multiple notification messages to multiple communication devices such as a computer, a personal digital assistant, a beeper or pager and/or a telephone. Thereafter, operation of the apparatus will cease at step 1208.

In a similar manner, a payer may also request to be notified upon the admission of a patient to a hospital and/or other care facility. A patient may also request that certain providers and/or payers be notified by the present invention of an event, happening, and/or occurrence involving the patient. There is no limit to the scenarios and/or alternate embodiments in which the present invention can be utilized in order to provide notification to any of the patients, users, providers, payers, and/or intermediaries, described herein.

In still another preferred embodiment, the present invention can be utilized to facilitate healthcare claims processing. Any of the patients, providers, payers, users, and/or intermediaries, can file claims with the respective party electronically via the present invention. The claim forms for each payer and/or other party can be accessed from the respective party's communication device, filled out and submitted electronically by the claiming party or claimant. Any and/or all submissions can be electronically dated and/or otherwise marked, the status of the claim can be provided to the claimant at any time and any interested third parties may be notified of any action taken on a claim.

Figure 13A:
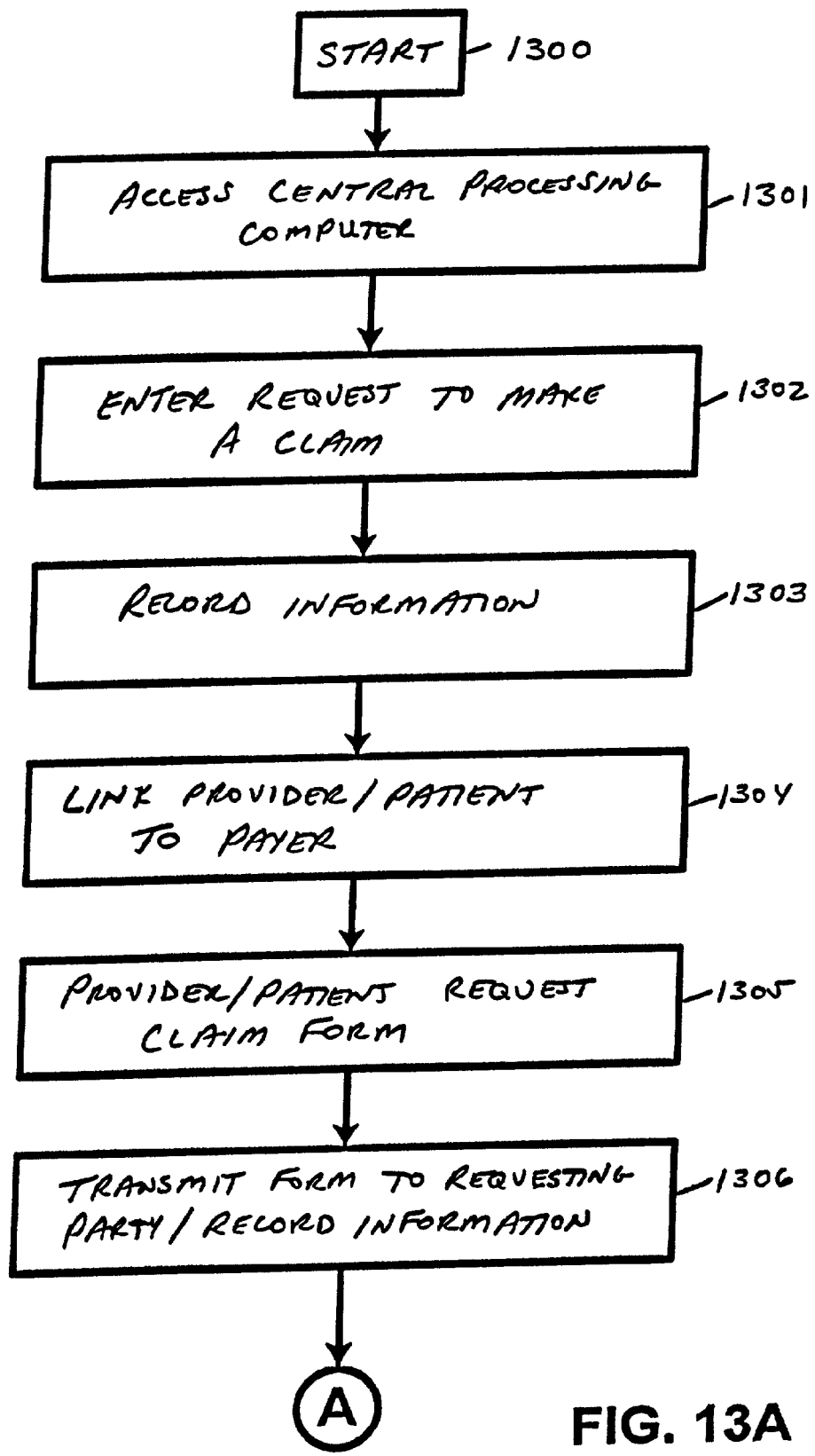
FIGS. 13A, 13B and 13C illustrate yet another preferred embodiment method of using the present invention, in flow diagram form.
Figure 13B:
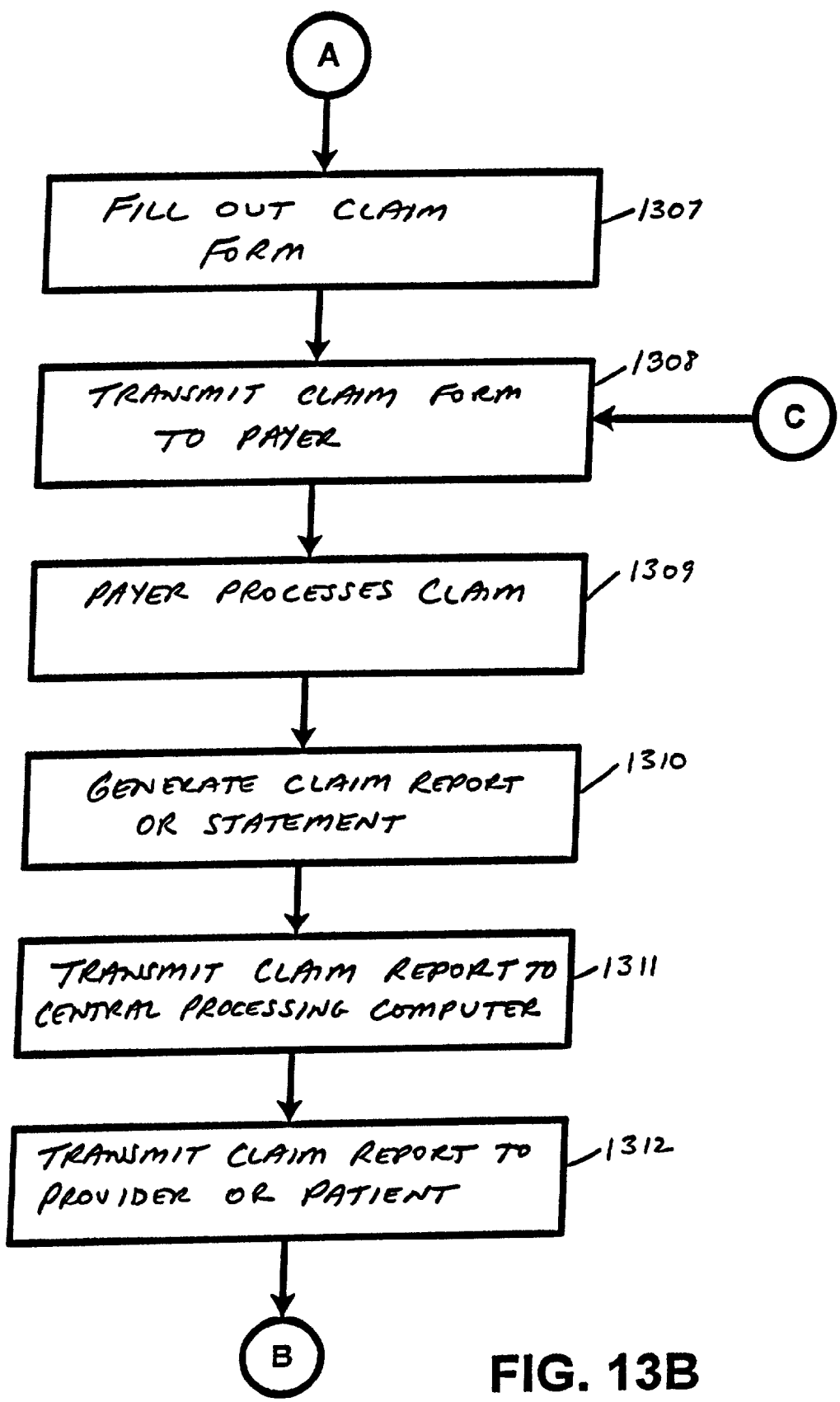
Figure 13C:
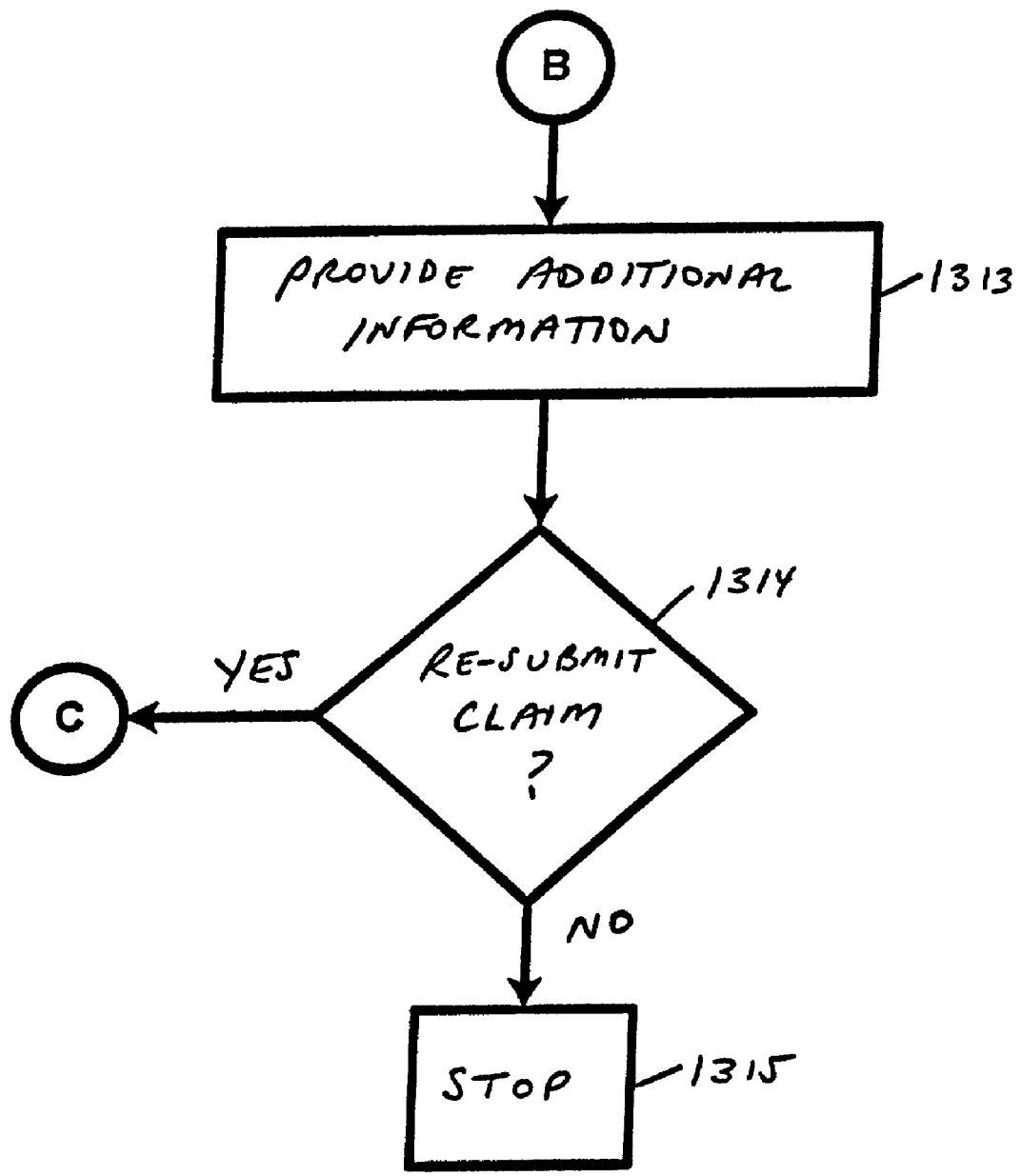

FIGS. 13A, 13B and 13C illustrate a method of utilizing the present invention to perform claims processing services. While it is understood that any appropriate party can file claims with any party described herein, for simplicity, a preferred embodiment where providers and/or patients file claims is described herein. The method, however, can be adapted for use by any party described herein.

With reference to FIGS. 13A, 13B and 13C, operation of the apparatus 100 commences at step 1300. At step 1301, the provider or patient, whichever the case may be, accesses the central processing computer 10 via the respective communication device 20 or 40. At step 1302, the provider or patient enters a request to make a claim.

At step 1303, the central processing computer 10 will record any information regarding the claim request and, thereafter, at step 1304, link the provider or patient directly to the respective payer communication device 30. At step 1305, the provider or patient can request a claim form. At step 1306, the claim form will be transmitted from the payer communication device 30, via the central processing computer 10, which will record the occurrence of same, to the communication device 20 or 40 of the respective provider or patient. The provider or patient can fill out the form on the respective communication device 20 or 40 at step 1307.

At step 1308, the provider or patient transmits the completed form to the payer communication device 30 via the central processing computer 10 which will record the occurrence of same. At step 1309, the payer will process the claim and, at step 1310, generate a claim report or statement. At step 1311, the claim report or statement is transmitted to the central processing computer 10, which can record the occurrence as well as the action taken by the payer (i.e. claim approved or denied).

Thereafter, the central processing computer 10 will, at step 1312, transmit the claim report or statement to the communication device 20 or 40, respectively, of the provider or patient. Thereafter, at step 1313, the provider or patient can provide the additional information and/or re-submit the claim form to the central processing computer. At step 1314, the central processing computer 10 will determine if the provider or patient has provided additional information and/or has decided to resubmit the claim.

If, at step 1314, it is determined that additional information has been provided and/or that the claim is to be re-submitted, the processing will proceed to step 1308 and the processing of steps 1308 through 1314 will be repeated until a resolution is reached between the parties involved. Thereafter, the operation of the apparatus 100 will cease at step 1315. If at step 1314, it is determined that no new additional information has been submitted and/or that the claim is not to be re-submitted then the operation of the apparatus 100 will cease at step 1315.

In this manner, the present invention can facilitate an expedited and/or a paperless claim process. Further, records of the transactions, such as, but not limited to claim request, claim form request and/or delivery, claim submission, claim processing, claim report or statement, claim re-submission, provision of additional information, and/or any and/or all other transactions, which occur during the claim processing procedure or process, can be recorded and maintained at the central processing computer 10 so as to provide for a third party record and/or monitoring of same.

The central processing computer 10, can notify any party described herein, as well as any third parties, regarding any event, happening, occurrence, and/or any aspect of any claim submission and/or processing activities. For example, a provider can be notified at regular interval on a payer's or payers decisions to pay for certain treatments and/or procedures. Similarly, a patient's employer can be notified regarding claim payments made by its group health insurer so as to ensure that its employees are being properly serviced and/or provided for. Other information may similarly be provided to any appropriate requesting party described herein and/or any qualified and/or appropriate third party. Notification can be provided to any appropriate party, via any of the communication methods and/or techniques described herein, and can be for, and/or include, any pertinent information.

The apparatus of FIGS. 13A and 13B can also utilize electronic signatures and/or process electronic signatures and/or electronic signature information which can correspond to any of the herein-described parties in performing any of the herein-described processing routines and/or functions.

Figure 14A:
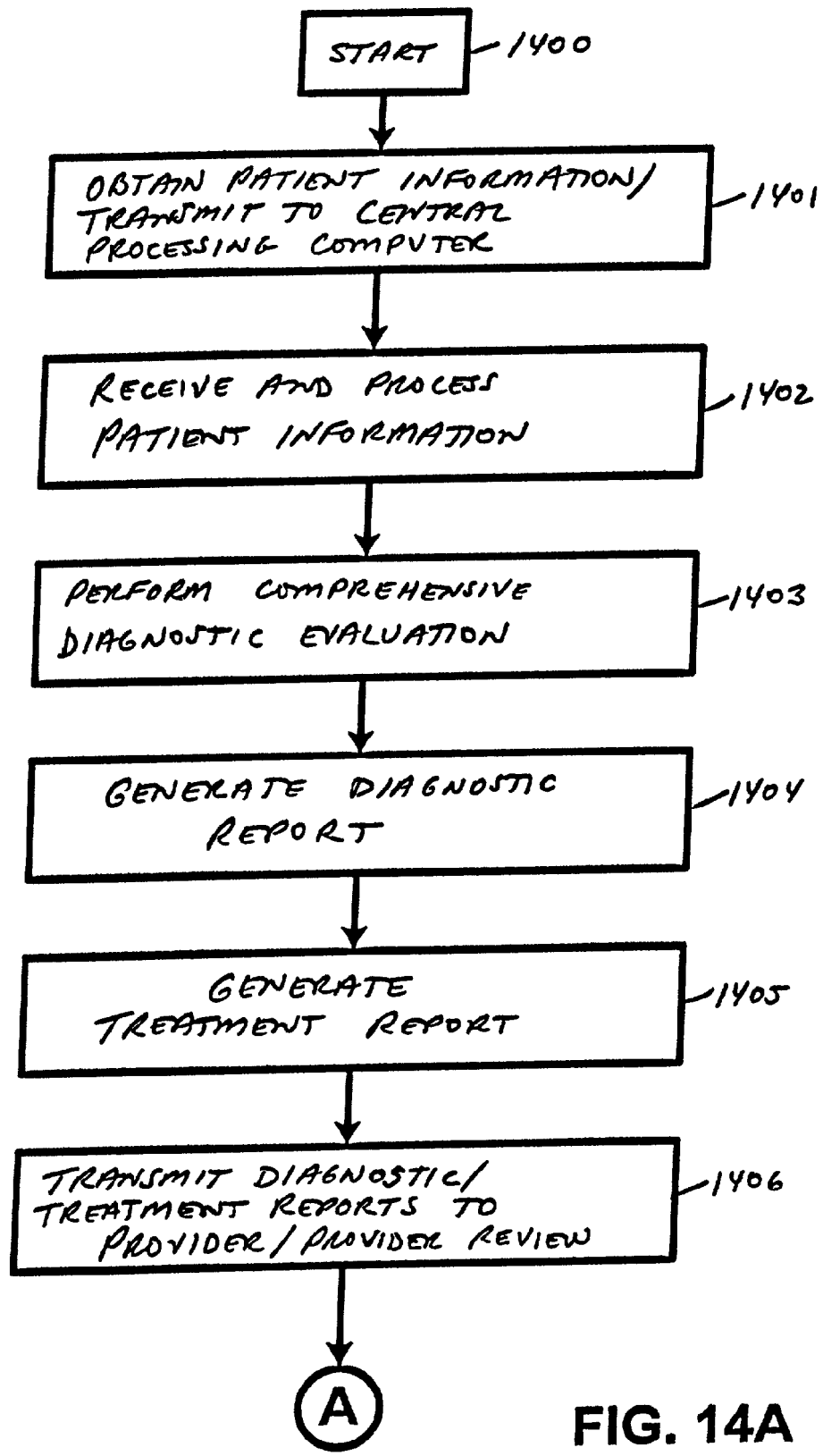
FIGS. 14A and 14B illustrate another preferred embodiment method of using the present invention, in flow diagram form.
Figure 14B:
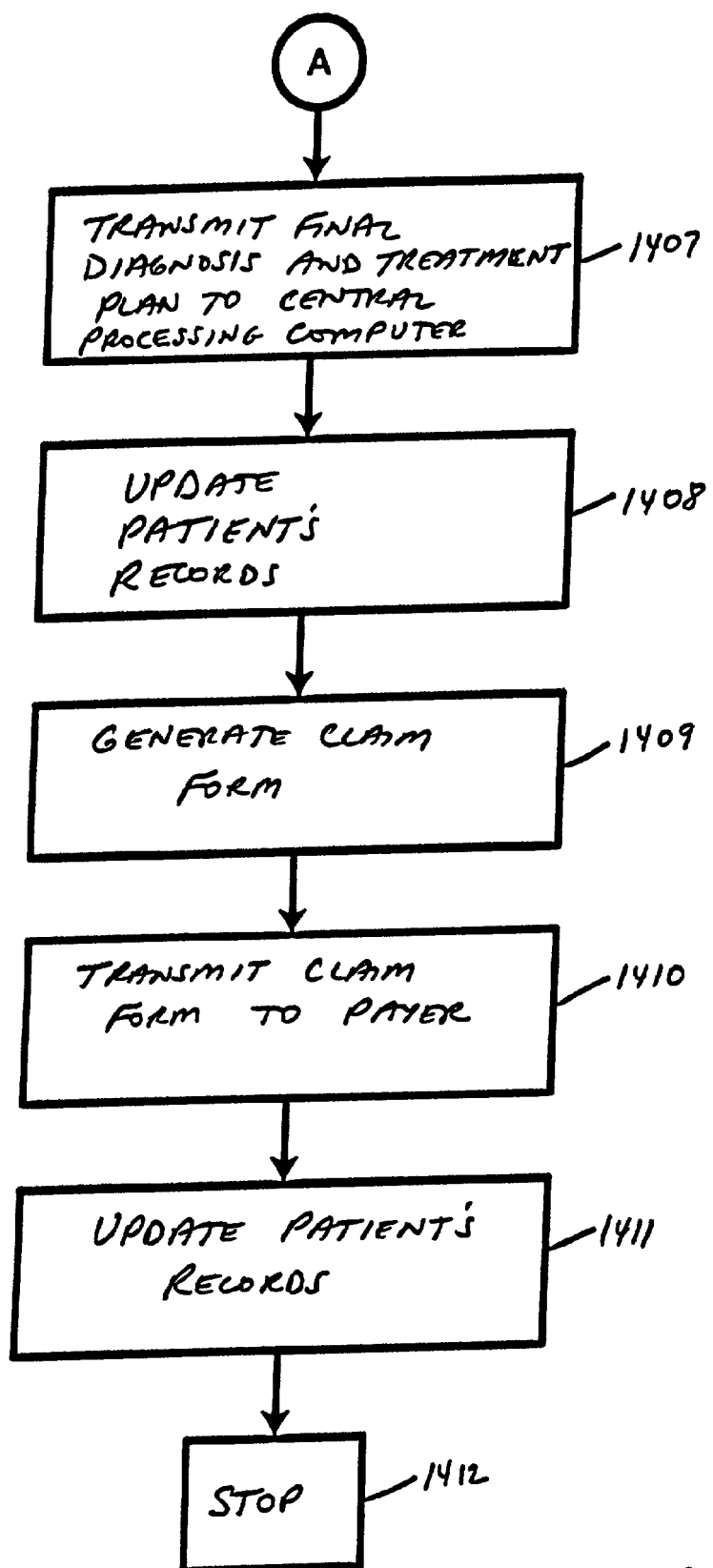

In another preferred embodiment, the present invention can provide for automatic claim submission via the central processing computer 10 once a final diagnosis and treatment has been prescribed by a provider and/or upon the occurrence of an examination and/or the administration of a treatment. FIGS. 14A and 14B illustrate another preferred embodiment method of utilizing the present invention.

With reference to FIGS. 14A and 14B, operation of the apparatus 100 commences at step 1400. At step 1401, the patient's symptoms, if any, and/or examination findings are obtained from the patient and transmitted from the provider communication device 20 to the central processing computer 10. The central processing computer 10 will, at step 1402 receive and process the patient symptoms, if any, and/or the examination findings, in conjunction with the patient's medical history and/or other information, medical theories, principles, criteria and/or other medical information needed to make a diagnosis. At step 1403, the central processing computer 10 will perform a comprehensive diagnostic evaluation of the patient's symptoms, if any, and/or the examination findings.

At step 1404, the central processing computer 10 will generate a diagnostic report which can include a diagnosis of the patient's condition. The diagnostic report which is generated at step 1404 can, if needed, include a single diagnosis and/or a list of possible diagnoses along with their respective probabilities, which may pertain to the patient's condition. At step 1405, the central processing computer 10 can then generate, if needed, a treatment report which will outline and/or prescribe treatment for the single diagnosis and/or for the list of possible diagnoses. The central processing computer 10, when generating the treatment report, can, if needed, process same in conjunction with, and consider, possible drug interactions and/or treatment interactions.

At step 1406, the central processing computer 10 will transmit the diagnostic report and/or treatment report to the provider's communication device 20 at which point the medical doctor can obtain the diagnosis or possible diagnoses and corresponding treatment plans, if any. The medical doctor can then review the diagnostic report and/or treatment report and choose a final diagnosis and/or treatment plan to administer to the patient. At step 1407, the medical doctor will transmit the final diagnosis and treatment plan, including the prescribed treatment and/or treatment plan, to the central processing computer 10. At step 1408, the central processing computer will then update the patient's records in the database 10H so as to include all of the data and information described as being processed and/or generated by the central processing computer 10, including, but not limited to the patient's symptoms, the information contained in the diagnostic report and the treatment report, the final diagnosis and the prescribed treatment.

Thereafter, at step 1409, the central processing computer 10 will generate a claim form which can meet the formal claim submission requirements of the patient's payer or insurance company. At step 1410, the claim form will be submitted by the central processing computer 10 to the respective payer computer 30. At step 1411, any and/or all pertinent information regarding the claim submission, the patient, the provider visit, and/or any diagnoses and/or treatments considered, the final diagnosis and/or the prescribed treatment, can be stored and the patient's records will then be updated and be available for the patient's next treatment and/or diagnosis.

The operation of the apparatus 100 will then cease at step 1412. In this manner, the present invention can provide for the automatic and/or for the programmed submission of healthcare claims, claim for ms, claim requests, benefit requests, etc., upon the conclusion of a provider's service, consultation, treatment, procedure, and/or any other event which triggers coverage under a healthcare insurance policy and/or a payer's liability to pay for services and/or treatments.

In the embodiment of FIGS. 14A and 14B, as well as any and/or all of the other embodiments described herein, the present invention can utilize and/or process electronic signatures in order to effectuate and/or process any of the respective transactions which are described as taking place between, and/or which can transpire involving, any of the respective parties described herein. Applicant hereby incorporates by reference herein the subject matter and teachings of *Applied Cryptography*, Second Edition, Bruce Schneier, Wiley, 1996.

The present invention can also be utilized, in the manner described above, in connection with claiming healthcare insurance benefits, to claim disability insurance benefits and/or life insurance benefits.

In another preferred embodiment, the apparatus 100 can administer and/or maintain financial accounts for, and/or on behalf of, any of the patients, users, providers, payers, and/or intermediaries, described herein. In this manner, any of the parties described herein as utilizing the services of the apparatus 100, and/or the central processing computer 10, can have all financial transaction managed and/or monitored by the central processing computer 10. In the preferred embodiment, the financial accounts can be conventional savings accounts, checking account, credit accounts, debit accounts, electronic money accounts, digital money accounts, etc., and/or any other appropriate account(s).

In the preferred embodiment, any of the respective parties may select to have the central processing computer 10 administer any financial transactions on their behalf. For example, a payer may deposit a sum of money which can be ear-marked for payment of healthcare provider services. A provider may open an account and deposit a sum of money to pay any vendor bills. The provider may also open an account to receive payment from payers and/or patients for services rendered. Each time a financial transaction is to occur, such as, for example, the payment from a payer to a provider resulting from a patient's claim, the central processing computer 10 will transfer funds (and/or deduct funds) from the payer's account and deposit the funds (and/or add the funds) to the providers account. Notwithstanding the examples provided above, the central processing computer 10 can effectuate any type of financial transaction(s) for, between, and/or on behalf of, any of the parties described herein. Further, the apparatus 100 and/or the central processing computer 10 can process electronic signatures which can be associated with and/or which can correspond to any of the respective parties to a transaction.

The central processing computer 10, in the preferred embodiment, can maintain detailed records of any and/or all of such transfer and/or transactions and provide periodic account statements to the respective parties maintaining accounts with the central processing computer 10. In this manner, the present invention can provide an apparatus and a method for maintaining financial accounts, effecting financial transactions, and providing accounting and/or other notification services, for, and/or on behalf, any of the parties described herein.

In another preferred embodiment, the apparatus and method of the present can be utilized healthcare training simulator for any of the providers, healthcare providers, healthcare professionals, and/or other providers described herein. The present invention can also be utilized by any user and/or individual wishing to learn about a certain healthcare field or topic. The present invention can be utilized to provide formal training, supplemental training, informal training, continuing education training, and/or any other training.

Figure 15A:
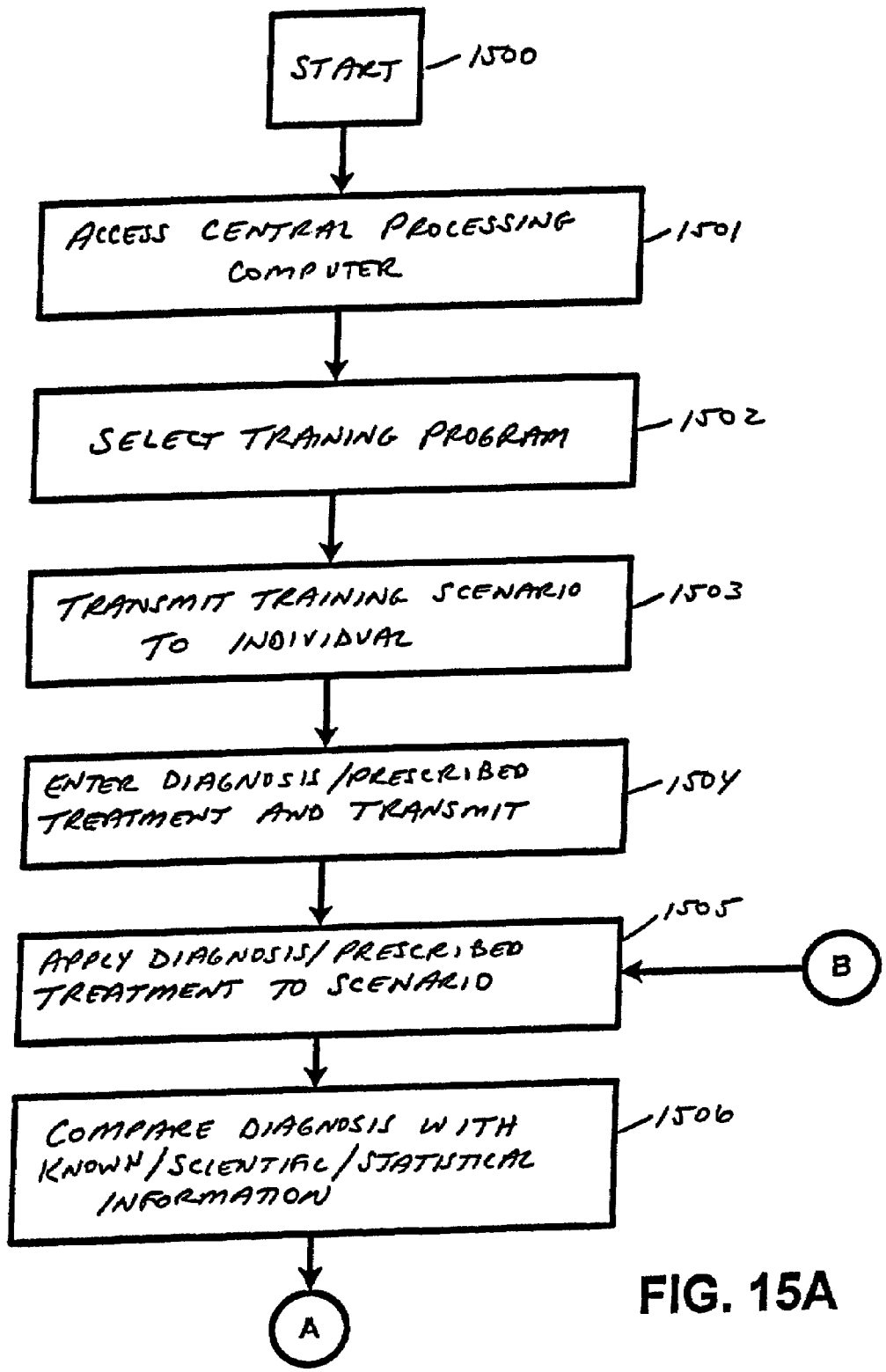
FIGS. 15A and 15B illustrate another preferred embodiment method of using the present invention, in flow diagram form.
Figure 15B:
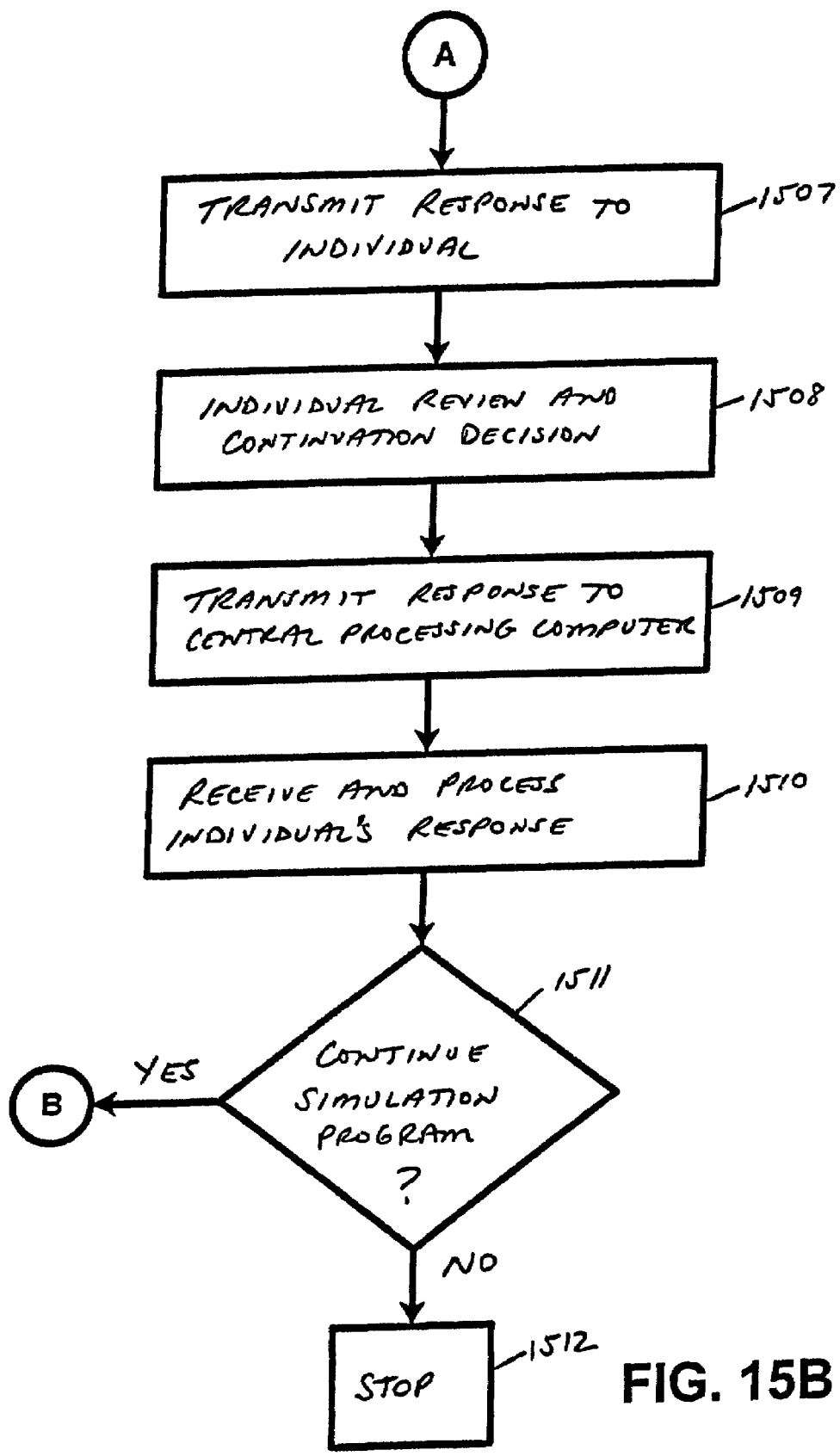

FIGS. 15A and 15B illustrates another preferred embodiment method for utilizing the present invention, in flow diagram form. The operation of the apparatus commences at step 1500. At step 1501, the individual utilizing the training simulator (referred to hereinafter as "the user") who could be any provider, student provider, and/or any other individual and/or party described herein, can access the central processing computer 10 via an appropriate computer or communication device. At step 1502, the user can select the training program which he or she wishes to train from. At step 1503, the central processing computer 10 will transmit the training scenario and/or information, including the symptoms and/or conditions of a hypothetical patient. The training scenario can include any one or more of text information, a video tapped file or video clip, audio information, and/or any other multimedia information.

At step 1504, the user can enter his or her diagnosis and prescribed treatment and/or treatments for the presented scenario and transmit same to the central processing computer 10. At step 1505, the user's diagnosis and prescribed treatment can be applied to the scenario. At step 1506, the central processing computer 10 will compare the diagnosis against any diagnosis or diagnoses which are known to be correct and/or against any scientific and/or statistical norms. At step 1506, the central processing computer 10 will apply the prescribed treatment or treatments to the hypothetical patient and compute a revised set of symptoms and/or conditions which can result from the applied treatment and/or treatments. Once again, statistical information can be utilized to arrive at a realistic response to the treatment and/or treatments. The user's diagnosis and prescribed treatment, as well as information regarding the correctness and/or viability of same can be recorded by the central processing computer 10 at step 1506.

At step 1507, the central processing computer 10 will transmit a response to the user's diagnosis and prescribed treatment. The response can include the patient's response to the prescribed treatment, and/or an evaluation of the diagnosis and prescribed treatment or treatments. The response can also include training materials, which can include any one or more of text information, video information, and/or audio information.

At step 1508, the user can review the material and/or information contained in the response and can decide whether he or she wishes to continue the training simulation. At step 1509, the user will transmit a response to the central processing computer 10 which contains an instruction to either continue the simulation, in which case the user's response will also include a revised diagnosis and prescribed treatment or treatments, or to terminate the training simulation.

At step 1510, the central processing computer 10 will receive and process the user's response provided at step 1509. At step 1511, the central processing computer 10 will determine whether the user desires to continue the simulation or whether the user desires to terminate the simulation. If, at step 1511, it is determined that the user desires to continue the training simulation, the operation of the central processing computer 10 returns to step 1505 and the above-described process will be repeated from step 1505. If, however, it is determined that the user desires to terminate the training simulation the operation of the apparatus 100 will cease at step 1512. User responses, including diagnostic and treatment decisions, and/or performance, can be recorded and/or can be stored and, thereafter the information can be utilized to evaluate the user and/or for comparing the user's progress and/or improvements, as well as aptitude and skills, in the pertinent field of training, and/or the information can be utilized for any other useful purpose.

In this manner the apparatus and method of the present invention can be utilized to provide an interactive healthcare training simulator which can be utilized for training in any and/or all of the fields of medicine, surgery, psychiatry, psychology, psychotherapy, dentistry, oral surgery, nutrition, health and fitness, and/or in any other healthcare and/or healthcare-related field.

Data and/or information collected and/or stored by the apparatus 100, which relates to symptoms and/or conditions, as well as responses to treatments, can be utilized in order to present realistic and confidential training scenarios. In this manner, the present invention can be utilized to compile a vast amount of information relating to the various fields of healthcare. The information can then be utilized to provide realistic training for providers and/or student providers. In this manner, the present invention can utilize information obtained from other preferred embodiments in order to provide simulated training scenarios.

In another preferred embodiment, the apparatus 100 and method of the present invention can be utilized in order to maintain patient healthcare records or files private and/or to safeguard patient healthcare records or files, by restricting and/or limiting access to the respective records or files.

The apparatus 100 and/or the central processing computer 10 can process information regarding the identity of, and/or the information which is authorized and/or allowed to be provided to, a requesting individual or entity who or which can be any individual, entity, patient, provider, payer, and/or intermediary, and/or any other individual or entity, who or which may request information regarding a patient's or an individual's healthcare records or file. Thereafter, the apparatus 100 and/or the central processing computer 10 can determine whether the respective information requesting individual or entity is authorized or allowed to access, obtain, and/or to change or alter any information contained in a respective patient's or individual's healthcare records or file.

The apparatus 100 and/or the central processing computer 10 can utilize and/or process passwords, electronic signatures, and/or any other information and/or encoded and/or encrypted information in determining an individual's or an entity's authorization to access, obtain, and/or change or alter, any information in a respective healthcare record(s) or file(s).

If the apparatus 100 and/or the central processing computer 10 determines that an individual or entity is authorized or allowed to access, obtain, and/or to change or alter, any information contained in a respective patient's or individual's healthcare record(s) or file(s), the apparatus 100 and/or the central processing computer 10 will respectively allow access to the information, provide the information, and/or process and store changes, alterations, and/or updates, to the respective healthcare record(s) or file(s). If, however, the apparatus 100 and/or the central processing computer 10 determines that an individual or entity is not authorized or not allowed to access, obtain, and/or to change or alter, any information contained in a respective patient's or individual's healthcare record(s) or file(s), the apparatus 100 and/or the central processing computer 10 will prohibit or disallow access to the information.

In another preferred embodiment of the apparatus 100 and method of the present invention, the apparatus 100 can provide notification to patients or other individuals when others have accessed, obtained, and/or made changes to, their respective healthcare records or files. The apparatus 100 can also provide notification to healthcare provider's, including but not limited to, the patient's or individual's provider or providers, and/or healthcare payers or insurance providers, including but not limited to, the patient's or individual's healthcare payer(s) or insurance provider(s), when others have accessed, obtained, and/or made changes to, their respective healthcare records or files.

It is envisioned that healthcare records or files can be accessed, obtained, changed, or altered, by any one or more of a patient, an individual, a relative of a patient, a relative of a an individual, an interested third party, a healthcare provider, a healthcare provider to the patient, a healthcare provider to the patient or individual, a healthcare payer, an insurance provider, and/or a healthcare payer or insurance provider of the patient or individual. In this manner, the apparatus 100 and method of the present invention can maintain and/or safeguard healthcare records or files for any of the patients and/or individuals described herein. In the same manner, the apparatus 100 and method of the present invention can also maintain and safeguard records and/or files of, or regarding any of the herein-described healthcare providers and/or healthcare payers.

Figure 16A:
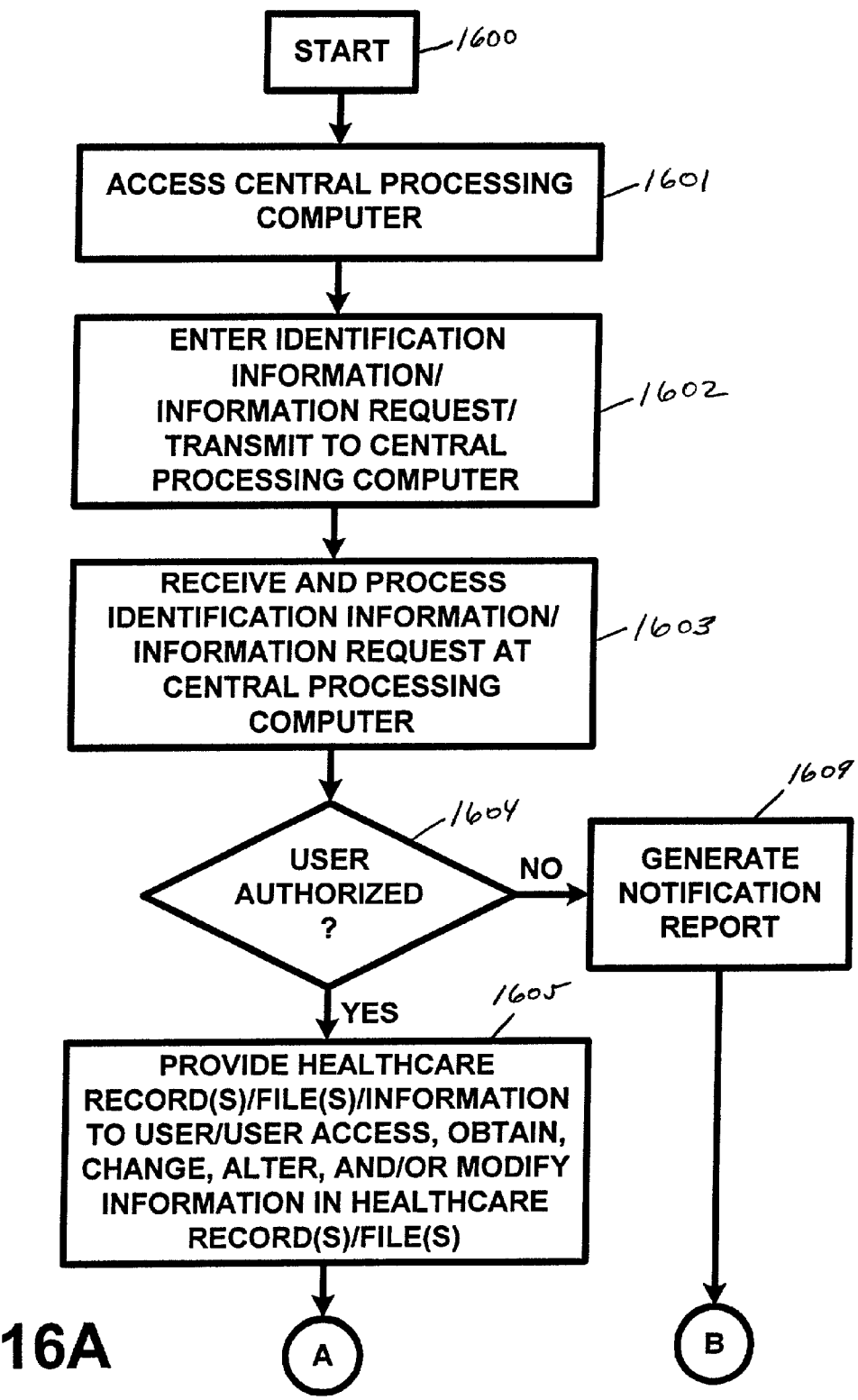
FIGS. 16A and 16B illustrate another preferred embodiment method of using the present invention, in flow diagram form.
Figure 16B:
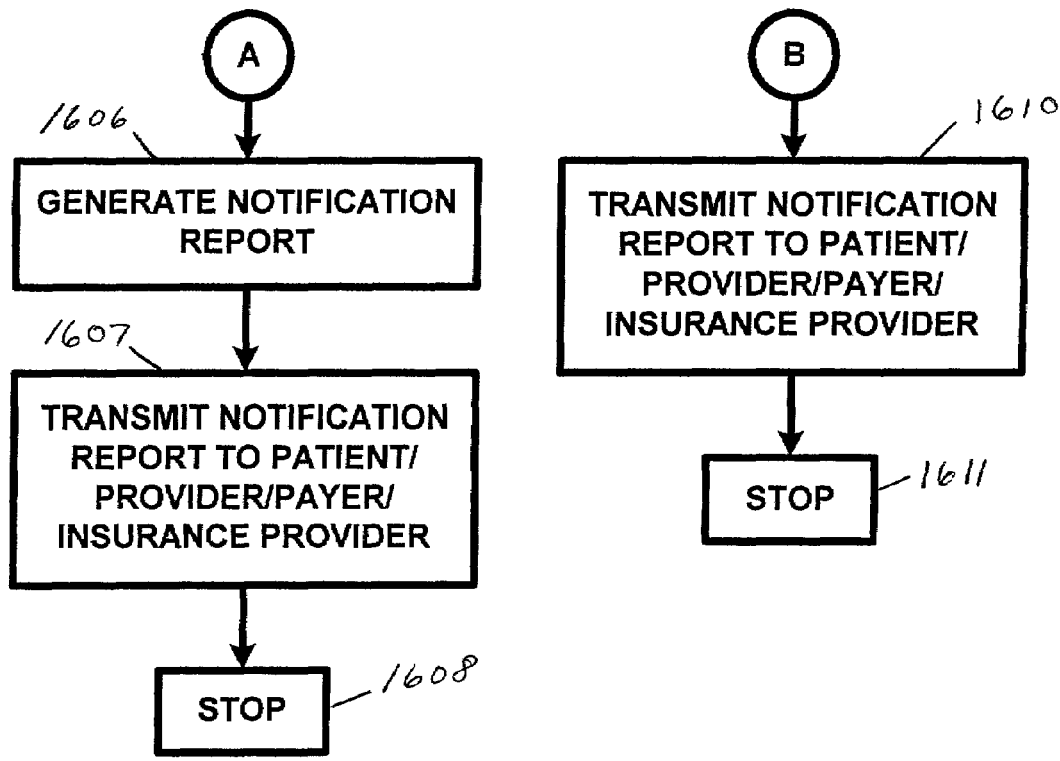

In another preferred embodiment, the apparatus 100 and method of the present invention can provide notification to a patient or individual when his or her healthcare record(s) or file(s), or any portion thereof, has been accessed, obtained, changed, altered, updated, and/or other modified, and/or when a request has been made to access, obtain, change, alter, update, and/or otherwise modify, his or her healthcare record(s) or file(s), or any portion thereof. FIGS. 16A and 16B illustrate another preferred embodiment method for utilizing the apparatus 100 of the present invention, in flow diagram form.

With reference to FIGS. 16A and 16B, the operation of the apparatus commences at step 1600. At step 1601, any one or more of a healthcare provider, a healthcare payer, an insurance provider, a patient, an individual, a relative of a patient or individual, and/or any other third party individual or entity (hereinafter referred to as "user") can access the central processing computer 10 via a respective computer or communication device and/or via their or its respective computer or communication device.

For example, a healthcare provider can access the central processing computer in order to access, obtain, change, alter, or modify, information contained in a patient's healthcare record(s) or file(s) for any appropriate reason, such as, but not limited to, updating a record or file, making a diagnosis, prescribing a treatment, providing a treatment plan or program, providing information to other providers, submitting insurance claim information, etc., and/or for any other reason.

A healthcare payer or insurance provider can provider can access the central processing computer in order to access, obtain, change, alter, or modify, information contained in a patient's healthcare record(s) or file(s) for any appropriate reason, such as but not limited to, processing an insurance claim, obtaining additional information regarding the patient or individual, etc., and/or for any other reason.

A patient or individual can access, obtain, change, alter, or modify, information contained in a patient's healthcare record(s) or file(s) for any appropriate reason, such as, but not limited to, updating a healthcare record or file, providing information to a healthcare provider, providing information to a healthcare payer or insurance provider, obtaining treatment information, obtaining healthcare provider information, obtaining healthcare payer information, obtaining provider information, obtaining insurance provider information, etc., and/or for any other reason.

A third party individual or entity can also access, obtain, change, alter, or modify, information contained in a patient's healthcare record(s) or file(s) for any appropriate reason, such as, but not limited to, updating a healthcare record or file, providing information regarding a patient or patients, providing information regarding an individual or individuals, providing information to a healthcare provider, providing information to a healthcare payer or insurance provider, obtaining treatment information, obtaining healthcare provider information, obtaining healthcare payer information, obtaining provider information, obtaining insurance provider information, etc., and/or for any other reason.

At step 1602, the user can enter identification information, a password, an electronic signature, a code, and/or any other information which may be needed for accessing the data and/or information stored in the central processing computer 10. The identification information can be entered by the user and/or be provided by the user's computer or communication device. At step 1602, the user can also enter an information request and/or a request to access, obtain, change, alter, or modify, information contained in a patient's healthcare record(s) or file(s). At step 1602, the user's identification information and information regarding the user's request can also be transmitted to the central processing computer 10.

At step 1603, the central processing computer 10 will receive and process the user's identification information and information regarding the user's request. At step 1604, the central processing computer 10 will determine whether the user is an authorized user. At step 1604, the central processing computer 10 can also determine whether the user is authorized to access, obtain, change, alter, or modify, the requested patient healthcare record(s) or file(s) and/or whether the user is authorized to access, obtain, change, alter, or modify, the requested information contained in a patient's healthcare record(s) or file(s). If, at step 1604, the central processing computer 10 determines that the user is an authorized user and/or that the user is authorized to access, obtain, change, alter, or modify, the requested healthcare record(s) or file(s), the operation of the apparatus 100 will proceed to step 1605.

At step 1605, central processing computer 10 will provide the requested information and/or the information in requested healthcare record(s) or file(s) to the user. At step 1605, the user can any one or more of access any information contained in the respective healthcare record(s) or file(s), obtain any information contained in the respective healthcare record(s) or file(s), change any information contained in the respective healthcare record(s) or file(s), alter any information contained in the respective healthcare record(s) or file(s), update any information contained in the respective healthcare record(s) or file(s), and/or modify any information contained in the respective healthcare record(s) or file(s).

For example, a healthcare provider can obtain patient information, update a patients record(s) or file(s), submit an insurance claim, prescribe a treatment for the patient, and/or perform any other task on, or involving the information contained in the patient's healthcare record(s) or file(s). A patient or individual can update his or her own healthcare record(s) or file(s) information, such as by providing medical, dental, or healthcare history, symptoms, etc. A healthcare payer or insurance provider can update claim information, obtain information for processing and/or analyzing insurance claims, and/or perform any other task.

At step 1605, the respective user can obtain, access, change, alter, or modify, any of the information contained in the patient's healthcare record(s) or file(s), for which the user is authorized. At step 1605, the respective user can perform any task on, or regarding, the information contained in the patient's healthcare record(s) or file(s).

At step 1606, the central processing computer 10 will generate a notification report containing information regarding the user who or which obtained, accessed, changed, altered, or modified, the healthcare record(s) or file(s), user identification information, the time and date the user obtained, accessed, changed, altered, or modified, the healthcare record(s) or file(s), the reason for the user obtaining, accessing, changing, altering, or modifying, the healthcare record(s) or file(s), the nature of any changes, alterations, or modifications, made to the information contained in the healthcare record(s) or file(s), the subject of, and/or the actual, changes, alterations, or modifications, made to the healthcare record(s) or file(s), and/or any other information regarding the user's obtaining, accessing, changing, altering, or modifying, the information contained in the healthcare record(s) or file(s).

At step 1607, the central processing computer 10 will transmit the notification report to the patient or individual whose healthcare record(s) or file(s) were accessed by the user. The notification report can be transmitted as an e-mail message, as a beeper message, as a pager message, as a telephone call, as a pre-recorder telephone call message, as an electronic transmission, and/or as any other information transmission or message. The notification report can be transmitted to the patient, to the patient computer 40, and/or to a patient communication device.

At step 1607, the notification report can also be transmitted to the patient's healthcare provider or healthcare providers, to the patient's healthcare payer or healthcare payers, to the patient's insurance provider or insurance providers, and/or to any third party individuals or entities authorized to receive the notification report. The notification report can be transmitted to any of the respective computers or communication devices associated with the respective healthcare provider(s), healthcare payer(s), insurance provider(s), and/or third party individual(s), entity, or entities.

Thereafter, the operation of the apparatus 100 will cease at step 1608.

If, however, at step 1604, it is determined that the user is not an authorized user and/or that the user is not authorized to access, obtain, change, alter, or modify, the requested healthcare record(s) or file(s), or any information contained therein, then the operation of the apparatus 100 will proceed to step 1609.

At step 1609, the central processing computer 10 will generate a notification report containing information regarding the user who or which attempted to obtain, access, change, alter, or modify, the healthcare record(s) or file(s), user identification information, the time and date of the user's attempted access of the healthcare record(s) or file(s), the reason for the user's attempted access of the healthcare record(s) or file(s), and/or any other information regarding the user's attempted access of the healthcare record(s) or file(s).

At step 1610, the central processing computer 10 will transmit the notification report to the patient or individual whose healthcare record(s) or file(s) were attempted to be accessed by the user. The notification report can be transmitted as an e-mail message, as a beeper message, as a pager message, a physical letter/mail delivery, as a telephone call, as a pre-recorder telephone call message, as an electronic transmission, and/or as any other information transmission or message. The notification report can be transmitted to the patient, to the patient computer 40, and/or to a patient communication device.

At step 1610, the notification report can also be transmitted to the patient's healthcare provider or healthcare providers, to the patient's healthcare payer or healthcare payers, to the patient's insurance provider or insurance providers, and/or to any third party individuals or entities authorized to receive the notification report. The notification report can be transmitted to any of the respective computers or communication devices associated with the respective healthcare provider(s), healthcare payer(s), insurance provider(s), and/or third party individual(s), entity, or entities.

Any of the notification reports described herein as being provided by the apparatus 100 of FIGS. 16A and 16B can be transmitted to the respective patient, individual, healthcare provider, healthcare payer, insurance provider, and/or third party, in real-time, in a time-delayed manner, and/or in any other appropriate manner.

Thereafter, the operation of the apparatus 100 will cease at step 1611.

In another preferred embodiment of FIGS. 16A and 16B, a respective patient, individual, healthcare provider, healthcare payer, insurance provider, and/or third party, upon receiving notification that an individual or entity is any one or more of accessing, obtaining, changing, altering, and/or modifying, information contained in a healthcare record or file, can terminate the accessing, obtaining, changing, altering, and/or modifying, information contained in a healthcare record or file, in real-time, such as by transmitting a "terminate" or "deny access" message or signal to the central processing computer 10 via a respective computer or communication device.

In another preferred embodiment, the apparatus 100 of FIGS. 16A and 16B, and in particular, the central processing computer 10, can store information regarding any accessing, obtaining, changing, altering, and/or modifying, of any of the information contained in any of the healthcare records and/or healthcare files by any of the herein-described healthcare providers, healthcare payers, insurance providers, patients, individuals and/or third parties.

The stored information can include any one or more of the data, time, reason, purpose, and/or the nature of the accessing, obtaining, changing, altering, and/or modifying, of any of the information contained in any of the healthcare records and/or healthcare files by any of the herein-described healthcare providers, healthcare payers, insurance providers, patients, individuals and/or third parties. The stored information can also include the subject matter of any changes, alterations, and/or modifications, to the healthcare record(s) or file(s).

The central processing computer 10 can generate and/or provide activity reports regarding any accessing, obtaining, changing, altering, and/or modifying, of any of the information contained in any of the healthcare records and/or healthcare files by any of the herein-described healthcare providers, healthcare payers, insurance providers, patients, individuals and/or third parties. The central processing computer 10 can generate activity reports upon demand and/or upon request. The central processing computer 10 can also be programmed to generate activity reports periodically, such as daily, weekly, monthly, bi-monthly, quarterly, annually, and/or for any other time period.

The activity reports can include information regarding any number of healthcare records or files for any number of patients or individuals.

The central processing computer 10 can transmit the activity reports to the respective healthcare providers, healthcare payers, insurance providers, patients, individuals and/or third parties, by transmitting same to a respective computer or communication device associated with the respective healthcare provider(s), healthcare payer(s), insurance provider(s), patient(s), individual(s), third party, and/or third parties. The activity report can be transmitted as an e-mail message, as a beeper message, as a pager message, a physical letter/mail delivery, as a telephone call, as a pre-recorded telephone call message, as an electronic transmission, and/or as any other information transmission or message.

Any of the activity reports described herein as being provided by the apparatus 100 of FIGS. 16A and 16B can be transmitted to the respective patient, individual, healthcare provider, healthcare payer, insurance provider, and/or third party, in real-time, in a time-delayed manner, and/or in any other appropriate manner.

In another preferred embodiment, the apparatus 100 can be utilized in order to allow patients and individuals to restrict and/or limit access to their healthcare records or files. In this manner, the patient or individual can restrict access of information contained in his or her healthcare record(s) or file(s) to only certain healthcare providers, healthcare payers, healthcare insurance providers, individuals, and/or entities. In this manner, the patient or individual can restrict access to his or her healthcare record information or healthcare file information to his or her healthcare provider(s), to his or her healthcare payer(s), to his or her insurance provider(s), to his or her relatives, family members, spouse, next-of-kin, and/or any other designated individual, individuals, entity, or entities.

The patient or individual can also restrict access to, the ability to obtain, the ability to change, alter, or modify, any information contained in his or her healthcare record(s) or file(s) to only certain information, certain portions of information, certain subject matter. For example, a patient or individual can restrict a medical doctor's access to his or her dental records, dental files, psychological files, etc. A patient can restrict a healthcare payer's access to unrelated or irrelevant information. A patient or individual can also restrict a third party individual's access to certain information.

The patient or individual can restrict access to any of his or her healthcare record(s) or file(s), and/or to any portions or sections of same, by any of the herein-described healthcare providers, healthcare payers, insurance providers, and/or any third party individual or entities, to that extant that said restricted access can be is lawful and/or legal. The patient or individual can also restrict access to any of his or her healthcare record(s) or file(s), and/or to any portions or sections of same, by any of the herein-described healthcare providers, healthcare payers, insurance providers, and/or any third party individual or entities, to the extent sufficient or necessary in order to maintain confidentiality, to keep certain information secret or accessible to a select few, and/or to address patient privacy concerns.

The patient or individual can also limit access to information, by any of the herein-described healthcare providers, healthcare payers, insurance providers, and/or any third party individual or entities, to only certain information or sections of information contained in his or her healthcare record(s) or file(s), and/or to limit access to certain information or sections of information contained in his or her healthcare record(s) or file(s), for use for only specifically designated purposes.

For example, a patient or individual can limit a healthcare provider's access to certain medical history information only to the extent that said information can be utilized to perform a diagnosis for a certain ailment(s), illness, or symptom(s), and/or to allow for the submission of an insurance claim, and/or for any other reason. A patient or individual can also, for example, limit an healthcare payer's or an insurance provider's access to certain information to the extent of verifying or disproving certain conditions, pre-existing conditions, to process an insurance claim submission, and/or for any other reason.

Figure 17A:
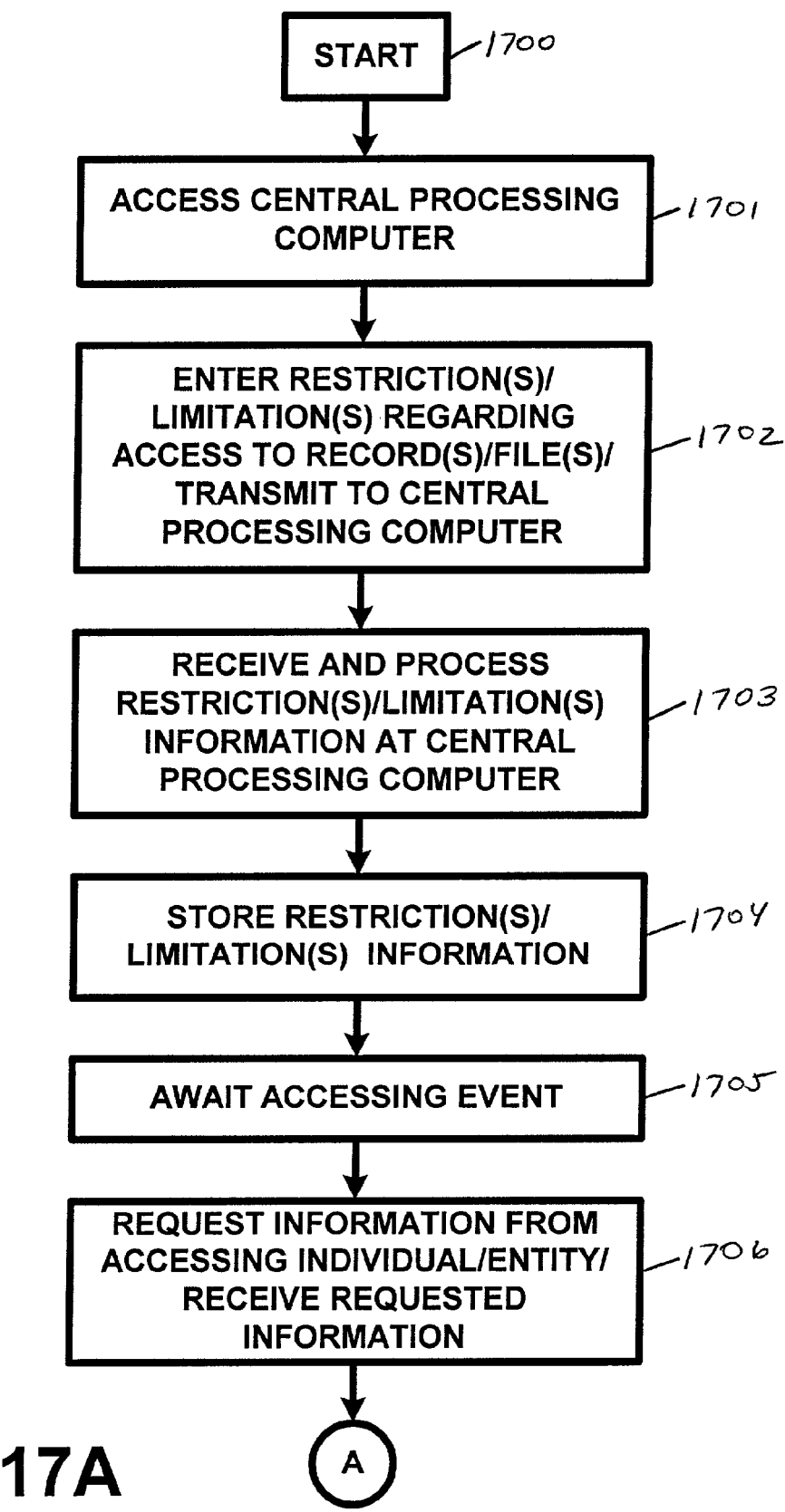
FIGS. 17A and 17B illustrate another preferred embodiment method of using the present invention, in flow diagram form.
Figure 17B:
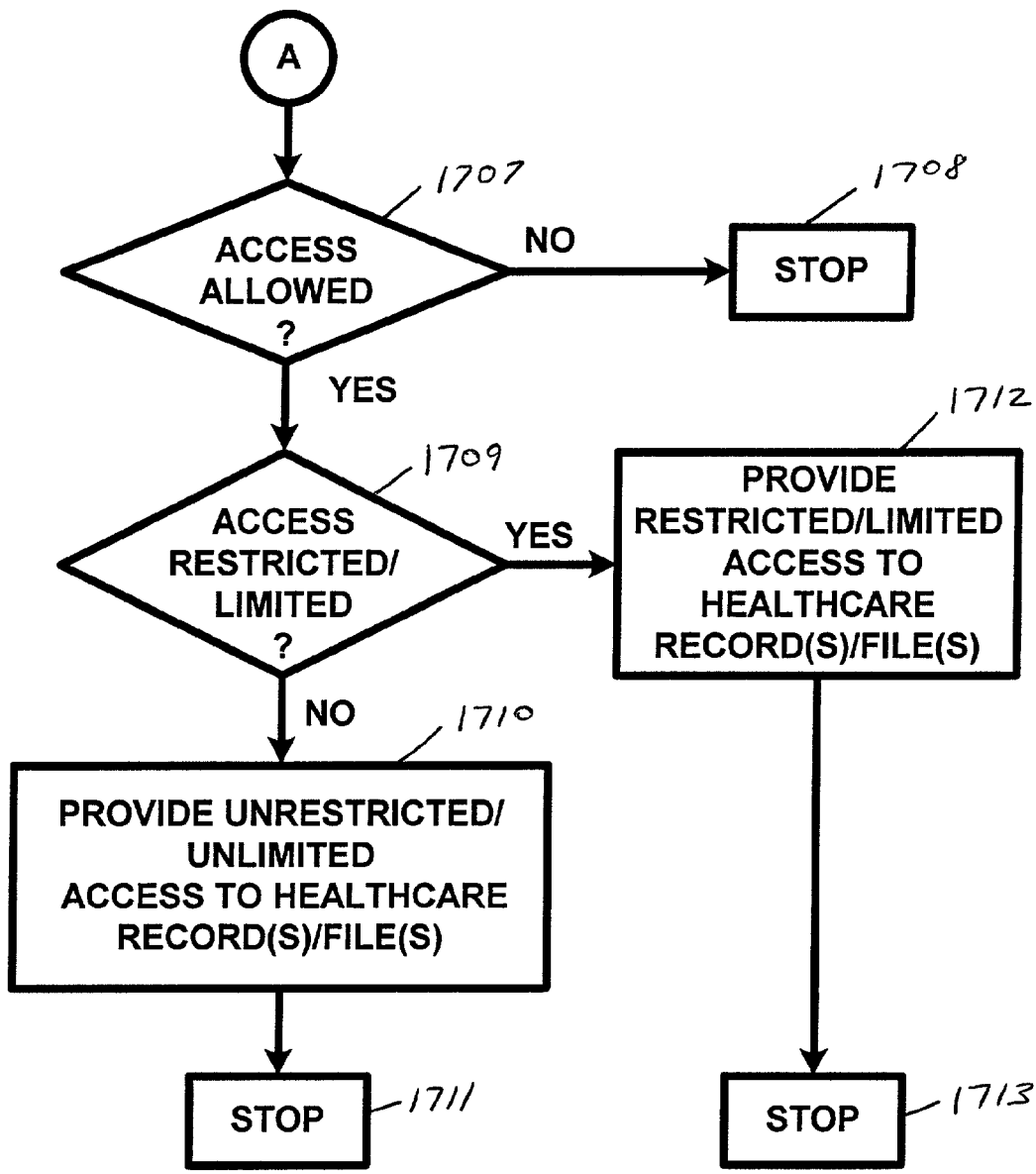

FIGS. 17A and 17B illustrate another preferred embodiment method of utilizing the apparatus 100 of the present invention in flow diagram form. With reference to FIGS. 17A and 17B, the operation of the apparatus 100 commences at step 1700. At step 1701, the patient or individual (hereinafter referred to as the "patient") can access the central processing computer 10 via his or her patient computer 40. At step 1702, the patient can enter information regarding the restrictions and/or limitations on the access to his or her healthcare record(s) or file(s).

At step 1702, the patient can enter information regarding any restrictions and/or limitations to the access to his or her healthcare record(s) or file(s) to only a certain healthcare provider(s), a certain type of healthcare provider(s), to a certain healthcare payer(s), a certain type of healthcare payer(s), a certain insurance provider(s), a certain type of insurance provider(s), a certain individual(s), third party, or third parties.

At step 1702, the patient can also restrict and/or limit access to his or her healthcare record(s) or file(s), or any information and/or portions of information contained in his or her healthcare record(s) or file(s), for only certain designated purposes (i.e. diagnosis, second opinions, insurance claims submission, insurance claims processing, etc.).

The patient can also restrict and/or limit access to his or her healthcare record(s) or file(s), or any information and/or portions of information contained in his or her healthcare record(s) or file(s), to certain times, days, dates, or other designated times. The patient can also restrict and/or limit access to his or her healthcare record(s) or file(s), or any information and/or portions of information contained in his or her healthcare record(s) or file(s), until such time as certain pre-conditions are met.

For example, the pre-condition can be the establishment of a doctor-patient relationship, the establishment of an insured-insurer relationship, the establishment of a family or next-of-kin relationship, and/or the satisfaction of any condition or pre-condition which can be defined by, or dictated by, any of the herein-described patients, healthcare providers, healthcare payers, insurance providers, and/or third parties). The patient can also restrict or limit the ability of a healthcare provider, a healthcare payer, an insurance provider, a patient, an individual, and/or a third party, to obtain, access, change, alter, or modify, any information contained in the patient's healthcare record(s) or file(s).

The patient can enter any other restriction or limitations to access to his or her healthcare record(s) or file(s), and/or to any information and/or portions of information contained therein, at step 1702.

At step 1702, the restriction or limitation information can be transmitted to the central processing computer 10. At step 1703, the central processing computer 10 will receive and process the restriction and/or limitation information in conjunction with the patient's healthcare record(s) or file(s). At step 1704, the central processing computer 10 will store the restriction or limitation information in the database 10H.

At step 1705, the apparatus 100 will await the accessing of the central processing computer 10 by any individual, healthcare provider, healthcare payer, insurance provider, and/or any third party, who or which desires to access the patient's healthcare record(s) or file(s). Upon the attempted accessing of the patient's healthcare record(s) or file(s) by any of the herein-described individuals, healthcare providers, healthcare payers, insurance providers, and/or any third parties, the operation of the apparatus 100 will proceed to step 1706. At step 1706, the apparatus 100 and/or the central processing computer 10 can request information from the individual, healthcare provider, healthcare payer, insurance provider, and/or any third party, who or which desires to access the patient's healthcare record(s) or file(s).

The requested information can include the name or identity of the individual, healthcare provider, healthcare payer, insurance provider, and/or any third party, the type, nature, or credentials, of the individual, healthcare provider, healthcare payer, insurance provider, and/or third party, the nature or purpose of the requested access of the patient's healthcare record(s) or file(s), information regarding the satisfaction and/or the existence of any conditions or pre-conditions to access of the patient's healthcare record(s) or file(s) and/or to any information and and/or sections of information contained in the healthcare record(s) or file(s).

At step 1706, the central processing computer 10 can receive the individual's, the healthcare provider's, the healthcare payer's, the insurance provider's, and/or the third party's, response(s) to the requested information. At step 1707, the central processing computer 10 will determine if the individual's, the healthcare provider's, the healthcare payer's, the insurance provider's, and/or the third party's, access is allowed.

If, at step 1707, it is determined that the individual's, the healthcare provider's, the healthcare payer's, the insurance provider's, and/or the third party's, access is not allowed the operation of the apparatus 100 will cease at step 1708. If, at step 1707, it is determined that the individual's, the healthcare provider's, the healthcare payer's, the insurance provider's, and/or the third party's, access is allowed, the operation of the apparatus 100 will proceed to step 1709.

At step 1709, the central processing computer 10 will determine whether the individual's, the healthcare provider's, the healthcare payer's, the insurance provider's, and/or the third party's, access is restricted or limited. If, at step 1709, it is determined that the individual's, the healthcare provider's, the healthcare payer's, the insurance provider's, and/or the third party's, access is not restricted or not limited, then the operation of the apparatus 100 will proceed to step 1710. At step 1710 the apparatus 100 and/or the central processing computer 10 will provide the respective individual, healthcare provider, healthcare payer, insurance provider, and/or the third party, with unrestricted and/or with unlimited access to the patient's healthcare record(s) or file(s). Thereafter, the operation of the apparatus will cease at step 1711.

If, at step 1709, it is determined that the individual's, the healthcare provider's, the healthcare payer's, the insurance provider's, and/or the third party's, access is restricted or is limited, then the operation of the apparatus 100 will proceed to step 1712. At step 1712, the apparatus 100 and/or the central processing computer 10 will provide the respective individual, healthcare provider, healthcare payer, insurance provider, and/or the third party, with the restricted and/or with the limited access to the patient's healthcare record(s) or file(s). Thereafter, the operation of the apparatus will cease at step 1713.

In any and/or all of the embodiments described herein, any patient, provider, payer, user, and/or intermediary can access any one or more of the central processing computer(s) 10, the providers communication devices (20), the payer communication devices 30, the patient communication devices 40, and/or the intermediate communication devices 50, via any one or more of the said computers and/or communication devices 10, 20, 30, 40, and/or 50, as well as via any computer and/or communication device. In this manner, any of the herein-described parties can access the present invention from any computer and/or communication device. Public kiosks with links to any of the computers and/or communication devices 10, 20, 30, 40, and/or 50, can also be utilized to access and utilize the present invention and/or any of the computers and/or communication devices described herein.

In any and/or all of the embodiments described herein, access to any and/or all of the data, information, records, files, etc., which is stored in any of the databases 10H, 20H, 30H, 40H, and/or 50H, can be restricted to preserve the security and confidentiality of same. Any of the patients, users, providers, payers, and/or intermediaries, can be provided with identification and/or other cards with any and/or all pertinent data regarding the respective individual and/or party provided on the card.

The identification card, in the preferred embodiment can contain a magnetic strip for storing any and/or all pertinent information, a "smart card" for storing information, and/or a bar code or bard codes for storing identification information as well as any other information described herein as being pertinent to the respective patient, user, provider, payer, and/or intermediary.

Each of the central processing computer(s) 10, the providers communication devices 20, the payer communication devices 30, the patient communication devices 40, and/or the intermediate communication devices 50, as well as any other computer and/or communication device, can include suitable devices for reading, scanning, and/or obtaining information which may be stored on the identification card. In this manner, access to the present invention, and the respective use thereof, can be facilitated by the above-described identification card(s).

In another preferred embodiment, as well as in any of the embodiments described herein, intelligent agents, software agents, mobile agents, and/or related technologies, can be utilized in conjunction with the present invention. The respective intelligent agent(s), software agent(s), mobile agent(s), (hereinafter referred to collectively as "intelligent agent" or "intelligent agents") can be programmed and/or designed to act on behalf of the respective patients, users, providers, payers, and/or intermediaries, so as to act on behalf of the respective party as well as to perform any of processing functions and/or other functions described herein.

The intelligent agent can act on behalf of the respective party in various related interactions and/or other activities which are described as being performed herein and/or which may be incidental and/or related thereto. Therefore, the present invention also provides an agent-based apparatus and method for providing healthcare information and/or healthcare-related information.

Applicant hereby incorporates by reference herein the subject matter of the *Agent Sourcebook, A Complete Guide to Desktop, Internet and Intranet Agents*, by Alper Caglayan and Colin Harrison, Wiley Computer Publishing, 1997. Applicant also incorporates by reference herein the subject matter of *Cool Intelligent Agents For The Net*, by Leslie L. Lesnick with Ralph E. Moore, IDG Books Worldwide, Inc. 1997.

The apparatus of the present invention, in any and/or all of the embodiments described herein, can also be programmed to be self-activating and/or activated automatically.

The apparatus of the present invention can also be programmed in order to automatically generate and/or transmit any of the e-mails, electronic message transmissions, electronic notification transmissions, and/or any of the communications, which are described herein, between any of the parties which utilize the present invention.

The present invention, in any and/or all of the herein-described embodiments, can utilize electronic commerce technologies and security methods, techniques and technologies, as described and as set forth in *Electronic Commerce Technical, Business, and Legal Issues*, Nabil R. Adam, et al. Prentice Hall, 1999 and *Web Security & Commerce*, Simson Garfinkel with Gene Spafford, O'Reilly 1997, the subject matter of which are hereby incorporated by reference herein.

The communications networks and/or systems on, or over, which the present invention may be utilized, can include any one or combination of telecommunication networks or systems, satellite communication networks or systems, radio communication networks or systems, digital communication networks or systems, digital satellite communication networks or systems, personal communications services networks or systems, cable television networks or systems, broadband communication networks or systems, low earth orbiting satellite (LEOs) networks or systems, wireless communication networks or systems, wireless Internet networks or systems, wireless World Wide Web networks or systems, as well as in, or on any internets and/or intranets, the Internet, the World Wide Web, and any other suitable communication network or system.

The data and/or information, described as being stored in the database 10H and/or in any of the other databases described herein, can be continuously updated so as to store the latest values for the data and/or information and can be stored and be made available for future processing routines.

Any and/or all of the data and/or information described herein, which is stored in the database 10H, or in the collection of databases, can be linked via relational database techniques and/or via any appropriate database management techniques. The data and/or information, in the preferred embodiments, can be updated via inputs from any of the computers and/or communication devices 10, 20, 30, 40, and/or 50, and/or external computers or communication devices, described herein, in real-time, and/or via dynamically linked database management techniques. The above-described updates can also be provided from other information sources via the communication network.

The data and/or information which is stored in the database 10H and/or which may be otherwise utilized with, and/or in conjunction with, the apparatus and method of the present invention, can be linked via any suitable data linking techniques such as, for example, dynamically linked lists (DLLs), linked lists, and object links embedded (OLE's). Any suitable database management technique(s) may also be utilized in conjunction with the present invention.

The present invention provides an apparatus and a method for providing comprehensive information in the healthcare fields and/or healthcare-related fields. The present invention also provides valuable services to the various parties who seek, provide, pay for, administer, and/or monitor healthcare services, goods and/or products as well as healthcare-related services, goods, and/or products.

The present invention can provide comprehensive and accurate information to any of the parties described herein so as to facilitate an improved healthcare system which can provide up-to-date patient, provider, payer, and/or intermediary, information. The present invention, by facilitating the creation and maintenance of a comprehensive database of information, which can be accessed on a global basis, at any time of day or night, and from any location, can provide patients, providers, payers, and/or intermediaries, with information which can improve healthcare treatments, reduce the likelihood of errors in diagnoses and/or prescribed treatments, reduce healthcare costs, reduce the likelihood of incorrect and/or fraudulent care, and can provide for a healthcare system which is characterized by an improved quality of care and cost efficiency.

In addition to any and/or all of the preferred embodiments described herein, the present invention can also be utilized in other preferred embodiments so as to incorporate, so as to improve upon, and/or so as to utilize, various teachings of the prior art. In this regard, Applicant hereby incorporates by reference herein the subject matter of the following U.S. Patents for their respective teachings: U.S Pat. No. 5,988,851 which teaches a medical treatment and or diagnostic system; U.S. Pat. No. 5,974,124 which teaches a methods and system aiding medical diagnosis and treatment; U.S. Pat. No. 5,961,448 which teaches a virtual medical instrument for performing medical diagnostic testing on patients; U.S. Pat. No. 5,957,854 which teaches a wireless medical diagnosis and monitoring equipment; U.S. Pat. No. 5,954,641 which teaches a method, apparatus and operating system for managing the administration of medication and medical treatment regimens; U.S. Pat. No. 5,935,060 which teaches a computerized medical diagnostic and treatment advice system including list based processing; U.S. Pat. No. 5,910,107 which teaches a computerized medical diagnostic and treatment advice method; U.S. Pat. No. 5,899,857 which teaches a medical treatment method with scanner input; U.S. Pat. No. 5,895,354 which teaches an integrated medical diagnostic center; U.S. Pat. No. 5,878,746 which teaches a computerized medical diagnostic system; U.S. Pat. No. 5,876,351 which teaches a portable modular diagnostic medical device; U.S. Pat. No. 5,868,669 which teaches a computerized medical diagnostic and treatment advice system; U.S. Pat. No. 5,862,803 which teaches a wireless medical diagnosis and monitoring system; U.S. Pat. No. 5,839,438 which teaches a computer-based neural network system and method for medical diagnosis and interpretation; U.S. Pat. No. 5,807,256 which teaches a medical information processing system for supporting diagnosis; U.S. Pat. No. 5,807,246 which a display device in medical examination and treatment system; U.S. Pat. No. 5,801,755 which teaches an interactive communication system for medical treatment of remotely located patients; U.S. Pat. No. 5,797,901 which teaches an automatic activation system for a medical diagnostic monitoring and surgical apparatus and method therefore; U.S. Pat. No. 5,779,634 which teaches a medical information processing system for supporting diagnosis; U.S. Pat. No. 5,776,057 which teaches a virtual medical instrument for performing medical diagnostic testing on patients; U.S. Pat. No. 5,761,334 which teaches an apparatus for computer aided diagnosis of medical images having abnormal patterns; U.S. Pat. No. 5,724,968 which teaches a computerized medical diagnostic system including meta function; U.S. Pat. No. 5,666,953 which teaches a system and associated method for providing information for use in forming medical diagnosis; U.S. Pat. No. 5,660,176 which teaches a computerized medical diagnostic and treatment advice system; U.S. Pat. No. 5,594,638 which teaches a computerized medical diagnostic system including re-enter function and sensitivity factors; U.S. Pat. No. 5,583,758 which teaches a health care management system for managing medical treatments and comparing user-proposed and recommended resources required for treatment; U.S. Pat. No. 5,551,436 which teaches a medical diagnosis system; U.S. Pat. No. 5,544,651 which teaches a medical system and associated method for automatic treatment; U.S. Pat. No. 5,437,278 which teaches medical diagnosis system and method; U.S. Pat. No. 5,415,167 which teaches a medical system and associated method for automatic diagnosis and treatment; U.S. Pat. No. 5,360,005 which teaches a medical diagnosis device for sensing cardiac activity and blood flow; U.S. Pat. No. 5,331,550 which teaches an application of neural networks as an aid in medical diagnosis and general anomaly detection; U.S. Pat. No. 5,324,077 which teaches a medical data draft for tracking and evaluating medical treatment; U.S. Pat. No. 5,305,748 which teaches a medical diagnostic system and related method; U.S. Pat. No. 5,279,294 which teaches a medical diagnostic system; U.S. Pat. No. 5,255,187 which teaches a computer aided medical diagnostic method and apparatus; U.S. Pat. No. 5,235,510 which teaches a computer-aided diagnosis system for medical use; U.S. Pat. No. 5,090,417 which teaches a medical diagnostic apparatus; U.S. Pat. No. 4,733,354 which teaches a method and apparatus for automated medical diagnosis using decision tree analysis; U.S. Pat. No. 4,731,725 which teaches a data processing system which suggests a pattern of medical tests to reduce the number of tests necessary to confirm or deny a diagnosis; U.S. Pat. No. 4,674,512 which teaches a medical electrode for monitoring and diagnostic use; U.S. Pat. No. 4,674,108 which teaches a digital X-ray medical diagnostic apparatus; U.S. Pat. No. 4,641,659 which teaches a medical diagnostic microwave scanning apparatus; U.S. Pat. No. 4,290,114 which teaches a medical diagnostic computer; U.S. Pat. No. 4,251,850 which teaches a control desk for medical apparatus, in particular for an x-ray diagnostic apparatus; U.S. Pat. No. 4,242,911 which teaches an ultrasonic medical diagnostic apparatus and method; U.S. Pat. No. 4,235,454 which teaches a stabilization system for a medical diagnostic device; U.S. Pat. No. 4,209,022 which teaches an echography apparatus for medical diagnosis, using a multiple-element probe; U.S. Pat. No. 4,170,987 which teaches a medical diagnosis system and method with multispectral imaging; U.S. Pat. No. 4,110,723 which teaches an ultrasonic apparatus for medical diagnosis; and U.S. Pat. No. 3,978,850 which teaches medical diagnostic instruments.

While the present invention has been described and illustrated in various preferred and alternate embodiments, such descriptions are merely illustrative of the present invention and are not to be construed to be limitations thereof. In this regard, the present invention encompasses all modifications, variations and/or alternate embodiments, with the scope of the present invention being limited only by the claims which follow.

What is claimed is:

1. An apparatus, comprising:
   a processor, wherein the processor processes a request to at least one of access, obtain, change, alter, and modify, information contained in a patient's healthcare record or a patient's healthcare file of a patient, wherein the processor determines whether an individual or entity is authorized to at least one of access, obtain, change, alter, and modify, the information contained in a patient's healthcare record or a patient's healthcare file, and further wherein the processor generates a notification report containing at least one of information regarding the individual or entity making the request, identification information regarding the individual or entity, and a time and date of the request, and further wherein the notification_report contains an actual change, alteration, or modification, sought to be made or made to the information contained in a patient's healthcare record or a patient's healthcare file; and
   a transmitter, wherein the transmitter transmits the notification report to a patient communication device of the patient via, on, or over, a communication network, and further wherein the notification report is transmitted to the patient communication device at least one of during, concurrently with, at a same time as, and prior to a completion of, at least one of an accessing, an obtaining, a changing, an altering, and a modifying, of the information contained in a patient's healthcare record or a patient's healthcare file by the individual or entity, or at least one of during, concurrently with, at a same time as, and prior to a completion of, a processing of the request.

2. A computer-implemented method, comprising:
   processing, with a processor, a request by a person or an entity to at least one of access, obtain, change, alter, and modify, information contained in an individual's or patient's healthcare record or an individual's or patient's healthcare file of the individual or patient wherein the individual's or patient's healthcare record or the individual's or patient's healthcare file of the individual or patient contains healthcare information or healthcare-related information personal to the individual or patient;
   generating a message containing at least one of information regarding the person or the entity making the request and identification information regarding the person or the entity making the request, and further wherein the message contains an actual change, alteration, or modification, sought to be made or made to the information contained in an individual's or patient's healthcare record or an individual's or patient's healthcare file; and
   transmitting the message to a communication device of the individual or patient via, on, or over, a communication network, wherein the message is transmitted to the communication device of the individual or patient at least one of during, concurrently with, at a same time as, and prior to a completion of, at least one of an accessing, an obtaining, a changing, an altering, and a modifying, of the information contained in an individual's or patient's healthcare record or an individual's or patient's healthcare file by the person or the entity, or at least one of during, concurrently with, at a same time as, and prior to a completion of, a processing of the request to at least one of access, obtain, change, alter, and modify, the information contained in an individual's or patient's healthcare record or an individual's or patient's healthcare file.

3. The computer-implemented method of claim 2, further comprising:
   receiving a response to the message, wherein the response to the message is transmitted from the communication device of the individual or patient, and further wherein the response to the message contains information for terminating or denying at least one of an accessing, an obtaining, a changing, an altering, and a modifying, of the information contained in an individual's or patient's healthcare record or an individual's or patient's healthcare file; and
   terminating or denying the request to at least one of access, obtain, change, alter, and modify, the information contained in an individual's or patient's healthcare record or an individual's or patient's healthcare file.

4. The computer-implemented method of claim 2, further comprising:
   receiving information regarding an examination finding or a symptom, wherein the information regarding an examination finding or a symptom is transmitted from a computer or communication device associated with a healthcare provider of the individual or patient;
   at least one of storing and processing the information regarding an examination finding or a symptom; and
   updating the information contained in an individual's or patient's healthcare record or an individual's or patient's healthcare file to include the information regarding an examination finding or a symptom.

5. The computer-implemented method of claim 4, wherein the information regarding an examination finding or a symptom contains information obtained with or by at least one of a heart rate monitor or measurement device, a thermometer, a blood pressure monitor or measurement device, a blood analysis device or machine, a respiration monitoring or measurement device, a dialysis machine, an electrocardiograph (EKG) machine or device, an electrocephalograph (EEG) machine or device, an electromyograph (EMG) machine or device, a magnetic resonance imaging (MRI) machine or device, an X-ray machine or device, a thermal imaging machine or device, a laprascopic device, an arthroscopic device, a catheter device, a sonogram imaging device, a sonograph device, an ultrasound imaging device, an ultrasound measurement device, a CAT SCAN device, a mammogram device, a carbon dioxide detection or measurement device, a carbon monoxide detection or measurement device, a transvascular impedence measurement or monitoring device, an ultrasonic imaging device, a bone conduction device, a brain function scan analyzer device, a fetal heart rate measurement, monitoring, or probing, device, an endotrachial cardiac monitoring device, a surgical instrument, a blood oxygen detection device, an esophageal probing device, a sphygmomanometer, a differential doppler device, a camera probing device, and a microscopic camera probing device.

6. The computer-implemented method of claim 4, further comprising:

performing a diagnostic evaluation of the individual or patient using the information regarding an examination finding or a symptom;

generating a second message in response to the diagnostic evaluation, wherein the second message contains a diagnosis or a list of possible diagnoses;

transmitting the second message to the computer or communication device associated with a healthcare provider of the individual or patient or to a second computer or second communication device associated with the healthcare provider of the individual or patient; and updating the information contained in an individual's or patient's healthcare record or an individual's or patient's healthcare file to include information contained in the second message.

7. The computer-implemented method of claim 6, further comprising:

generating a third message in response to the diagnostic evaluation, wherein the third message contains information regarding a treatment or a treatment plan corresponding to the diagnosis or the list of possible diagnoses;

transmitting the third message to the computer or communication device associated with a healthcare provider of the individual or patient or to a second computer or second communication device associated with the healthcare provider of the individual or patient; and updating the information contained in an individual's or patient's healthcare record or an individual's or patient's healthcare file to include information contained in the third message.

8. The computer-implemented method of claim 2, further comprising:

receiving information regarding a treatment to be administered to the individual or patient or a procedure to be performed on the individual or patient, wherein the information regarding a treatment to be administered to the individual or patient or a procedure to be performed on the individual or patient is transmitted from a computer or communication device located at least one of at a healthcare facility, at a location of a treatment, and at a location of a procedure;

processing the information regarding a treatment to be administered to the individual or patient or a procedure to be performed on the individual or patient using the information contained in an individual's or patient's healthcare record or an individual's or patient's healthcare file;

determining whether or not the treatment to be administered to the individual or patient or the procedure to be performed on the individual or patient is correct;

generating a second message containing information regarding whether or not the treatment to be administered to the individual or patient or the procedure to be performed on the individual or patient is correct, and, if the treatment to be administered to the individual or patient or the procedure to be performed on the individual or patient is determined to be not correct, the second message contains information regarding a correct treatment or a correct procedure; and transmitting the second message to the computer or communication device located at least one of at a healthcare facility, at a location of a treatment, and at a location of a procedure.

9. The computer-implemented method of claim 2, further comprising:

determining whether a diagnosis is appropriate or valid or determining whether a treatment or treatment plan corresponding to a diagnosis is appropriate or valid;

generating a second message containing information regarding whether a diagnosis is appropriate or valid or whether a treatment or treatment plan corresponding to a diagnosis is appropriate or valid; and transmitting the second message to a computer or communication device associated with a healthcare insurer or a healthcare payer of the individual or patient.

10. The computer-implemented method of claim 2, wherein the communication device of the individual or patient is a wireless device, and further wherein the message is transmitted to the communication device of the individual or patient via, on, or over, at least one of the Internet, the World Wide Web, and a wireless communication network.

11. The computer-implemented method of claim 2, further comprising:

transmitting the message to a computer or communication device associated with a healthcare provider of the individual or patient.

12. The computer-implemented method of claim 2, further comprising:

transmitting the message to a computer or communication device associated with a healthcare insurer or a healthcare payer of the individual or patient.

13. The computer-implemented method of claim 2, further comprising:

generating a second message containing information regarding an occurrence of an admitting of the individual or patient to a hospital or a healthcare facility or containing information regarding a diagnosis regarding the individual or patient; and transmitting the second message to a computer or communication device associated with a healthcare provider of the individual or patient.

14. The computer-implemented method of claim 2, further comprising:

generating a second message containing information regarding an occurrence of an admitting of the individual or patient to a hospital or a healthcare facility or containing information regarding a diagnosis regarding the individual or patient; and transmitting the second message to a computer or communication device associated with a healthcare insurer or a healthcare payer of the individual or patient.

15. The computer-implemented method of claim 2, further comprising:

generating a second message containing information regarding an insurance claim for submission to a healthcare insurer or a healthcare payer of the individual or patient, wherein the second message is automatically generated in response to an updating of the information contained in an individual's or patient's healthcare record or an individual's or patient's healthcare file; and transmitting the second message to a computer or communication device associated with a healthcare insurer or a healthcare payer of the individual or patient.

16. The computer-implemented method of claim 2, wherein the message contains at least one of information regarding the person or the entity making the request, a time and date of the request, a reason for the request, and at least one of information regarding a nature of a change, alteration, or modification, sought to be made or made to the information contained in an individual's or patient's healthcare record or an individual's or patient's healthcare file and information regarding a subject of a change, alteration, or modification, sought to be made or made to the information contained in an individual's or patient's healthcare record or an individual's or patient's healthcare file.

17. The computer-implemented method of claim 2, further comprising:
receiving and storing information for updating the information contained in an individual's or patient's healthcare record or an individual's or patient's healthcare file, wherein the information for updating the information contained in an individual's or patient's healthcare record or an individual's or patient's healthcare file is transmitted from the communication device of the individual or patient or transmitted from a second communication device of or used by the individual or patient.

18. The computer-implemented method of claim 2, further comprising:
receiving and storing information for updating the information contained in an individual's or patient's healthcare record or an individual's or patient's healthcare file, wherein the information for updating the information contained in an individual's or patient's healthcare record or an individual's or patient's healthcare file is transmitted from a communication device or computer associated with a healthcare provider of the individual or patient; and
updating the information contained in an individual's or patient's healthcare record or an individual's or patient's healthcare file.

19. The computer-implemented method of claim 2, further comprising:
generating an activity report containing information regarding at least one of an accessing, an obtaining, a changing, an altering, and a modifying, of the information contained in an individual's or patient's healthcare record or an individual's or patient's healthcare file, during a time period, wherein the activity report is generated automatically or in response to a request to receive an activity report; and
transmitting the activity report to at least one of the communication device of the individual or patient, a computer or second communication device associated with the individual or patient, a computer or communication device associated with a healthcare provider of the individual or patient, and a computer or communication device associated with a healthcare insurer or a healthcare payer of the individual or patient.

20. A computer-implemented method, comprising:
receiving information regarding a restriction or limitation regarding an ability of a person or an entity to at least one of access, obtain, change, alter, and modify, information contained in an individual's or patient's healthcare record or an individual's or patient's healthcare file, wherein the individual's or patient's healthcare record or the individual's or patient's healthcare file contains healthcare information or healthcare-related information personal to the individual or patient, wherein the restriction or limitation contains information regarding at least one of a healthcare provider, a healthcare payer, a healthcare insurer, and an authorized entity, and information regarding a designated purpose for allowing each of the at least one of a healthcare provider, a healthcare payer, a healthcare insurer, and an authorized entity, to at least one of access, obtain, change, alter, and modify, the information contained in an individual's or patient's healthcare record or an individual's or patient's healthcare file, wherein the designated purpose is at least one of to perform a diagnosis, to perform a diagnosis for a certain ailment, illness, or symptom, to provide a second opinion, to verify or disprove a condition or a pre-existing condition, to submit an insurance claim, and to process an insurance claim;
storing the information regarding a restriction or limitation regarding an ability of a person or an entity to at least one of access, obtain, change, alter, and modify, the information contained in an individual's or patient's healthcare record or an individual's or patient's healthcare file;
processing, with a processor, a request by a person or an entity to at least one of access, obtain, change, alter, and modify, the information contained in an individual's or patient's healthcare record or an individual's or patient's healthcare file;
determining, using the information regarding the restriction or limitation, whether the person or the entity is allowed or authorized to at least one of access, obtain, change, alter, and modify, the information contained in an individual's or patient's healthcare record or an individual's or patient's healthcare file;
generating a message containing at least one of information regarding the person or the entity making the request, and identification information regarding the person or the entity making the request, and further wherein the message contains an actual change, alteration, or modification, made to the information contained in an individual's or patient's healthcare record or an individual's or patient's healthcare file; and
transmitting the message to a communication device of the individual or patient via, on, or over, a communication network, wherein the message is transmitted to the communication device of the individual or patient at least one of during, concurrently with, at a same time as, and prior to a completion of, an at least one of an accessing, an obtaining, a changing, an altering, and a modifying, of the information contained in an individual's or patient's healthcare record or an individual's or patient's healthcare file by the person or the entity, or at least one of during, concurrently with, at a same time as, and prior to a completion of, a processing of the request to at least one of access, obtain, change, alter, and modify, the information contained in an individual's or patient's healthcare record or an individual's or patient's healthcare file.

21. The computer-implemented method of claim 2, further comprising:
storing information regarding a schedule of a healthcare provider;
receiving information regarding an appointment made by the individual or patient with the healthcare provider; and
updating the information regarding a schedule of the healthcare provider to include the information regarding an appointment made by the individual or patient with the healthcare provider.

22. The computer-implemented method of claim 21, further comprising:
transmitting a second message to the communication device of the individual or patient, wherein the second message contains information confirming the appointment made by the individual or patient with the healthcare provider or containing information reminding the individual or patient of the appointment made by the individual or patient with the healthcare provider.

23. The computer-implemented method of claim 2, further comprising:
storing information regarding a schedule of a healthcare provider;
receiving information regarding an appointment made by a second individual or second patient with the healthcare provider; and
updating the information regarding a schedule of the healthcare provider to include the information regarding an appointment made by the second individual or second patient with the healthcare provider.

24. The computer-implemented method of claim 2, further comprising:
receiving a request from the individual or patient or from a second individual or second patient to locate a healthcare provider or a healthcare facility for the individual or patient or for the second individual or second patient;
identifying a healthcare provider or a healthcare facility in response to the request to locate a healthcare provider or a healthcare facility for the individual or patient or for the second individual or second patient;
generating a second message containing information regarding a healthcare provider or a healthcare facility responsive to the request to locate a healthcare provider or a healthcare facility for the individual or patient or for the second individual or second patient; and
transmitting the second message to the communication device of the individual or patient or to a second communication device of the individual or patient or of the second individual or second patient.

25. The computer-implemented method of claim 2, further comprising:
receiving a request to locate a supply, medication, body organ, or blood;
generating a second message containing information regarding a located supply, medication, body organ, or blood, in response to the request to locate a supply, medication, body organ, or blood; and
transmitting the second message to the communication device of the individual or patient or to a second communication device of the individual or patient or of a second individual or second patient.

26. The computer-implemented method of claim 2, further comprising:
receiving a request to locate a healthcare insurer or a healthcare payer; generating a second message containing information regarding a located healthcare insurer or healthcare payer in response to the request to locate a healthcare insurer or a healthcare payer; and
transmitting the second message to the communication device of the individual or patient or to a second communication device of the individual or patient or of a second individual or second patient.

27. The computer-implemented method of claim 2, further comprising:
receiving a response to the message, wherein the response to the message is transmitted from the communication device of the individual or patient, and further wherein the response to the message contains information for allowing the at least one of an accessing, an obtaining, a changing, an altering, and a modifying, of information contained in the individual's or patient's healthcare record or the individual's or patient's healthcare file; allowing the request to at least one of access, obtain, change, alter, and modify, the information contained in an individual's or patient's healthcare record or an individual's or patient's healthcare file; and
updating the information contained in the individual's or patient's healthcare record or the individual's or patient's healthcare file with the information regarding the individual or patient.

28. The computer-implemented method of claim 2, further comprising:
receiving information regarding the individual or patient or regarding a second individual or second patient, wherein the information regarding the individual or patient or regarding the second individual or second patient is transmitted from a computer or communication device associated with or used by a healthcare provider of the individual or patient or of the second individual or second patient, and further wherein the information regarding the individual or patient or regarding the second individual or second patient contains information regarding at least one of a symptom, an examination finding, a diagnosis, a treatment, an administration of a treatment, and a procedure;
at least one of storing the information regarding the individual or patient or regarding the second individual or second patient and updating the individual's or patient's healthcare record or the individual's or patient's healthcare file or updating a healthcare record or a healthcare file of, for, or associated with, the second individual or second patient;
generating an insurance claim in response to the storing of the information regarding the individual or patient or regarding the second individual or second patient or in response to the updating of the individual's or patient's healthcare record or the individual's or patient's healthcare file or the updating of the healthcare record or the healthcare file of, for, or associated with, the second individual or second patient, wherein the insurance claim is suitable for being automatically submitted to a healthcare insurer or a healthcare payer associated with the individual or patient or associated with the second individual or second patient or is suitable for being automatically transmitted to a computer or communication device associated with a healthcare insurer or a healthcare payer associated with the individual or patient or associated with the second individual or second patient; and
transmitting the insurance claim to the computer or communication device associated with the healthcare insurer or the healthcare payer associated with the individual or patient or associated with the second individual or second patient.

29. The computer-implemented method of claim 28, further comprising:
updating the individual's or patient's healthcare record or the individual's or patient's healthcare file, or updating a healthcare record or a healthcare file of, for, or associated with, the second individual or second patient, to include information regarding the transmitting of the insurance claim to the computer or communication device associated with the healthcare insurer or the healthcare payer associated with the individual or patient or associated with the second individual or second patient.

30. The computer-implemented method of claim 2, further comprising:

storing information regarding at least one of a symptom, an examination finding, a diagnosis, a treatment, an administration of a treatment, and a procedure, regarding the individual or patient or regarding a second individual or second patient;

generating a second message containing at least one of information regarding a diagnosis, information regarding a list of possible diagnoses, and information regarding a treatment; and transmitting the second message to a computer or communication device associated with a healthcare provider of the individual or patient or of a second individual or second patient, to the communication device of the individual or patient, or to a second communication device of the individual or patient or of the second individual or second patient.

31. The computer-implemented method of claim 2, further comprising:

generating a second message containing information regarding a prescribed treatment for the individual or patient of for a second individual or patient; and transmitting the second message to a computer or communication device associated with a healthcare provider of the individual or patient or of the second individual or second patient.

32. The computer-implemented method of claim 2, further comprising:

updating the individual's or patient's healthcare record or the individual's or patient's healthcare file with information regarding a diagnosis or a prescribed treatment, or updating a healthcare record or a healthcare file of, for, or associated with, a second individual or second patient with information regarding a diagnosis or a prescribed treatment.

33. The computer-implemented method of claim 2, further comprising:

receiving information regarding a treatment to be administered to the individual or patient or to be administered to a second individual or second patient or information regarding a procedure to be performed on the individual or patient or a procedure to be performed on a second individual or second patient;

processing the information regarding a treatment to be administered to the individual or patient or to be administered to the second individual or second patient or the information regarding a procedure to be performed on the individual or patient or a procedure to be performed on the second individual or second patient;

generating a second message containing information regarding whether the treatment to be administered to the individual or patient or to be administered to the second individual or second patient, or whether the procedure to be performed on the individual or patient or the procedure to be performed on the second individual or second patient, is correct or incorrect; and transmitting the second message to a computer or communication device associated with or used by a healthcare provider or a healthcare facility.

34. The computer-implemented method of claim 2, further comprising:

receiving a request to evaluate at least one of a diagnosis and a treatment regarding the individual or patient or regarding a second individual or second patient;

processing the request;

generating a second message in response to the request, wherein the second message contains information regarding whether or not the at least one of a diagnosis and a treatment regarding the individual or patient or regarding a second individual or second patient is appropriate or in-line with a current standard; and transmitting the second message to a computer or communication device associated with or used by a healthcare insurer or a healthcare payer of the individual or patient, a healthcare insurer or a healthcare payer of the second individual or second patient, the individual or patient, the second individual or second patient, a healthcare provider of the individual or patient, or a healthcare provider of the second individual or second patient.

35. The computer-implemented method of claim 2, further comprising:

generating a second message containing information regarding an admitting of the individual or patient or an admitting of a second individual or second patient to a hospital or to a healthcare facility or containing information regarding a diagnosis regarding the individual or patient or regarding a second individual or second patient; and transmitting the second message to a computer or communication device associated with or used by a healthcare provider, a healthcare insurer, or a healthcare payer.

36. The computer-implemented method of claim 2, further comprising:

generating a second message containing information that a healthcare provider is available to perform a treatment or a procedure; and transmitting the second message to the communication device of the individual or patient or to a second communication device associated with or used by the individual or patient or associated with or used by a second individual or second patient.

37. The computer-implemented method of claim 2, further comprising:

receiving and storing information regarding a restriction or limitation regarding an ability of the person or the entity, or regarding an ability of a second person or a second entity, to access the information contained in an individual's or patient's healthcare record or an individual's or patient's healthcare file, wherein the information regarding a restriction or limitation is transmitted from the communication device or is transmitted from a second communication device of or used by the individual or patient; and determining, using the information regarding a restriction or limitation, whether the person or the entity is allowed or authorized to access the information contained in an individual's or patient's healthcare record or an individual's or patient's healthcare file.

38. The computer-implemented method of claim 37, wherein the information regarding a restriction or limitation contains information regarding at least one of a healthcare provider, a healthcare payer, a healthcare insurer, and an authorized entity, and information regarding a designated purpose for allowing each of the at least one of a healthcare provider, a healthcare payer, a healthcare insurer, and an authorized entity, to access the information contained in an individual's or patient's healthcare record or an individual's or patient's healthcare file, wherein the designated purpose is at least one of to perform a diagnosis, to perform a diagnosis for a certain ailment, illness, or symptom, to provide a second opinion, to verify or disprove a condition or a pre-existing condition, to submit an insurance claim, and to process an insurance claim.

39. The computer-implemented method of claim 37, wherein the information regarding a restriction or limitation contains information for restricting or limiting access by the person or the entity, or for restricting or limiting access by a second person or a second entity, to a portion or portions of, or to a section or sections of, the information contained in an individual's or patient's healthcare record or an individual's or patient's healthcare file.

40. The computer-implemented method of claim 2, further comprising:

storing information regarding a restriction or limitation regarding an ability of the person or the entity, or regarding an ability of a second person or a second entity, to access the information contained in an individual's or patient's healthcare record or an individual's or patient's healthcare file; and determining, using the information regarding a restriction or limitation, whether the person or the entity is allowed or authorized to access the information contained in an individual's or patient's healthcare record or an individual's or patient's healthcare file.

* * * * *

UNITED STATES PATENT AND TRADEMARK OFFICE
CERTIFICATE OF CORRECTION

| | | |
|---|---|---|
| PATENT NO. | : 7,490,048 B2 | Page 1 of 1 |
| APPLICATION NO. | : 09/987226 | |
| DATED | : February 10, 2009 | |
| INVENTOR(S) | : Raymond Anthony Joao | |

It is certified that error appears in the above-identified patent and that said Letters Patent is hereby corrected as shown below:

Column 55, line 34, change "notification_report" to "notification report".

Column 55, line 55, change "individual or patient wherein" to "individual or patient, wherein".

Column 60, line 29, change "request, and identification" to "request and identification".

Signed and Sealed this

Thirty-first Day of March, 2009

JOHN DOLL
*Acting Director of the United States Patent and Trademark Office*